US009815887B2

United States Patent
Chen et al.

(10) Patent No.: US 9,815,887 B2
(45) Date of Patent: Nov. 14, 2017

(54) MONOCLONAL ANTIBODIES THAT NEUTRALIZE A NOROVIRUS

(71) Applicant: THE UNITED STATES OF AMERICA, as represented by the Secretary, Department of Health and Human Services, Washington, DC (US)

(72) Inventors: Zhaochun Chen, North Potomac, MD (US); Robert H. Purcell, Gaithersburg, MD (US); Lisbeth Kim Green, Olney, MD (US); Stanislav Sosnovtsev, North Potomac, MD (US); Karin Bok, Bethesda, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/359,438

(22) Filed: Nov. 22, 2016

(65) Prior Publication Data

US 2017/0066815 A1  Mar. 9, 2017

Related U.S. Application Data

(62) Division of application No. 14/767,274, filed as application No. PCT/US2014/015809 on Feb. 11, 2014, now Pat. No. 9,534,041.

(60) Provisional application No. 61/763,879, filed on Feb. 12, 2013.

(51) Int. Cl.
| | | |
|---|---|---|
| *C07K 16/10* | (2006.01) | |
| *A61K 39/42* | (2006.01) | |
| *A61K 45/06* | (2006.01) | |
| *G01N 33/569* | (2006.01) | |
| *A61K 39/00* | (2006.01) | |

(52) U.S. Cl.
CPC ............ *C07K 16/10* (2013.01); *A61K 39/42* (2013.01); *A61K 45/06* (2013.01); *G01N 33/56983* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01); *G01N 2333/08* (2013.01); *G01N 2469/10* (2013.01)

(58) Field of Classification Search
None
See application file for complete search history.

(56) References Cited

FOREIGN PATENT DOCUMENTS

WO  WO 2005/030806 A2  4/2005

OTHER PUBLICATIONS

Lindesmith et al., Monoclonal Antibody-Based Antigenic Mapping of Norovirus GII.4-2002, 2011, Journal of Virology, vol. 86, No. 2, pp. 873-883.*
Bok et al., Chimpanzees as an animal model for human norovirus infection and vaccine development, 2011, PNAS, vol. 108, No. 1, pp. 325-330.*
Bok et al., "Chimpanzees as an animal model for human norovirus infection and vaccine development," *PNAS* 108(1): 325-330 (Jan. 4, 2011).
Chachu et al., "Antibody is critical for the clearance of murine norovirus infection," *Journal of Virology* 82(13): 6610-6617 (Jul. 1, 2008).
Chen et al., "Development of Norwalk virus-specific monoclonal antibodies with therapeutic potential for the treatment of Norwalk virus gastroenteritis," *Journal of Virology* 87(17):9547-9557 (Sep. 1, 2013).
Czakó et al., "Serum hemagglutination inhibition activity correlates with protection from gastroenteritis in persons infected with norwalk virus," *Clinical and Vaccine Immunology* 19(2): 284-287 (Feb. 2012).
Ettayebi et al., "Recombinant norovirus-specific scFv inhibit virus-like particle binding to cellular ligands," *Virology Journal* 5(1): 1-8 (Jan. 31, 2008).
International Search Report from parent PCT Application No. PCT/US2014/015809, 9 pages (dated Jul. 9, 2014).
LoBue et al., "Alphavirus-adjuvanted norovirus-like particle vaccines: heterologous, humoral, and mucosal immune responses protect against murine norovirus challenge," *Journal of Virology* 83(7): 3212-3227 (Apr. 2009).
Para et al., "Multiple antigenic sites are involved in blocking the interaction of GII.4 norovirus capsid with ABH histo-blood group antigens," *Journal of Virology* 86(13): 7414-7426 (Jul. 1, 2012).

(Continued)

*Primary Examiner* — Benjamin P Blumel
(74) *Attorney, Agent, or Firm* — Klarquist Sparkman, LLP

(57) ABSTRACT

Monoclonal neutralizing antibodies are disclosed that specifically bind to a Norovirus. In some embodiments, the Norovirus is a genogroup II Norovirus or a Genogroup II Norovirus. In some embodiments, the Norovirus is Nowalk virus. In some embodiments, the monoclonal antibodies specifically bind VP1. Also disclosed are compositions including the disclosed antibodies, nucleic acids encoding these antibodies, expression vectors including the nucleic acids, and isolated host cells that express the nucleic acids. The antibodies and compositions disclosed herein can be used for detecting the presence of a Norovirus in a biological sample, or detecting a Norovirus infection. In addition, the neutralization ability of the disclosed antibodies makes them ideal for treating a subject with a Norovirus infection. Thus, disclosed are methods of treating and/or preventing these infections.

22 Claims, 14 Drawing Sheets

(56) References Cited

OTHER PUBLICATIONS

Rocha-Pereira et al., "Norovirus: Targets and tools in antiviral drug discovery," *Biochemical Pharmacology* 92: 1-11 (2014).
Written Opinion from parent PCT Application No. PCT/US2014/015809, 11 pages (dated Jul. 9, 2014).

* cited by examiner

FIG. 2

A. Heavy chain

```
         FRW1                           CDR1                FRW2                    CDR2
B7   EVQLEESGGDLVQPGGSLTLSCAASGFTFS   RYWMS   WVRQAPGKGPEWVA   SIKKDGSETF   YADS
D8   ******G******RV****P*N          G**IH   *******L***S     RVNS**RI*N   F***
E5   ******G**G*IK*****R*****T       K*V*H   *****E*LQ**S     A*GGS*GSAW   ****
G4   ****QGK*R***        H*V*Y   *****E*L***S     T*SGS**S*W   *P**
F11  ******V*TS***************   I*H   ***E*L***S     LLYS---*GS*Y ****

FRW3                                CDR3                                    FRW4
B7   VKGRFIISRDIAKTSLYLQMNSLRADTAVYYCLR   AWYS------------SAYDF              WGQGTLVTV:
D8   *M****TM****S*V*********E***M**S*    GGYTG-----------YPEGH              ********
E5   *****T***NS*NT*********E*********A*  DHARYSG---------YNSPHEVDS          *****A*
G4   ***TVNS*NT*******G*A*****A*  LQG-------------QLVY               *L**
F11  ***T*NS*NT*******E*******A*  DYSGSWVGDEARSYYYYYMDV              KT***
```

B. Light chain

```
         FRW1                           CDR1              FRW2                   CDR2
B7   ELELTQSPSSLSASVGDRVTITC   RASQSISNYLN   WYQQKPGKAPNLLIY   YASTLQS   GVPS
D8   ****QM****A***S*******    ****G*IH*A    *******V*K****    A******   ****
E5   QM*************T    **G*sw*A    *******R*K**    A**   **
G4   QV*************     GY*     *******V*K**    K3***E* ****
F11  ******************        Q***D**Y*     *****R**V*K****   S**Y*H*   ****

FRW3                                CDR3            FRW4
B7   RFSGSGSGTDFTLTISSLQPEDFATYYC   QHGYGA---IA   FGQGTRLEIKRT
D8   **************N****V*     *KYDS*-PFT    PKVD****
E5   ************************      *KYNS*-PLT    GKV*****
G4   ***********E*D*F*     *QYSSNPPLT    GKV*****
F11  ****************V****     *RT*-NAPYT    QKV*****
```

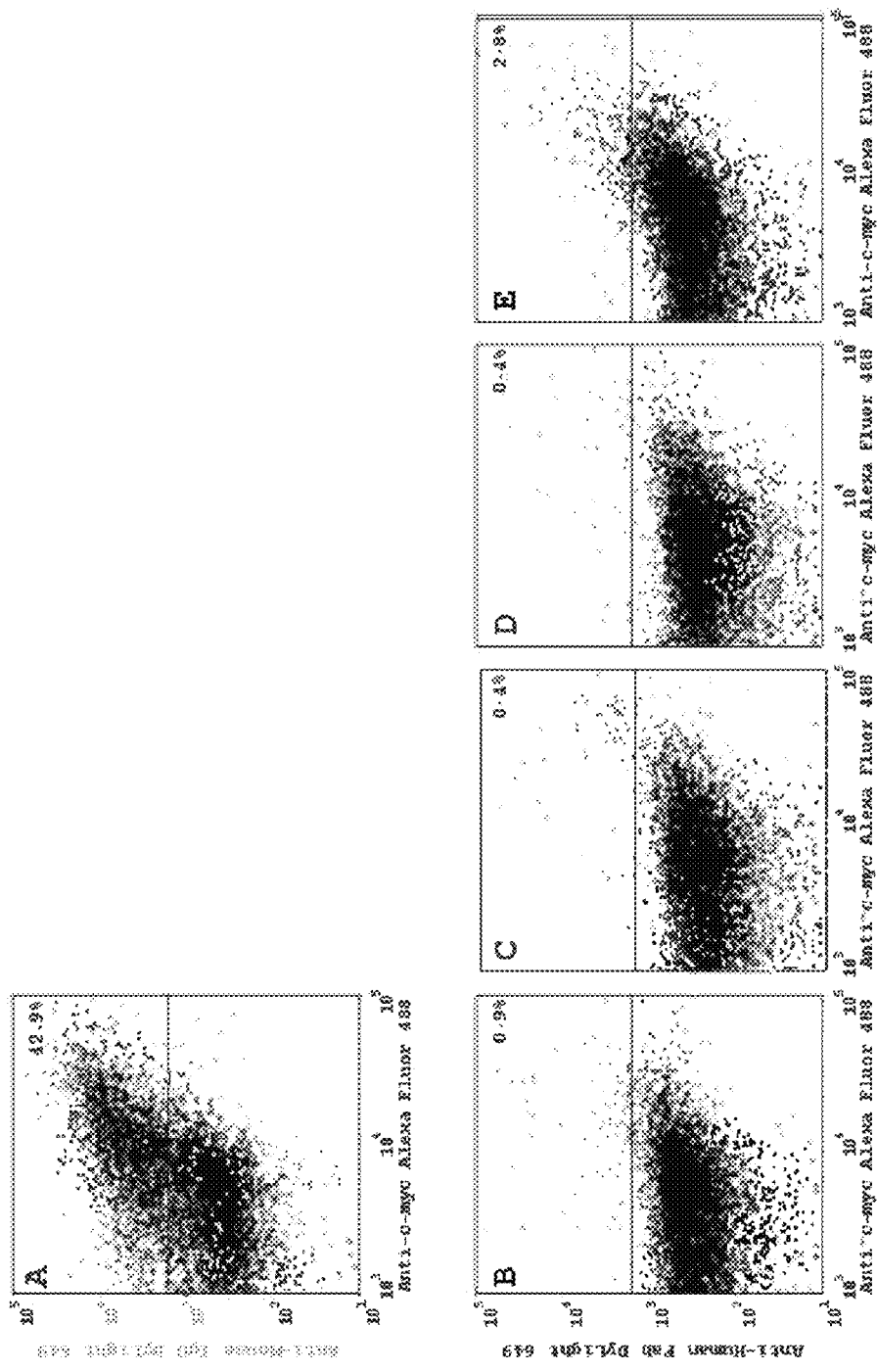

FIG. 4A
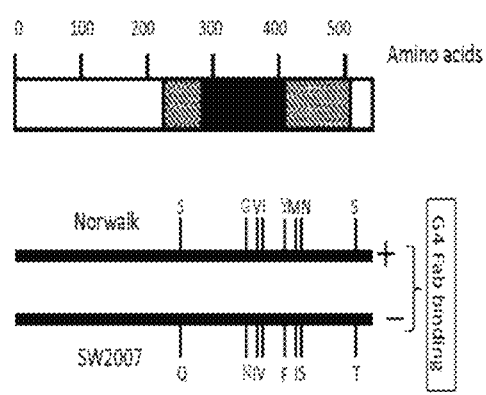
FIG. 4C
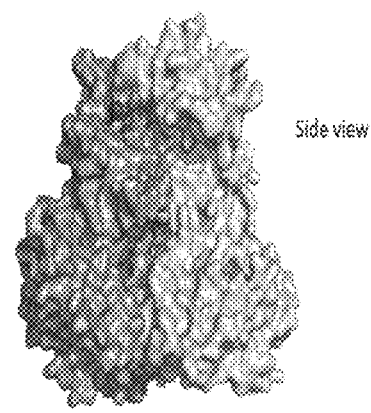
Side view
FIG. 4B
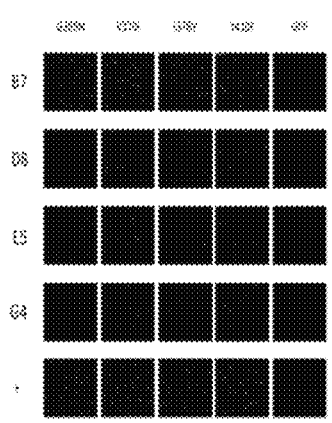
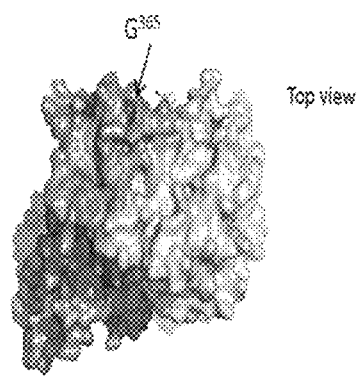
Top view

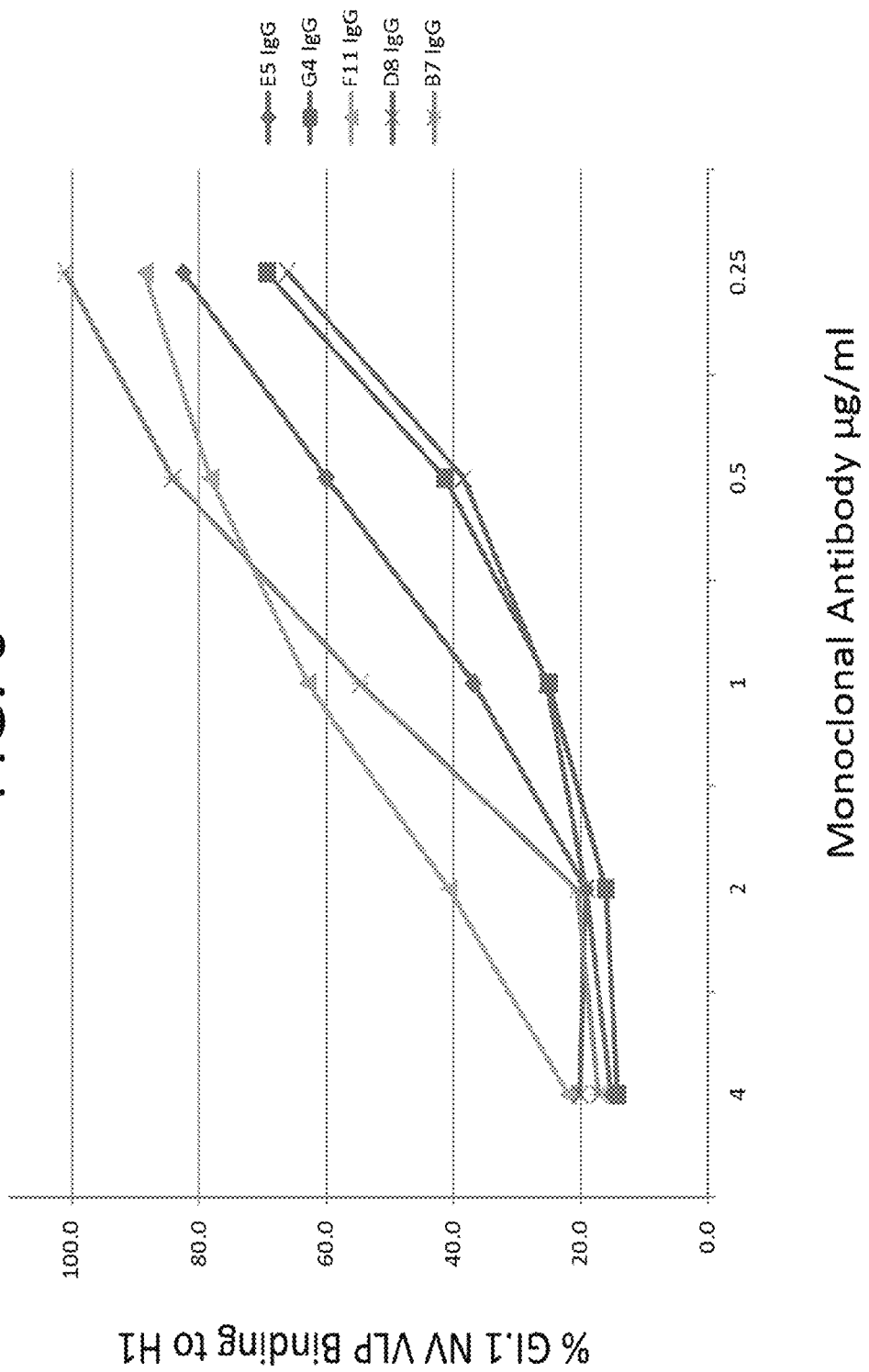

FIG. 7

VH and VL sequences of anti-NoV GII.4 mAbs

```
         FWR1                              HCDR1            FWR2            HCDR2
C9H    EVQLEESGGVLVKPGGSIRLSCAASGFTFS     SHAMH     WVRQAPGKGLEWV     AIINS- -GHPAD
G3H    --EVQLEQSGGGLVKPGGSLRLSCAGSGFSFS   AHTIN     WVRQAPGKGLEWV     GFIRSQAQGGTRE
B72H   --EVQIEQSGAEVKKPGSSVKVSCKISGGTFS   RHPIS     WVRQAPGQGLIHM     GATIIR- -AGTTK
D4H    LEEVQLVESGPGLVKPSETLSLTCAVSGASIR   RANWWG    WIRQAPGKGLEWL     GSIFIN- --AGTI

FWR 3                                                       HCDR3
C9H    YADSVKDRFTISRDNSKNTLYLQMDSLRPEDTAFYYCAR    EGDQ- - -QDVAD
G3H    YAASVKGRIILSRDDSENSAVLQMNSLNTGDTAVYYCAR    DSSRGYY- SYYLDV
B72H   YEQRFQGRITTADESTGTAYMELHSLTSEDTGLYFCAT     - -DRMGTFD- -ELLFDS
D4H    YNPSLTGRVTVSADTSRNLFSKLGSVTAADTAVYYCVK     SYGDGDNTNSFYYMDV

FWR4
C9H    WGQGTLVTVSSAST
G3H    WGKCTTVTVSSAST
B72H   WGQGTLVTVSSAST
D4H    WGKGTSVIVSSAST

FWR1                                       LCDR1              FWR2            LCDR2
B72L   EIQMTQSPASLSASVGDRVTITC    RASQGTRNNLG    WYQQKPGKPPKLLIY   AASTLQS  GVPS
G3L    - -ELTQSPSSLSASVGDRVTITC   RASQGISNRLN    WYQQKPGKAPKLLIY   DASSLES  GVPS
D4L    DVVMTQSPSSLSASVGDRVTITC    RASQDIRNNLA    WYQHKPGKAPKLLIY   DASKLQS  GVPL
C9L    - -ELTQSPSTLSASVGDRVTITC   RASEDIMSYLA    WYQQKPAKAPRLLIY   YASSLQS  GVPS

FWR3                                       LCDR3              FWR4
B72L   RFSGSGSGTGFTLTITSSIQPEDFATYC    LQDY-DFPLT     FGGGTKVEIKRT
G3L    RFSGSGSGTDFTLTISSLQPEDFATYC     QQFN-SYPLT     FGGGTKVEIKRT
D4L    RFSGSGSGTDYTLFISSLQPEDFATYC     QQYKDTDTPYS    FGQGTKVDIKRT
C9L    RFSGSGSGTEFTLTISSLQPEDFATYC     QQLH-TFPIT     FGPGTRLDIKRT
```

FIG. 9

| Name | FWR1 | CDR1 | FWR2 | CDR2 | FWR3 | CDR3 | FWR4 | Variable Domain |
|---|---|---|---|---|---|---|---|---|
| B7-H | 1 | 2 | 3 | 4 | 5 | 6 | 7 | 8 |
| B7-L | 9 | 10 | 11 | 12 | 13 | 14 | 15 | 16 |
| D8-H | 17 | 18 | 19 | 20 | 21 | 22 | 23 | 24 |
| D8-L | 25 | 26 | 27 | 28 | 29 | 30 | 31 | 32 |
| E5-H | 33 | 34 | 35 | 36 | 37 | 38 | 39 | 40 |
| E5-L | 41 | 42 | 43 | 44 | 45 | 46 | 47 | 48 |
| G4-H | 49 | 50 | 51 | 52 | 53 | 54 | 55 | 56 |
| G4-L | 57 | 58 | 59 | 60 | 61 | 62 | 63 | 64 |
| F11-H | 65 | 66 | 67 | 68 | 69 | 70 | 71 | 72 |
| F11-L | 73 | 74 | 75 | 76 | 77 | 78 | 79 | 80 |
| C9-H | 81 | 82 | 83 | 84 | 85 | 86 | 87 | 88 |
| C9-L | 89 | 90 | 91 | 92 | 93 | 94 | 95 | 96 |
| G3-H | 97 | 98 | 99 | 100 | 101 | 102 | 103 | 104 |
| G3-L | 105 | 106 | 107 | 108 | 109 | 110 | 111 | 112 |
| B72-H | 113 | 114 | 115 | 116 | 117 | 118 | 119 | 120 |
| B72-L | 121 | 122 | 123 | 124 | 125 | 126 | 127 | 128 |
| D4-H | 129 | 130 | 131 | 132 | 133 | 134 | 135 | 136 |
| D4-L | 137 | 138 | 139 | 140 | 141 | 142 | 143 | 144 |

FIG. 10A

Nucleotide sequence of variable domain heavy chain of anti-NoV gII.4

>872.H (SEQ ID NO: 146)

GAGGTGCAGCTCGAGCAGTCAGGGGCTGAGGTGAAGAAGCCGGGGTCTTCAGTGAAGGTCTCTTGTAAGATTTC
GGGAGGCACCTTCAGCAGACATCCTATCAGCTGGGTCCGACAGGCCCCTGGACAAGGGCTTCTATGGATGGGAG
CGATCATCCTTAGGGCTGGAACGACAAAGTACGAGCAGAGGTTTCAGGGCAGAATCACAATTACCGCGGACGAAT
CCACGGGCACAGCCTACATGGAACTCCACAGCCTGACTTCTGAGGACACGGGCCTCTATTTCTGTGCGACAGATAG
GATGGGGACGTTTGACGAATTGCTGTTTGACTCCTGGGGCCAGGGAACCCTGGTCACCGTCTCGTCCGCCTCCACC

>C9.H (SEQ ID NO: 147)

GAGGTGCAGCTCGAGGAGTCTGGGGGAGTCTTGGTAAAGCCGGGGGGGTCCCTAAGACTCTCCTGTGCAGCCTC
TGGATTCACGTTCAGTAGCCATGCTATGCACTGGGTTCGCCAGGCACCAGGGAAGGGTCTGGAGTGGGTCGCAAT
CATTAATAGTGGTCATAGAGCAGACTATGCAGACTCCGTGAAGGACAGATTCACCATCTCCAGAGACAATTCCAAG
AATACACTGTATCTTCAAATGGACAGCCTGAGACCTGAGGATACGGCTTTTTATTACTGTGCGAGAGAGGGCGAC
CAACAAGACGTTGCTGACTGGGGCCAGGGAACCCTGGTCACCGTCTCCTCAGCCTCCACC

>G3.H (SEQ ID NO: 148)

GAGGTGCAGCTCGAGCAGTCTGGGGGAGGCTTGGTAAAGCCTGGGGGATCCCTGAGGCTCTCCTGTGCAGGGTC
TGGATTCAGCTTCAGTGCCCACACAATTAACTGGGTCCGGCAGGCTCCAGGGAAGGGGCTGGAGTGGGTAGGTTT
CATCAGAAGTCAGGCTCAGGGTGGGACAAGAGAATACGCCGCGTCTGTGAAAGGCAGAATTATTCTCTCAAGAG
ATGATTCCGAAAACAGTGCCTATCTGCAAATGAACAGCCTGAATACCGGCGACACAGCCGTGTATTATTGTGCAAG
AGATTCTAGTCGCGGCTATTACTCCTACTACTTGGACGTCTGGGGCAAAGGGACCACGGTCACCGTCTCCTCAGCC
TCCACC

>D4.H (SEQ ID NO: 149)

CTCGAGGAGGTGCAGCTGGTGGAGTCGGGCCCAGGACTGGTGAAGCCTTCAGAGACCCTGTCCCTCACATGCGCT
GTCTCTGGTGCCTCCATCAGACGTGCTAATTGGTGGGGCTGGATCCGGCAGGCCCCAGGGAAGGGACTGGAGTG
GCTCGGCAGTATCTTTATTAATGCGGGCACCATTTATAACCCGTCCCTCACGGGTCGAGTCACCGTCTCAGCGGAC
ACGTCCAAGAACCTGTTCTCCCTGAAGCTGGGCTCTGTGACCGCCGCGGACACGGCAGTCTATTACTGTGTGAAAT
CCTATGGTGATGGTGATGATAATTACAACAGTTTCTACTACTACATGGACGTCTGGGGCAAAGGGACCTCGGTCAT
CGTCTCCTCAGCCTCCACC

FIG. 10B

>B72.L (SEQ ID NO: 150)

GAGCTCCAGATGACCCAGTCTCCAGCCTCCCTGTCTGCATCTGTAGGAGACAGAGTCACCATCACTTGCCGGGCAA
GTCAGGGCATCAGAAACAATTTAGGCTGGTATCAGCAGAAACCAGGGAAACCCCCTAAGCTCCTGATCTATGCTG
CATCCACTTTACAAAGTGGGGTCCCATCAAGGTTCAGTGGCAGTGGGTCTGGCACAGGTTTCACTCTCACCATCAG
CAGCCTGCAGCCTGAAGATTTTGCGACTTATTACTGTCTACAAGATTACGATTTCCCGCTCACTTTCGGTGGAGGGA
CCAAGGTTGAGATCAAACGAACT

>C9.L (SEQ ID NO: 151)

GAGCTCACGCAGTCTCCATCGACCCTGTCTGCATCTGTAGGGGACAGAGTCACCATCACTTGCCGGGCCAGTGAG
GACATTATGAGTTATTTAGCCTGGTATCAGCAAAAACCAGCAAAAGCCCCCAGGCTCCTCATCTATTATGCATCTAG
TTTGCAAAGTGGGGTCCCATCGAGATTCAGCGGCAGTGGATCTGGGACAGAATTCACTCTCACAATCAGCAGCCT
GCAGCCTGAAGATTTTGCAACTTATTACTGTCAGCAGCTTCATACTTTCCCGATCACCTTCGGCCCAGGGACGCGAC
TGGACATTAAACGAACT

>G3.L (SEQ ID NO: 152)

GAGCTCACGCAGTCTCCATCCTCCCTGTCTGCATCTGTAGGAGACAGAGTCACCATCACTTGCCGGGCAAGTCAGG
GCATTAGCAATAGATTAAATTGGTATCAGCAGAAACCAGGGAAAGCTCCTAAGCTCCTGATCTATGATGCCTCCAG
TTTGGAAAGTGGGGTCCCATCAAGGTTCAGCGGCAGTGGATCTGGGACAGATTTCACTCTCACCATCAGCAGCCA
GCAGCCTGAAGATTTTGCAACTTATTACTGTCAACAGTTTAATAGTTACCCGCTCACTTTCGGTGGAGGGACCAAG
GTGGAGATCAAACGAACT

>D4.L (SEQ ID NO: 153)

GATGTTGTGATGACTCAGTCTCCATCCTCCCTGTCTGCATCTGTAGGAGACAGAGTCACCATCACTTGCCGGGCCA
GTCAGGACATTAGGAATAAATTTAGCCTGGTATCAGCACAAACCAGGGAAAGCCCCCAAACTCCTCATCTATTATGC
ATCCAAATTGCAAAGTGGGGTCCCATTAAGGTTCAGCGGCAGTGGATCTGGGACGGATTACACGCTATTCATCAG
CAGCCTGCAGCCTGAAGATTTTGCAACTTATTACTGTCAACAGTATAAGACTGATACTCCGTACAGTTTTGGCCAG
GGGACCAAAGTGGATATCAAACGTACG

FIG. 10C

>B7.H (SEQ ID NO: 154)

GAGGTGCAGCTCGAGGAGTCTGGGGGAGACTTGGTCCAGCCTGGGGGGTCCCTGACACTCTCCTGTGCAGCCTCT
GGTTTCACCTTCAGTAGATATTGGATGAGCTGGGTCCGCCAGGCTCCGGGGAAGGGGCCGGAGTGGGTGGCCAG
CATAAAGAAAGATGGAAGTGAGACATTCTATGCGGACTCTGTGAAGGGCCGATTCATCATCTCCAGAGACATCGC
CAAGACCTCATTGTATTTGCAAATGAACAGCCTGAGAGCCGACGACACGGCTGTATATTACTGTCTGCGGGCCTGG
TATAGCAGCGCCTACGACTTCTGGGGCCAGGGAACCCTGGTCACCGTCTCC

>D8.H (SEQ ID NO: 155)

GAGGTGCAGCTCGAGGAGTCTGGGGGAGGCCTAGTTCAGCCTGGGGGGTCCCTGAGAGTCTCCTGTGCAGCCTC
TGGATTCCCCTTCAATGGTTACTGGATACACTGGGTCCGCCAAGCTCCAGGGAAGGGGCTGGAGTGGGTCTCCCG
TGTTAACAGTGATGGAAGGATCACAAATTTTGCGGACTCCGTGATGGGCCGATTCACCATGTCCAGAGACAACGC
CAAGAGCACGGTGTATCTGCAAATGAACAGCCTGAGAGCCGAGGACACGGCTATGTATTATTGCAGTAGAGGTG
GATATACTGGCTACCCAGAAGGCCACTGGGGCCAGGGAACCCTGGTCACCGTCTCC

>E5.H (SEQ ID NO: 156)

GAGGTGCAGCTCGAGCAGTCTGGGGGAGGCTTGATAAAGCCTGGGGGTTCCCTGAGACTCTCGTGTGCAGCCTCT
GGATTCACCTTCACTAAGTATGTTATGCACTGGGTCCGCCAGGCTCCAGAGAAGGGGCTGCAGTGGGTCTCAGCT
ATTGGTGGTAGTGGTGGTAGCGCGTGGTATGCAGACTCTGTCAAGGGCCGATTCACCATCTCCAGAGACAATTCC
AAGAACACACTGTATCTACAAATGAATAGCCTGAGAGCCGAGGACACGGCCGTCTATTACTGTGCGAGAGATCAC
GCCCGATATAGTGGCTACAATTCTCCCCATGAAGTGGACTCATGGGGCCAGGGAACCCTGGTCGCCGTCTCC

>G4.H (SEQ ID NO: 157)

GAGGTGCAGCTCGAGGAGTCTGGGGGAGGCCTGGTAAAGCCTGGGGGTTCCCTGAGACTCTCGTGTGCAGCCTC
TGGATTCACCTTCAGTCATTATGTTATGTATTGGGTCCGCCAGGCTCCAGAGAAGGGGCTGGAGTGGGTCTCAACT
ATTAGTGGTAGCGGTAGTAGCACGTGGTATCCAGACTCTGTCAAGGGCCGATTCACCGTTTCCAGAGACAATTCCA
AGAACACATTGTATCTGCAAATGAACAGCCTGAGAGGCGACGACACGGCCGTGTATTACTGTGCGAGACTTCAGG
GGCAGCTAGTTTACTGGGGCCTGGGAACCCTGGTCACCGTCTCC

>F11.H (SEQ ID NO: 158)

GAGGTGCAGCTCGAGCAGGTGCAGCTGGTGGAGACTGGAGGAAGCTTGGTCCAGCCTGGGGGGTCCCTGAGAC
TCTCCTGTGCAGCCTCTGGATTCAGCGTCAGTATCTACCACATGAGCTGGGTCCGCCAGGCTCCAGGGAAGGGGC
TGGAGTGGGTCTCACTTCTTTATAGTGGTGGTAGCACATACTACGCAGACTCCGTGAAGGGCCGATTCACCATCTC
CAGAGACAATTCCAAGAACACGCTGTATCTGCAAATGAACAGCCTGAGAGCTGAGGACACGGCTGTATATTACTG
TGCAAGAGATTATAGCGGCAGCTGGGTCGGGGATGAAGCCCGCTCTTACTACTACTACTACATGGACGTCTG
GGGCAAGGGGACCACGGTCACCGTCTCC

FIG. 10D

>B7.L (SEQ ID NO: 159)

GAGCTCACCCAGTCTCCATCCTCCCTGTCTGCATCTGTAGGAGACAGAGTCACCATCACTTGCCGGGCAAGTCAGA
GCATTAGCAACTATTTGAATTGGTATCAGCAGAAGCCAGGGAAAGCCCCTAACCTCCTGATCTATTATGCATCCAC
TTTGCAAAGTGGGGTCCCATCAAGGTTCAGTGGCAGTGGATCTGGGACAGATTTCACTCTCACCATCAGCAGTCTG
CAACCTGAGGATTTTGCAACTTATTACTGTCAACATGGTTACGGTGCGATCGCCTTCGGCCAAGGGACACGACTGG
AGATTAAACGAACT

>E5.L (SEQ ID NO: 160)

GAGCTCACCCAGTCTCCATCCTCCCTGTCTGCATCTGTAGGAGACAGAGTCACCATCACTTGCCGGGCGAGTCAGG
GCATTAGCAATTATTTAGCCTGGTATCAGCAGAAACCAGGGAAAGTTCCTAAGCTCCTGATCTATGCTGCATCCAC
TTTGCAATCAGGGGTCCCATCTCGGTTCAGTGGCAGTGGATCTGGGACAGATTTCACTCTCACCATCAGCAGCCTG
CAGCCTGAAGATGTTGCAACTTATTACTGTCAAAAGTATAACAGTGCCCCTCTCACTTTCGGTGGAGGGACCAAGG
TGGAGATCAAACGAACT

>D8.L (SEQ ID NO: 161)

GAGCTCCAGATGACCCAGTCTCCATCCTCCCTGTCTGCAGCTGTAGGAGACAGCGTCACCATCACTTGCCGGGCGA
GTCAGGGCATTAGCATTCATTTAGCCTGGTATCAGCAAAAACCAGGGAAAGTTCCTAATCTCCTGATCTATGCTGC
GTCCACTTTGCAATCAGGGGTCCCATCTCGGTTCAGTGGCAGTGGCTCTGGCACAGATTTCACTCTCACCATCAGC
AACCTCCAGCCTGAGGATGTTGCAACTTATTACTGTCAAAAGTATGACAGTGCCCCATTCACTTTCGGCCCTGGGA
CCAAAGTGGATATCAAACGAACT

>G4.L (SEQ ID NO: 162)

GAGCTCCAGATGACCCAGTCTCCTTCCACCCTGTCCGCATCTGTAGGAGACAGAGTCACCATCACTTGCCGGGCCA
GTCAGGGTATTAGTAGCTGGTTAGCCTGGTATCAGCAGAAACCAGGGAGAGCCCCTAAACTCCTGATCTATAAGT
CATCTACTTTAGAAAGTGGGGTCCCATCAAGATTCAGCGGCAGTGGATCTGGGACAGAGTTCACTCTCACTATCAG
CAGCCTGCAGCCTGATGATTTTGCAACTTATTTCTGCCAACAATATAGCAGTAACCCTCCACTGACTTTCGGTGGAG
GGACCAAGGTGGAGATCAAACGAACT

>F11.L (SEQ ID NO: 163)

GAGCTCCAGGTGACCCAGTCTCCATCCTCCCTGTCTGCATCTGTAGGAGACAGAGTCACCATCACTTGCCAGGCGA
GTCAGGACATTAGCTACTATTTAAATTGGTATCAGCAGAGACCAGGGAAAGTTCCTAAGCTCCTTATCTATAGTGC
ATCCTATTTGCATTCTGGAGTCCCGTCTCGGTTCAGTGGCAGTGGATCTGGGACAGATTTCACTCTCACTATCAGCA
GCCTGCAGCCTGAAGATGTTGCAACTTATTACTGTCAACGGACTTACAATGCCCCGTACACTTTTGGCCAGGGGAC
CAAGGTGGAGATCAAACGTACG

```
                       SEQUENCE LISTING

<160> NUMBER OF SEQ ID NOS: 163

<210> SEQ ID NO 1
<211> LENGTH: 30
<212> TYPE: PRT
<213> ORGANISM: Pan troglodytes

<400> SEQUENCE: 1

Glu Val Gln Leu Glu Glu Ser Gly Gly Asp Leu Val Gln Pro Gly Gly
1               5                   10                  15

Ser Leu Thr Leu Ser Cys Ala Ala Ser Gly Phe Thr Phe Ser
            20                  25                  30

<210> SEQ ID NO 2
<211> LENGTH: 5
<212> TYPE: PRT
<213> ORGANISM: Pan troglodytes

<400> SEQUENCE: 2

Arg Tyr Trp Met Ser
1               5

<210> SEQ ID NO 3
<211> LENGTH: 14
<212> TYPE: PRT
<213> ORGANISM: Pan troglodytes

<400> SEQUENCE: 3

Trp Val Arg Gln Ala Pro Gly Lys Gly Pro Glu Trp Val Ala
1               5                   10

<210> SEQ ID NO 4
<211> LENGTH: 10
<212> TYPE: PRT
<213> ORGANISM: Pan troglodytes

<400> SEQUENCE: 4

Ser Ile Lys Lys Asp Gly Ser Glu Thr Phe
1               5                   10

<210> SEQ ID NO 5
<211> LENGTH: 39
<212> TYPE: PRT
```

```
<213> ORGANISM: Pan troglodytes

<400> SEQUENCE: 5

Tyr Ala Asp Ser Val Lys Gly Arg Phe Ile Ile Ser Arg Asp Ile Ala
1               5                   10                  15

Lys Thr Ser Leu Tyr Leu Gln Met Asn Ser Leu Arg Ala Asp Asp Thr
            20                  25                  30

Ala Val Tyr Tyr Cys Leu Arg
        35

<210> SEQ ID NO 6
<211> LENGTH: 9
<212> TYPE: PRT
<213> ORGANISM: Pan troglodytes

<400> SEQUENCE: 6

Ala Trp Tyr Ser Ser Ala Tyr Asp Phe
1               5

<210> SEQ ID NO 7
<211> LENGTH: 10
<212> TYPE: PRT
<213> ORGANISM: Pan troglodytes

<400> SEQUENCE: 7

Trp Gly Gln Gly Thr Leu Val Thr Val Ser
1               5                   10

<210> SEQ ID NO 8
<211> LENGTH: 117
<212> TYPE: PRT
<213> ORGANISM: Pan troglodytes

<400> SEQUENCE: 8

Glu Val Gln Leu Glu Glu Ser Gly Gly Asp Leu Val Gln Pro Gly Gly
1               5                   10                  15

Ser Leu Thr Leu Ser Cys Ala Ala Ser Gly Phe Thr Phe Ser Arg Tyr
            20                  25                  30

Trp Met Ser Trp Val Arg Gln Ala Pro Gly Lys Gly Pro Glu Trp Val
        35                  40                  45

Ala Ser Ile Lys Lys Asp Gly Ser Glu Thr Phe Tyr Ala Asp Ser Val
    50                  55                  60

Lys Gly Arg Phe Ile Ile Ser Arg Asp Ile Ala Lys Thr Ser Leu Tyr
65                  70                  75                  80

Leu Gln Met Asn Ser Leu Arg Ala Asp Asp Thr Ala Val Tyr Tyr Cys
                85                  90                  95

Leu Arg Ala Trp Tyr Ser Ser Ala Tyr Asp Phe Trp Gly Gln Gly Thr
            100                 105                 110

Leu Val Thr Val Ser
        115

<210> SEQ ID NO 9
<211> LENGTH: 23
<212> TYPE: PRT
<213> ORGANISM: Pan troglodytes

<400> SEQUENCE: 9

Glu Leu Glu Leu Thr Gln Ser Pro Ser Ser Leu Ser Ala Ser Val Gly
1               5                   10                  15

Asp Arg Val Thr Ile Thr Cys
```

<210> SEQ ID NO 10
<211> LENGTH: 23
<212> TYPE: PRT
<213> ORGANISM: Pan troglodytes

<400> SEQUENCE: 10

Glu Leu Glu Leu Thr Gln Ser Pro Ser Ser Leu Ser Ala Ser Val Gly
1               5                   10                  15

Asp Arg Val Thr Ile Thr Cys
            20

<210> SEQ ID NO 11
<211> LENGTH: 15
<212> TYPE: PRT
<213> ORGANISM: Pan troglodytes

<400> SEQUENCE: 11

Trp Tyr Gln Gln Lys Pro Gly Lys Ala Pro Asn Leu Leu Ile Tyr
1               5                   10                  15

<210> SEQ ID NO 12
<211> LENGTH: 7
<212> TYPE: PRT
<213> ORGANISM: Pan troglodytes

<400> SEQUENCE: 12

Tyr Ala Ser Thr Leu Gln Ser
1               5

<210> SEQ ID NO 13
<211> LENGTH: 32
<212> TYPE: PRT
<213> ORGANISM: Pan troglodytes

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 8
<212> TYPE: PRT
<213> ORGANISM: Pan troglodytes

<400> SEQUENCE: 14

Gln His Gly Tyr Gly Ala Ile Ala
1               5

<210> SEQ ID NO 15
<211> LENGTH: 12
<212> TYPE: PRT
<213> ORGANISM: Pan troglodytes

<400> SEQUENCE: 15

Phe Gly Gln Gly Thr Arg Leu Glu Ile Lys Arg Thr
1               5                   10

<210> SEQ ID NO 16
<211> LENGTH: 108
<212> TYPE: PRT
<213> ORGANISM: Pan troglodytes

<400> SEQUENCE: 16

Glu Leu Glu Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Asn Leu Leu Ile
        35                  40                  45

Tyr Tyr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Tyr Gly Ala Ile Ala
                85                  90                  95

Phe Gly Gln Gly Thr Arg Leu Glu Ile Lys Arg Thr
            100                 105

<210> SEQ ID NO 17
<211> LENGTH: 30
<212> TYPE: PRT
<213> ORGANISM: Pan troglodytes

<400> SEQUENCE: 17

Glu Val Gln Leu Glu Glu Ser Gly Gly Gly Leu Val Gln Pro Gly Gly
1               5                   10                  15

Ser Leu Arg Val Ser Cys Ala Ala Ser Gly Phe Pro Phe Asn
            20                  25                  30

<210> SEQ ID NO 18
<211> LENGTH: 5
<212> TYPE: PRT
<213> ORGANISM: Pan troglodytes

<400> SEQUENCE: 18

Gly Tyr Trp Ile His
1               5

<210> SEQ ID NO 19
<211> LENGTH: 14
<212> TYPE: PRT
<213> ORGANISM: Pan troglodytes

<400> SEQUENCE: 19

Trp Val Arg Gln Ala Pro Gly Lys Gly Leu Glu Trp Val Ser
1               5                   10

<210> SEQ ID NO 20
<211> LENGTH: 10
<212> TYPE: PRT
<213> ORGANISM: Pan troglodytes

<400> SEQUENCE: 20

Arg Val Asn Ser Asp Gly Arg Ile Thr Asn
1               5                   10

<210> SEQ ID NO 21
<211> LENGTH: 39
<212> TYPE: PRT
<213> ORGANISM: Pan troglodytes

<400> SEQUENCE: 21

```
Phe Ala Asp Ser Val Met Gly Arg Phe Thr Met Ser Arg Asp Asn Ala
1               5                   10                  15

Lys Ser Thr Val Tyr Leu Gln Met Asn Ser Leu Arg Ala Glu Asp Thr
                20                  25                  30

Ala Met Tyr Tyr Cys Ser Arg
            35

<210> SEQ ID NO 22
<211> LENGTH: 10
<212> TYPE: PRT
<213> ORGANISM: Pan troglodytes

<400> SEQUENCE: 22

Gly Gly Tyr Thr Gly Tyr Pro Glu Gly His
1               5                   10

<210> SEQ ID NO 23
<211> LENGTH: 10
<212> TYPE: PRT
<213> ORGANISM: Pan troglodytes

<400> SEQUENCE: 23

Trp Gly Gln Gly Thr Leu Val Thr Val Ser
1               5                   10

<210> SEQ ID NO 24
<211> LENGTH: 118
<212> TYPE: PRT
<213> ORGANISM: Pan troglodytes

<400> SEQUENCE: 24

Glu Val Gln Leu Glu Glu Ser Gly Gly Leu Val Gln Pro Gly Gly
1               5                   10                  15

Ser Leu Arg Val Ser Cys Ala Ala Ser Gly Phe Pro Phe Asn Gly Tyr
                20                  25                  30

Trp Ile His Trp Val Arg Gln Ala Pro Gly Lys Gly Leu Glu Trp Val
            35                  40                  45

Ser Arg Val Asn Ser Asp Gly Arg Ile Thr Asn Phe Ala Asp Ser Val
50                  55                  60

Met Gly Arg Phe Thr Met Ser Arg Asp Asn Ala Lys Ser Thr Val Tyr
65                  70                  75                  80

Leu Gln Met Asn Ser Leu Arg Ala Glu Asp Thr Ala Met Tyr Tyr Cys
                85                  90                  95

Ser Arg Gly Gly Tyr Thr Gly Tyr Pro Glu Gly His Trp Gly Gln Gly
            100                 105                 110

Thr Leu Val Thr Val Ser
            115

<210> SEQ ID NO 25
<211> LENGTH: 23
<212> TYPE: PRT
<213> ORGANISM: Pan troglodytes

<400> SEQUENCE: 25

Glu Leu Gln Met Thr Gln Ser Pro Ser Ser Leu Ser Ala Ala Val Gly
1               5                   10                  15

Asp Ser Val Thr Ile Thr Cys
            20

<210> SEQ ID NO 26
```

```
<210> SEQ ID NO 26
<211> LENGTH: 11
<212> TYPE: PRT
<213> ORGANISM: Pan troglodytes

<400> SEQUENCE: 26

Arg Ala Ser Gln Gly Ile Ser Ile His Leu Ala
1               5                   10

<210> SEQ ID NO 27
<211> LENGTH: 15
<212> TYPE: PRT
<213> ORGANISM: Pan troglodytes

<400> SEQUENCE: 27

Trp Tyr Gln Gln Lys Pro Gly Lys Val Pro Asn Leu Leu Ile Tyr
1               5                   10                  15

<210> SEQ ID NO 28
<211> LENGTH: 7
<212> TYPE: PRT
<213> ORGANISM: Pan troglodytes

<400> SEQUENCE: 28

Ala Ala Ser Thr Leu Gln Ser
1               5

<210> SEQ ID NO 29
<211> LENGTH: 32
<212> TYPE: PRT
<213> ORGANISM: Pan troglodytes

<400> SEQUENCE: 29

Gly Val Pro Ser Arg Phe Ser Gly Ser Gly Ser Gly Thr Asp Phe Thr
1               5                   10                  15

Leu Thr Ile Asn Ser Leu Gln Pro Glu Val Phe Ala Thr Tyr Tyr Cys
            20                  25                  30

<210> SEQ ID NO 30
<211> LENGTH: 9
<212> TYPE: PRT
<213> ORGANISM: Pan troglodytes

<400> SEQUENCE: 30

Gln Lys Tyr Asp Ser Ala Pro Phe Thr
1               5

<210> SEQ ID NO 31
<211> LENGTH: 12
<212> TYPE: PRT
<213> ORGANISM: Pan troglodytes

<400> SEQUENCE: 31

Phe Gly Pro Gly Thr Lys Val Asp Ile Lys Arg Thr
1               5                   10

<210> SEQ ID NO 32
<211> LENGTH: 109
<212> TYPE: PRT
<213> ORGANISM: Pan troglodytes

<400> SEQUENCE: 32

Glu Leu Gln Met Thr Gln Ser Pro Ser Ser Leu Ser Ala Ala Val Gly
1               5                   10                  15

Asp Ser Val Thr Ile Thr Cys Arg Ala Ser Gln Gly Ile Ser Ile His
```

```
                20                  25                  30

Leu Ala Trp Tyr Gln Gln Lys Pro Gly Lys Val Pro Asn Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80

Glu Val Phe Ala Thr Tyr Tyr Cys Gln Lys Tyr Asp Ser Ala Pro Phe
                85                  90                  95

Thr Phe Gly Pro Gly Thr Lys Val Asp Ile Lys Arg Thr
            100                 105
```

<210> SEQ ID NO 33
<211> LENGTH: 30
<212> TYPE: PRT
<213> ORGANISM: Pan troglodytes

<400> SEQUENCE: 33

```
Glu Val Gln Leu Glu Gln Ser Gly Gly Gly Leu Ile Lys Pro Gly Gly
1               5                   10                  15

Ser Leu Arg Leu Ser Cys Ala Ala Ser Gly Phe Thr Phe Thr
            20                  25                  30
```

<210> SEQ ID NO 34
<211> LENGTH: 5
<212> TYPE: PRT
<213> ORGANISM: Pan troglodytes

<400> SEQUENCE: 34

```
Lys Tyr Val Met His
1               5
```

<210> SEQ ID NO 35
<211> LENGTH: 14
<212> TYPE: PRT
<213> ORGANISM: Pan troglodytes

<400> SEQUENCE: 35

```
Trp Val Arg Gln Ala Pro Glu Lys Gly Leu Gln Trp Val Ser
1               5                   10
```

<210> SEQ ID NO 36
<211> LENGTH: 10
<212> TYPE: PRT
<213> ORGANISM: Pan troglodytes

<400> SEQUENCE: 36

```
Ala Ile Gly Gly Ser Gly Gly Ser Ala Trp
1               5                   10
```

<210> SEQ ID NO 37
<211> LENGTH: 39
<212> TYPE: PRT
<213> ORGANISM: Pan troglodytes

<400> SEQUENCE: 37

```
Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
            20                  25                  30

Ala Val Tyr Tyr Cys Ala Arg
```

<210> SEQ ID NO 38
<211> LENGTH: 16
<212> TYPE: PRT
<213> ORGANISM: Pan troglodytes

<400> SEQUENCE: 38

Asp His Ala Arg Tyr Ser Gly Tyr Asn Ser Pro His Glu Val Asp Ser
1               5                   10                  15

<210> SEQ ID NO 39
<211> LENGTH: 10
<212> TYPE: PRT
<213> ORGANISM: Pan troglodytes

<400> SEQUENCE: 39

Trp Gly Gln Gly Thr Leu Val Ala Val Ser
1               5                   10

<210> SEQ ID NO 40
<211> LENGTH: 124
<212> TYPE: PRT
<213> ORGANISM: Pan troglodytes

<400> SEQUENCE: 40

Glu Val Gln Leu Glu Gln Ser Gly Gly Leu Ile Lys Pro Gly Gly
1               5                   10                  15

Ser Leu Arg Leu Ser Cys Ala Ala Ser Gly Phe Thr Phe Thr Lys Tyr
                20                  25                  30

Val Met His Trp Val Arg Gln Ala Pro Glu Lys Gly Leu Gln Trp Val
            35                  40                  45

Ser Ala Ile Gly Gly Ser Gly Ser Ala Trp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Ala Arg Tyr Ser Gly Tyr Asn Ser Pro His Glu Val
            100                 105                 110

Asp Ser Trp Gly Gln Gly Thr Leu Val Ala Val Ser
        115                 120

<210> SEQ ID NO 41
<211> LENGTH: 23
<212> TYPE: PRT
<213> ORGANISM: Pan troglodytes

<400> SEQUENCE: 41

Glu Leu Glu Leu Thr Gln Ser Pro Ser Ser Leu Ser Ala Ser Val Gly
1               5                   10                  15

Asp Arg Val Thr Ile Thr Cys
            20

<210> SEQ ID NO 42
<211> LENGTH: 11
<212> TYPE: PRT
<213> ORGANISM: Pan troglodytes

<400> SEQUENCE: 42

Arg Ala Ser Gln Gly Ile Ser Asn Tyr Leu Ala

-continued

```
1               5                   10
```

<210> SEQ ID NO 43
<211> LENGTH: 15
<212> TYPE: PRT
<213> ORGANISM: Pan troglodytes

<400> SEQUENCE: 43

```
Trp Tyr Gln Gln Lys Pro Gly Lys Val Pro Lys Leu Leu Ile Tyr
1               5                   10                  15
```

<210> SEQ ID NO 44
<211> LENGTH: 7
<212> TYPE: PRT
<213> ORGANISM: Pan troglodytes

<400> SEQUENCE: 44

```
Ala Ala Ser Thr Leu Gln Ser
1               5
```

<210> SEQ ID NO 45
<211> LENGTH: 32
<212> TYPE: PRT
<213> ORGANISM: Pan troglodytes

<400> SEQUENCE: 45

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
                20                  25                  30
```

<210> SEQ ID NO 46
<211> LENGTH: 9
<212> TYPE: PRT
<213> ORGANISM: Pan troglodytes

<400> SEQUENCE: 46

```
Gln Lys Tyr Asn Ser Ala Pro Leu Thr
1               5
```

<210> SEQ ID NO 47
<211> LENGTH: 12
<212> TYPE: PRT
<213> ORGANISM: Pan troglodytes

<400> SEQUENCE: 47

```
Phe Gly Gly Gly Thr Lys Val Glu Ile Lys Arg Thr
1               5                   10
```

<210> SEQ ID NO 48
<211> LENGTH: 109
<212> TYPE: PRT
<213> ORGANISM: Pan troglodytes

<400> SEQUENCE: 48

```
Glu Leu Glu Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys Arg Thr
            100                 105
```

<210> SEQ ID NO 49
<211> LENGTH: 30
<212> TYPE: PRT
<213> ORGANISM: Pan troglodytes

<400> SEQUENCE: 49

```
Glu Val Gln Leu Glu Glu Ser Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 50
<211> LENGTH: 5
<212> TYPE: PRT
<213> ORGANISM: Pan troglodytes

<400> SEQUENCE: 50

```
His Tyr Val Met Tyr
1               5
```

<210> SEQ ID NO 51
<211> LENGTH: 14
<212> TYPE: PRT
<213> ORGANISM: Pan troglodytes

<400> SEQUENCE: 51

```
Trp Val Arg Gln Ala Pro Glu Lys Gly Leu Glu Trp Val Ser
1               5                   10
```

<210> SEQ ID NO 52
<211> LENGTH: 10
<212> TYPE: PRT
<213> ORGANISM: Pan troglodytes

<400> SEQUENCE: 52

```
Thr Ile Ser Gly Ser Gly Ser Ser Thr Trp
1               5                   10
```

<210> SEQ ID NO 53
<211> LENGTH: 39
<212> TYPE: PRT
<213> ORGANISM: Pan troglodytes

<400> SEQUENCE: 53

```
Tyr Pro Asp Ser Val Lys Gly Arg Phe Thr Val Ser Arg Asp Asn Ser
1               5                   10                  15

Lys Asn Thr Leu Tyr Leu Gln Met Asn Ser Leu Arg Gly Asp Asp Thr
                20                  25                  30

Ala Val Tyr Tyr Cys Ala Arg
            35
```

<210> SEQ ID NO 54
<211> LENGTH: 7
<212> TYPE: PRT
<213> ORGANISM: Pan troglodytes

<400> SEQUENCE: 54

Leu Gln Gly Gln Leu Val Tyr
1               5

<210> SEQ ID NO 55
<211> LENGTH: 10
<212> TYPE: PRT
<213> ORGANISM: Pan troglodytes

<400> SEQUENCE: 55

Trp Gly Leu Gly Thr Leu Val Thr Val Ser
1               5                   10

<210> SEQ ID NO 56
<211> LENGTH: 115
<212> TYPE: PRT
<213> ORGANISM: Pan troglodytes

<400> SEQUENCE: 56

Glu Val Gln Leu Glu Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Val Met Tyr Trp Val Arg Gln Ala Pro Glu Lys Gly Leu Glu Trp Val
        35                  40                  45

Ser Thr Ile Ser Gly Ser Gly Ser Ser Thr Trp Tyr Pro Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Gly Asp Asp Thr Ala Val Tyr Tyr Cys
                85                  90                  95

Ala Arg Leu Gln Gly Gln Leu Val Tyr Trp Gly Leu Gly Thr Leu Val
            100                 105                 110

Thr Val Ser
        115

<210> SEQ ID NO 57
<211> LENGTH: 23
<212> TYPE: PRT
<213> ORGANISM: Pan troglodytes

<400> SEQUENCE: 57

Glu Leu Gln Met Thr Gln Ser Pro Ser Thr Leu Ser Ala Ser Val Gly
1               5                   10                  15

Asp Arg Val Thr Ile Thr Cys
            20

<210> SEQ ID NO 58
<211> LENGTH: 11
<212> TYPE: PRT
<213> ORGANISM: Pan troglodytes

<400> SEQUENCE: 58

Arg Ala Ser Gln Gly Ile Ser Ser Trp Leu Ala
1               5                   10

<210> SEQ ID NO 59
<211> LENGTH: 15
<212> TYPE: PRT
<213> ORGANISM: Pan troglodytes

<400> SEQUENCE: 59

Trp Tyr Gln Gln Lys Pro Gly Arg Ala Pro Lys Leu Leu Ile Tyr
1               5                   10                  15

<210> SEQ ID NO 60
<211> LENGTH: 7
<212> TYPE: PRT
<213> ORGANISM: Pan troglodytes

<400> SEQUENCE: 60

Lys Ser Ser Thr Leu Glu Ser
1               5

<210> SEQ ID NO 61
<211> LENGTH: 32
<212> TYPE: PRT
<213> ORGANISM: Pan troglodytes

<400> SEQUENCE: 61

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Phe Cys
            20                  25                  30

<210> SEQ ID NO 62
<211> LENGTH: 10
<212> TYPE: PRT
<213> ORGANISM: Pan troglodytes

<400> SEQUENCE: 62

Gln Gln Tyr Ser Ser Asn Pro Pro Leu Thr
1               5                   10

<210> SEQ ID NO 63
<211> LENGTH: 12
<212> TYPE: PRT
<213> ORGANISM: Pan troglodytes

<400> SEQUENCE: 63

Phe Gly Gly Gly Thr Lys Val Glu Ile Lys Arg Thr
1               5                   10

<210> SEQ ID NO 64
<211> LENGTH: 110
<212> TYPE: PRT
<213> ORGANISM: Pan troglodytes

<400> SEQUENCE: 64

Glu Leu Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Leu Leu Ile
        35                  40                  45

Tyr Lys Ser Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Phe Cys Gln Gln Tyr Ser Ser Asn Pro Pro
                85                  90                  95

```
Leu Thr Phe Gly Gly Thr Lys Val Glu Ile Lys Arg Thr
            100                 105                 110
```

<210> SEQ ID NO 65
<211> LENGTH: 30
<212> TYPE: PRT
<213> ORGANISM: Pan troglodytes

<400> SEQUENCE: 65

```
Glu Val Gln Leu Val Glu Thr Gly Gly Ser Leu Val Gln Pro Gly Gly
1               5                   10                  15

Ser Leu Arg Leu Ser Cys Ala Ala Ser Gly Phe Ser Val Ser
            20                  25                  30
```

<210> SEQ ID NO 66
<211> LENGTH: 5
<212> TYPE: PRT
<213> ORGANISM: Pan troglodytes

<400> SEQUENCE: 66

```
Ile Tyr His Met Ser
1               5
```

<210> SEQ ID NO 67
<211> LENGTH: 14
<212> TYPE: PRT
<213> ORGANISM: Pan troglodytes

<400> SEQUENCE: 67

```
Trp Val Arg Gln Ala Pro Gly Lys Gly Leu Glu Trp Val Ser
1               5                   10
```

<210> SEQ ID NO 68
<211> LENGTH: 9
<212> TYPE: PRT
<213> ORGANISM: Pan troglodytes

<400> SEQUENCE: 68

```
Leu Leu Tyr Ser Gly Gly Ser Thr Tyr
1               5
```

<210> SEQ ID NO 69
<211> LENGTH: 39
<212> TYPE: PRT
<213> ORGANISM: Pan troglodytes

<400> SEQUENCE: 69

```
Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
            20                  25                  30

Ala Val Tyr Tyr Cys Ala Arg
        35
```

<210> SEQ ID NO 70
<211> LENGTH: 22
<212> TYPE: PRT
<213> ORGANISM: Pan troglodytes

<400> SEQUENCE: 70

```
Asp Tyr Ser Gly Ser Trp Val Gly Asp Glu Ala Arg Ser Tyr Tyr Tyr
1               5                   10                  15

Tyr Tyr Tyr Met Asp Val
```

<210> SEQ ID NO 71
<211> LENGTH: 10
<212> TYPE: PRT
<213> ORGANISM: Pan troglodytes

<400> SEQUENCE: 71

Trp Gly Lys Gly Thr Thr Val Thr Val Ser
1               5                   10

<210> SEQ ID NO 72
<211> LENGTH: 129
<212> TYPE: PRT
<213> ORGANISM: Pan troglodytes

<400> SEQUENCE: 72

Glu Val Gln Leu Val Glu Thr Gly Gly Ser Leu Val Gln Pro Gly Gly
1               5                   10                  15

Ser Leu Arg Leu Ser Cys Ala Ala Ser Gly Phe Ser Val Ser Ile Tyr
            20                  25                  30

His Met Ser Trp Val Arg Gln Ala Pro Gly Lys Gly Leu Glu Trp Val
        35                  40                  45

Ser Leu Leu Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Ser Gly Ser Trp Val Gly Asp Glu Ala Arg Ser Tyr Tyr
            100                 105                 110

Tyr Tyr Tyr Tyr Met Asp Val Trp Gly Lys Gly Thr Thr Val Thr Val
        115                 120                 125

Ser

<210> SEQ ID NO 73
<211> LENGTH: 23
<212> TYPE: PRT
<213> ORGANISM: Pan troglodytes

<400> SEQUENCE: 73

Glu Leu Gln Val Thr Gln Ser Pro Ser Ser Leu Ser Ala Ser Val Gly
1               5                   10                  15

Asp Arg Val Thr Ile Thr Cys
            20

<210> SEQ ID NO 74
<211> LENGTH: 11
<212> TYPE: PRT
<213> ORGANISM: Pan troglodytes

<400> SEQUENCE: 74

Gln Ala Ser Gln Asp Ile Ser Tyr Tyr Leu Asn
1               5                   10

<210> SEQ ID NO 75
<211> LENGTH: 15
<212> TYPE: PRT
<213> ORGANISM: Pan troglodytes

<400> SEQUENCE: 75

Trp Tyr Gln Gln Arg Pro Gly Lys Val Pro Lys Leu Leu Ile Tyr
1               5                   10                  15

<210> SEQ ID NO 76
<211> LENGTH: 7
<212> TYPE: PRT
<213> ORGANISM: Pan troglodytes

<400> SEQUENCE: 76

Ser Ala Ser Tyr Leu His Ser
1               5

<210> SEQ ID NO 77
<211> LENGTH: 32
<212> TYPE: PRT
<213> ORGANISM: Pan troglodytes

<400> SEQUENCE: 77

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 78
<211> LENGTH: 9
<212> TYPE: PRT
<213> ORGANISM: Pan troglodytes

<400> SEQUENCE: 78

Gln Arg Thr Tyr Asn Ala Pro Tyr Thr
1               5

<210> SEQ ID NO 79
<211> LENGTH: 12
<212> TYPE: PRT
<213> ORGANISM: Pan troglodytes

<400> SEQUENCE: 79

Phe Gly Gln Gly Thr Lys Val Glu Ile Lys Arg Thr
1               5                   10

<210> SEQ ID NO 80
<211> LENGTH: 109
<212> TYPE: PRT
<213> ORGANISM: Pan troglodytes

<400> SEQUENCE: 80

Glu Leu Gln Val Thr Gln Ser Pro Ser Ser Leu Ser Ala Ser Val Gly
1               5                   10                  15

Asp Arg Val Thr Ile Thr Cys Gln Ala Ser Gln Asp Ile Ser Tyr Tyr
            20                  25                  30

Leu Asn Trp Tyr Gln Gln Arg Pro Gly Lys Val Pro Lys Leu Leu Ile
        35                  40                  45

Tyr Ser Ala Ser Tyr Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Thr Tyr Asn Ala Pro Tyr
                85                  90                  95

Thr Phe Gly Gln Gly Thr Lys Val Glu Ile Lys Arg Thr
            100                 105

<210> SEQ ID NO 81
<211> LENGTH: 30
<212> TYPE: PRT
<213> ORGANISM: Pan troglodytes

<400> SEQUENCE: 81

Glu Val Gln Leu Glu Glu Ser Gly Gly Val Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 82
<211> LENGTH: 5
<212> TYPE: PRT
<213> ORGANISM: Pan troglodytes

<400> SEQUENCE: 82

Ser His Ala Met His
1               5

<210> SEQ ID NO 83
<211> LENGTH: 13
<212> TYPE: PRT
<213> ORGANISM: Pan troglodytes

<400> SEQUENCE: 83

Trp Val Arg Gln Ala Pro Gly Lys Gly Leu Glu Trp Val
1               5                   10

<210> SEQ ID NO 84
<211> LENGTH: 10
<212> TYPE: PRT
<213> ORGANISM: Pan troglodytes

<400> SEQUENCE: 84

Ala Ile Ile Asn Ser Gly His Arg Ala Asp
1               5                   10

<210> SEQ ID NO 85
<211> LENGTH: 39
<212> TYPE: PRT
<213> ORGANISM: Pan troglodytes

<400> SEQUENCE: 85

Tyr Ala Asp Ser Val Lys Asp Arg Phe Thr Ile Ser Arg Asp Asn Ser
1               5                   10                  15

Lys Asn Thr Leu Tyr Leu Gln Met Asp Ser Leu Arg Pro Glu Asp Thr
            20                  25                  30

Ala Phe Tyr Tyr Cys Ala Arg
        35

<210> SEQ ID NO 86
<211> LENGTH: 9
<212> TYPE: PRT
<213> ORGANISM: Pan troglodytes

<400> SEQUENCE: 86

Glu Gly Asp Gln Gln Asp Val Ala Asp
1               5

<210> SEQ ID NO 87
<211> LENGTH: 14

-continued

<210> SEQ ID NO 87 (continued)
<212> TYPE: PRT
<213> ORGANISM: Pan troglodytes

<400> SEQUENCE: 87

Trp Gly Gln Gly Thr Leu Val Thr Val Ser Ser Ala Ser Thr
1               5                   10

<210> SEQ ID NO 88
<211> LENGTH: 106
<212> TYPE: PRT
<213> ORGANISM: Pan troglodytes

<400> SEQUENCE: 88

Glu Val Gln Leu Glu Ser Gly Gly Val Leu Val Lys Pro Gly Gly
1               5                   10                  15

Ser Leu Arg Leu Ser Cys Ala Ala Ser Gly Phe Thr Phe Ser Ser His
                20                  25                  30

Ala Met His Trp Val Arg Gln Ala Pro Gly Lys Gly Leu Glu Trp Val
            35                  40                  45

Ala Ile Ile Asn Ser Gly His Arg Ala Asp Tyr Ala Asp Ser Val Lys
        50                  55                  60

Asp Arg Phe Thr Ile Ser Arg Asp Asn Ser Lys Asn Thr Leu Tyr Leu
65                  70                  75                  80

Gln Met Asp Ser Leu Arg Pro Glu Asp Thr Ala Phe Tyr Tyr Cys Ala
                85                  90                  95

Arg Glu Gly Asp Gln Gln Asp Val Ala Asp
            100                 105

<210> SEQ ID NO 89
<211> LENGTH: 21
<212> TYPE: PRT
<213> ORGANISM: Pan troglodytes

<400> SEQUENCE: 89

Glu Leu Thr Gln Ser Pro Ser Thr Leu Ser Ala Ser Val Gly Asp Arg
1               5                   10                  15

Val Thr Ile Thr Cys
            20

<210> SEQ ID NO 90
<211> LENGTH: 11
<212> TYPE: PRT
<213> ORGANISM: Pan troglodytes

<400> SEQUENCE: 90

Arg Ala Ser Glu Asp Ile Met Ser Tyr Leu Ala
1               5                   10

<210> SEQ ID NO 91
<211> LENGTH: 15
<212> TYPE: PRT
<213> ORGANISM: Pan troglodytes

<400> SEQUENCE: 91

Trp Tyr Gln Gln Lys Pro Ala Lys Ala Pro Arg Leu Leu Ile Tyr
1               5                   10                  15

<210> SEQ ID NO 92
<211> LENGTH: 7
<212> TYPE: PRT
<213> ORGANISM: Pan troglodytes -continued

<400> SEQUENCE: 92

Tyr Ala Ser Ser Leu Gln Ser
1               5

<210> SEQ ID NO 93
<211> LENGTH: 32
<212> TYPE: PRT
<213> ORGANISM: Pan troglodytes

<400> SEQUENCE: 93

Gly Val Pro Ser Arg Phe Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 94
<211> LENGTH: 9
<212> TYPE: PRT
<213> ORGANISM: Pan troglodytes

<400> SEQUENCE: 94

Gln Gln Leu His Thr Phe Pro Ile Thr
1               5

<210> SEQ ID NO 95
<211> LENGTH: 12
<212> TYPE: PRT
<213> ORGANISM: Pan troglodytes

<400> SEQUENCE: 95

Phe Gly Pro Gly Thr Arg Leu Asp Ile Lys Arg Thr
1               5                   10

<210> SEQ ID NO 96
<211> LENGTH: 107
<212> TYPE: PRT
<213> ORGANISM: Pan troglodytes

<400> SEQUENCE: 96

Glu Leu Thr Gln Ser Pro Ser Thr Leu Ser Ala Ser Val Gly Asp Arg
1               5                   10                  15

Val Thr Ile Thr Cys Arg Ala Ser Glu Asp Ile Met Ser Tyr Leu Ala
            20                  25                  30

Trp Tyr Gln Gln Lys Pro Ala Lys Ala Pro Arg Leu Leu Ile Tyr Tyr
        35                  40                  45

Ala Ser Ser Leu Gln Ser Gly Val Pro Ser Arg Phe Ser Gly Ser Gly
    50                  55                  60

Ser Gly Thr Glu Phe Thr Leu Thr Ile Ser Ser Leu Gln Pro Glu Asp
65                  70                  75                  80

Phe Ala Thr Tyr Tyr Cys Gln Gln Leu His Thr Phe Pro Ile Thr Phe
                85                  90                  95

Gly Pro Gly Thr Arg Leu Asp Ile Lys Arg Thr
            100                 105

<210> SEQ ID NO 97
<211> LENGTH: 30
<212> TYPE: PRT
<213> ORGANISM: Pan troglodytes

<400> SEQUENCE: 97

Glu Val Gln Leu Glu Gln Ser Gly Gly Gly Leu Val Lys Pro Gly Gly

```
1               5                   10                  15
Ser Leu Arg Leu Ser Cys Ala Gly Ser Gly Phe Ser Phe Ser
        20                  25                  30
```

<210> SEQ ID NO 98
<211> LENGTH: 5
<212> TYPE: PRT
<213> ORGANISM: Pan troglodytes

<400> SEQUENCE: 98

```
Ala His Thr Ile Asn
1               5
```

<210> SEQ ID NO 99
<211> LENGTH: 13
<212> TYPE: PRT
<213> ORGANISM: Pan troglodytes

<400> SEQUENCE: 99

```
Trp Val Arg Gln Ala Pro Gly Lys Gly Leu Glu Trp Val
1               5                   10
```

<210> SEQ ID NO 100
<211> LENGTH: 13
<212> TYPE: PRT
<213> ORGANISM: Pan troglodytes

<400> SEQUENCE: 100

```
Gly Phe Ile Arg Ser Gln Ala Gln Gly Gly Thr Arg Glu
1               5                   10
```

<210> SEQ ID NO 101
<211> LENGTH: 39
<212> TYPE: PRT
<213> ORGANISM: Pan troglodytes

<400> SEQUENCE: 101

```
Tyr Ala Ala Ser Val Lys Gly Arg Ile Ile Leu Ser Arg Asp Asp Ser
1               5                   10                  15

Glu Asn Ser Ala Tyr Leu Gln Met Asn Ser Leu Asn Thr Gly Asp Thr
        20                  25                  30

Ala Val Tyr Tyr Cys Ala Arg
        35
```

<210> SEQ ID NO 102
<211> LENGTH: 13
<212> TYPE: PRT
<213> ORGANISM: Pan troglodytes

<400> SEQUENCE: 102

```
Asp Ser Ser Arg Gly Tyr Tyr Ser Tyr Tyr Leu Asp Val
1               5                   10
```

<210> SEQ ID NO 103
<211> LENGTH: 14
<212> TYPE: PRT
<213> ORGANISM: Pan troglodytes

<400> SEQUENCE: 103

```
Trp Gly Lys Gly Thr Thr Val Thr Val Ser Ser Ala Ser Thr
1               5                   10
```

<210> SEQ ID NO 104

```
<211> LENGTH: 127
<212> TYPE: PRT
<213> ORGANISM: Pan troglodytes

<400> SEQUENCE: 104
```

Glu Val Gln Leu Glu Gln Ser Gly Gly Leu Val Lys Pro Gly Gly
1               5                   10                  15

Ser Leu Arg Leu Ser Cys Ala Gly Ser Gly Phe Ser Phe Ser Ala His
            20                  25                  30

Thr Ile Asn Trp Val Arg Gln Ala Pro Gly Lys Gly Leu Glu Trp Val
        35                  40                  45

Gly Phe Ile Arg Ser Gln Ala Gln Gly Gly Thr Arg Glu Tyr Ala Ala
    50                  55                  60

Ser Val Lys Gly Arg Ile Ile Leu Ser Arg Asp Asp Ser Glu Asn Ser
65                  70                  75                  80

Ala Tyr Leu Gln Met Asn Ser Leu Asn Thr Gly Asp Thr Ala Val Tyr
                85                  90                  95

Tyr Cys Ala Arg Asp Ser Ser Arg Gly Tyr Tyr Ser Tyr Tyr Leu Asp
            100                 105                 110

Val Trp Gly Lys Gly Thr Thr Val Thr Val Ser Ser Ala Ser Thr
            115                 120                 125

```
<210> SEQ ID NO 105
<211> LENGTH: 21
<212> TYPE: PRT
<213> ORGANISM: Pan troglodytes

<400> SEQUENCE: 105
```

Glu Leu Thr Gln Ser Pro Ser Leu Ser Ala Ser Val Gly Asp Arg
1               5                   10                  15

Val Thr Ile Thr Cys
            20

```
<210> SEQ ID NO 106
<211> LENGTH: 11
<212> TYPE: PRT
<213> ORGANISM: Pan troglodytes

<400> SEQUENCE: 106
```

Arg Ala Ser Gln Gly Ile Ser Asn Arg Leu Asn
1               5                   10

```
<210> SEQ ID NO 107
<211> LENGTH: 15
<212> TYPE: PRT
<213> ORGANISM: Pan troglodytes

<400> SEQUENCE: 107
```

Trp Tyr Gln Gln Lys Pro Gly Lys Ala Pro Lys Leu Leu Ile Tyr
1               5                   10                  15

```
<210> SEQ ID NO 108
<211> LENGTH: 7
<212> TYPE: PRT
<213> ORGANISM: Pan troglodytes

<400> SEQUENCE: 108
```

Asp Ala Ser Ser Leu Glu Ser
1               5

```
<210> SEQ ID NO 109
```

-continued

```
<211> LENGTH: 32
<212> TYPE: PRT
<213> ORGANISM: Pan troglodytes

<400> SEQUENCE: 109

Gly Val Pro Ser Arg Phe Ser Gly Ser Gly Ser Gly Thr Asp Phe Thr
1               5                   10                  15

Leu Thr Ile Ser Ser Gln Gln Pro Glu Asp Phe Ala Thr Tyr Tyr Cys
            20                  25                  30

<210> SEQ ID NO 110
<211> LENGTH: 9
<212> TYPE: PRT
<213> ORGANISM: Pan troglodytes

<400> SEQUENCE: 110

Gln Gln Phe Asn Ser Tyr Pro Leu Thr
1               5

<210> SEQ ID NO 111
<211> LENGTH: 12
<212> TYPE: PRT
<213> ORGANISM: Pan troglodytes

<400> SEQUENCE: 111

Phe Gly Gly Gly Thr Lys Val Glu Ile Lys Arg Thr
1               5                   10

<210> SEQ ID NO 112
<211> LENGTH: 107
<212> TYPE: PRT
<213> ORGANISM: Pan troglodytes

<400> SEQUENCE: 112

Glu Leu Thr Gln Ser Pro Ser Ser Leu Ser Ala Ser Val Gly Asp Arg
1               5                   10                  15

Val Thr Ile Thr Cys Arg Ala Ser Gln Gly Ile Ser Asn Arg Leu Asn
            20                  25                  30

Trp Tyr Gln Gln Lys Pro Gly Lys Ala Pro Lys Leu Leu Ile Tyr Asp
        35                  40                  45

Ala Ser Ser Leu Glu Ser Gly Val Pro Ser Arg Phe Ser Gly Ser Gly
    50                  55                  60

Ser Gly Thr Asp Phe Thr Leu Thr Ile Ser Ser Gln Gln Pro Glu Asp
65                  70                  75                  80

Phe Ala Thr Tyr Tyr Cys Gln Gln Phe Asn Ser Tyr Pro Leu Thr Phe
                85                  90                  95

Gly Gly Gly Thr Lys Val Glu Ile Lys Arg Thr
            100                 105

<210> SEQ ID NO 113
<211> LENGTH: 30
<212> TYPE: PRT
<213> ORGANISM: Pan troglodytes

<400> SEQUENCE: 113

Glu Val Gln Leu Glu Gln Ser Gly Ala Glu Val Lys Lys Pro Gly Ser
1               5                   10                  15

Ser Val Lys Val Ser Cys Lys Ile Ser Gly Gly Thr Phe Ser
            20                  25                  30

<210> SEQ ID NO 114
```

```
<211> LENGTH: 5
<212> TYPE: PRT
<213> ORGANISM: Pan troglodytes

<400> SEQUENCE: 114

Arg His Pro Ile Ser
1               5

<210> SEQ ID NO 115
<211> LENGTH: 13
<212> TYPE: PRT
<213> ORGANISM: Pan troglodytes

<400> SEQUENCE: 115

Trp Val Arg Gln Ala Pro Gly Gln Gly Leu Leu Trp Met
1               5                   10

<210> SEQ ID NO 116
<211> LENGTH: 11
<212> TYPE: PRT
<213> ORGANISM: Pan troglodytes

<400> SEQUENCE: 116

Gly Ala Ile Ile Leu Arg Ala Gly Thr Thr Lys
1               5                   10

<210> SEQ ID NO 117
<211> LENGTH: 39
<212> TYPE: PRT
<213> ORGANISM: Pan troglodytes

<400> SEQUENCE: 117

Tyr Glu Gln Arg Phe Gln Gly Arg Ile Thr Ile Thr Ala Asp Glu Ser
1               5                   10                  15

Thr Gly Thr Ala Tyr Met Glu Leu His Ser Leu Thr Ser Glu Asp Thr
            20                  25                  30

Gly Leu Tyr Phe Cys Ala Thr
        35

<210> SEQ ID NO 118
<211> LENGTH: 13
<212> TYPE: PRT
<213> ORGANISM: Pan troglodytes

<400> SEQUENCE: 118

Asp Arg Met Gly Thr Phe Asp Glu Leu Leu Phe Asp Ser
1               5                   10

<210> SEQ ID NO 119
<211> LENGTH: 14
<212> TYPE: PRT
<213> ORGANISM: Pan troglodytes

<400> SEQUENCE: 119

Trp Gly Gln Gly Thr Leu Val Thr Val Ser Ser Ala Ser Thr
1               5                   10

<210> SEQ ID NO 120
<211> LENGTH: 148
<212> TYPE: PRT
<213> ORGANISM: Pan troglodytes

<400> SEQUENCE: 120

Glu Val Gln Leu Glu Gln Ser Gly Ala Glu Val Lys Lys Pro Gly Ser
```

```
                1               5                   10                  15
        Ser Val Lys Val Ser Cys Lys Ile Ser Gly Gly Thr Phe Ser Arg His
                        20                  25                  30

Pro Ile Ser Trp Val Arg Gln Ala Pro Gly Gln Gly Leu Leu Trp Met
                        35                  40                  45

Gly Ala Ile Ile Leu Arg Ala Gly Thr Thr Lys Tyr Glu Gln Arg Phe
                    50                  55                  60

Gln Gly Arg Ile Thr Ile Thr Ala Asp Glu Ser Thr Gly Thr Ala Tyr
        65                  70                  75                  80

Met Glu Leu His Ser Leu Thr Ser Glu Asp Thr Gly Leu Tyr Phe Cys
                        85                  90                  95

Ala Thr Asp Arg Met Gly Thr Phe Asp Glu Leu Leu Phe Asp Ser Trp
                        100                 105                 110

Gly Gln Gly Thr Leu Val Thr Val Ser Ser Ala Ser Thr Glu Leu Gln
                        115                 120                 125

Met Thr Gln Ser Pro Ala Ser Leu Ser Ala Ser Val Gly Asp Arg Val
                    130                 135                 140

Thr Ile Thr Cys
        145

<210> SEQ ID NO 121
<211> LENGTH: 23
<212> TYPE: PRT
<213> ORGANISM: Pan troglodytes

<400> SEQUENCE: 121

Glu Leu Gln Met Thr Gln Ser Pro Ala Ser Leu Ser Ala Ser Val Gly
1               5                   10                  15

Asp Arg Val Thr Ile Thr Cys
                20

<210> SEQ ID NO 122
<211> LENGTH: 11
<212> TYPE: PRT
<213> ORGANISM: Pan troglodytes

<400> SEQUENCE: 122

Arg Ala Ser Gln Gly Ile Arg Asn Asn Leu Gly
1               5                   10

<210> SEQ ID NO 123
<211> LENGTH: 15
<212> TYPE: PRT
<213> ORGANISM: Pan troglodytes

<400> SEQUENCE: 123

Trp Tyr Gln Gln Lys Pro Gly Lys Pro Pro Lys Leu Leu Ile Tyr
1               5                   10                  15

<210> SEQ ID NO 124
<211> LENGTH: 7
<212> TYPE: PRT
<213> ORGANISM: Pan troglodytes

<400> SEQUENCE: 124

Ala Ala Ser Thr Leu Gln Ser
1               5

<210> SEQ ID NO 125
<211> LENGTH: 32
```

```
<212> TYPE: PRT
<213> ORGANISM: Pan troglodytes

<400> SEQUENCE: 125

Gly Val Pro Ser Arg Phe Ser Gly Ser Gly Ser Gly Thr Gly Phe Thr
1               5                   10                  15

Leu Thr Ile Ser Ser Leu Gln Pro Glu Asp Phe Ala Thr Tyr Tyr Cys
            20                  25                  30

<210> SEQ ID NO 126
<211> LENGTH: 9
<212> TYPE: PRT
<213> ORGANISM: Pan troglodytes

<400> SEQUENCE: 126

Leu Gln Asp Tyr Asp Phe Pro Leu Thr
1               5

<210> SEQ ID NO 127
<211> LENGTH: 12
<212> TYPE: PRT
<213> ORGANISM: Pan troglodytes

<400> SEQUENCE: 127

Phe Gly Gly Gly Thr Lys Val Glu Ile Lys Arg Thr
1               5                   10

<210> SEQ ID NO 128
<211> LENGTH: 109
<212> TYPE: PRT
<213> ORGANISM: Pan troglodytes

<400> SEQUENCE: 128

Glu Leu Gln Met Thr Gln Ser Pro Ala Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Gln Lys Pro Gly Lys Pro Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Leu Gln Asp Tyr Asp Phe Pro Leu
                85                  90                  95

Thr Phe Gly Gly Gly Thr Lys Val Glu Ile Lys Arg Thr
            100                 105

<210> SEQ ID NO 129
<211> LENGTH: 32
<212> TYPE: PRT
<213> ORGANISM: Pan troglodytes

<400> SEQUENCE: 129

Leu Glu Glu Val Gln Leu Val Glu Ser Gly Pro Gly Leu Val Lys Pro
1               5                   10                  15

Ser Glu Thr Leu Ser Leu Thr Cys Ala Val Ser Gly Ala Ser Ile Arg
            20                  25                  30

<210> SEQ ID NO 130
<211> LENGTH: 6
```

```
<212> TYPE: PRT
<213> ORGANISM: Pan troglodytes

<400> SEQUENCE: 130

Arg Ala Asn Trp Trp Gly
1               5

<210> SEQ ID NO 131
<211> LENGTH: 13
<212> TYPE: PRT
<213> ORGANISM: Pan troglodytes

<400> SEQUENCE: 131

Trp Ile Arg Gln Ala Pro Gly Lys Gly Leu Glu Trp Leu
1               5                   10

<210> SEQ ID NO 132
<211> LENGTH: 10
<212> TYPE: PRT
<213> ORGANISM: Pan troglodytes

<400> SEQUENCE: 132

Gly Ser Ile Phe Ile Asn Ala Gly Thr Ile
1               5                   10

<210> SEQ ID NO 133
<211> LENGTH: 39
<212> TYPE: PRT
<213> ORGANISM: Pan troglodytes

<400> SEQUENCE: 133

Tyr Asn Pro Ser Leu Thr Gly Arg Val Thr Val Ser Ala Asp Thr Ser
1               5                   10                  15

Lys Asn Leu Phe Ser Leu Lys Leu Gly Ser Val Thr Ala Ala Asp Thr
            20                  25                  30

Ala Val Tyr Tyr Cys Val Lys
        35

<210> SEQ ID NO 134
<211> LENGTH: 18
<212> TYPE: PRT
<213> ORGANISM: Pan troglodytes

<400> SEQUENCE: 134

Ser Tyr Gly Asp Gly Asp Asp Asn Tyr Asn Ser Phe Tyr Tyr Met
1               5                   10                  15

Asp Val

<210> SEQ ID NO 135
<211> LENGTH: 14
<212> TYPE: PRT
<213> ORGANISM: Pan troglodytes

<400> SEQUENCE: 135

Trp Gly Lys Gly Thr Ser Val Ile Val Ser Ser Ala Ser Thr
1               5                   10

<210> SEQ ID NO 136
<211> LENGTH: 132
<212> TYPE: PRT
<213> ORGANISM: Pan troglodytes

<400> SEQUENCE: 136
```

```
Leu Glu Glu Val Gln Leu Val Glu Ser Gly Pro Gly Leu Val Lys Pro
1               5                   10                  15

Ser Glu Thr Leu Ser Leu Thr Cys Ala Val Ser Gly Ala Ser Ile Arg
            20                  25                  30

Arg Ala Asn Trp Trp Gly Trp Ile Arg Gln Ala Pro Gly Lys Gly Leu
        35                  40                  45

Glu Trp Leu Gly Ser Ile Phe Ile Asn Ala Gly Thr Ile Tyr Asn Pro
    50                  55                  60

Ser Leu Thr Gly Arg Val Thr Val Ser Ala Asp Thr Ser Lys Asn Leu
65                  70                  75                  80

Phe Ser Leu Lys Leu Gly Ser Val Thr Ala Ala Asp Thr Ala Val Tyr
                85                  90                  95

Tyr Cys Val Lys Ser Tyr Gly Asp Gly Asp Asp Asn Tyr Asn Ser Phe
            100                 105                 110

Tyr Tyr Tyr Met Asp Val Trp Gly Lys Gly Thr Ser Val Ile Val Ser
            115                 120                 125

Ser Ala Ser Thr
            130

<210> SEQ ID NO 137
<211> LENGTH: 23
<212> TYPE: PRT
<213> ORGANISM: Pan troglodytes

<400> SEQUENCE: 137

Asp Val Val Met Thr Gln Ser Pro Ser Ser Leu Ser Ala Ser Val Gly
1               5                   10                  15

Asp Arg Val Thr Ile Thr Cys
            20

<210> SEQ ID NO 138
<211> LENGTH: 11
<212> TYPE: PRT
<213> ORGANISM: Pan troglodytes

<400> SEQUENCE: 138

Arg Ala Ser Gln Asp Ile Arg Asn Asn Leu Ala
1               5                   10

<210> SEQ ID NO 139
<211> LENGTH: 15
<212> TYPE: PRT
<213> ORGANISM: Pan troglodytes

<400> SEQUENCE: 139

Trp Tyr Gln His Lys Pro Gly Lys Ala Pro Lys Leu Leu Ile Tyr
1               5                   10                  15

<210> SEQ ID NO 140
<211> LENGTH: 7
<212> TYPE: PRT
<213> ORGANISM: Pan troglodytes

<400> SEQUENCE: 140

Tyr Ala Ser Lys Leu Gln Ser
1               5

<210> SEQ ID NO 141
<211> LENGTH: 32
<212> TYPE: PRT
<213> ORGANISM: Pan troglodytes
```

<400> SEQUENCE: 141

Gly Val Pro Leu Arg Phe Ser Gly Ser Gly Ser Gly Thr Asp Tyr Thr
1               5                   10                  15

Leu Phe Ile Ser Ser Leu Gln Pro Glu Asp Phe Ala Thr Tyr Tyr Cys
            20                  25                  30

<210> SEQ ID NO 142
<211> LENGTH: 10
<212> TYPE: PRT
<213> ORGANISM: Pan troglodytes

<400> SEQUENCE: 142

Gln Gln Tyr Lys Thr Asp Thr Pro Tyr Ser
1               5                   10

<210> SEQ ID NO 143
<211> LENGTH: 12
<212> TYPE: PRT
<213> ORGANISM: Pan troglodytes

<400> SEQUENCE: 143

Phe Gly Gln Gly Thr Lys Val Asp Ile Lys Arg Thr
1               5                   10

<210> SEQ ID NO 144
<211> LENGTH: 110
<212> TYPE: PRT
<213> ORGANISM: Pan troglodytes

<400> SEQUENCE: 144

Asp Val Val Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asn
            20                  25                  30

Leu Ala Trp Tyr Gln His Lys Pro Gly Lys Ala Pro Lys Leu Leu Ile
        35                  40                  45

Tyr Tyr Ala Ser Lys Leu Gln Ser Gly Val Pro Leu Arg Phe Ser Gly
50                  55                  60

Ser Gly Ser Gly Thr Asp Tyr Thr Leu Phe Ile Ser Ser Leu Gln Pro
65                  70                  75                  80

Glu Asp Phe Ala Thr Tyr Tyr Cys Gln Gln Tyr Lys Thr Asp Thr Pro
                85                  90                  95

Tyr Ser Phe Gly Gln Gly Thr Lys Val Asp Ile Lys Arg Thr
            100                 105                 110

<210> SEQ ID NO 145
<211> LENGTH: 14
<212> TYPE: DNA
<213> ORGANISM: Pan troglodytes

<400> SEQUENCE: 145
gggaacagac cacc                                                    14

<210> SEQ ID NO 146
<211> LENGTH: 375
<212> TYPE: DNA
<213> ORGANISM: Pan troglodytes

<400> SEQUENCE: 146
gaggtgcagc tcgagcagtc agggggctgag gtgaagaagc cggggtcttc agtgaaggtc    60

```
tcttgtaaga tttcgggagg caccttcagc agacatccta tcagctgggt ccgacaggcc    120
cctggacaag ggcttctatg gatgggagcg atcatcctta gggctggaac gacaaagtac    180
gagcagaggt ttcagggcag aatcacaatt accgcggacg aatccacggg cacagcctac    240
atggaactcc acagcctgac ttctgaggac acgggcctct atttctgtgc gacagatagg    300
atggggacgt tgacgaatt gctgtttgac tcctggggcc agggaaccct ggtcaccgtc     360
tcgtccgcct ccacc                                                     375

<210> SEQ ID NO 147
<211> LENGTH: 360
<212> TYPE: DNA
<213> ORGANISM: Pan troglodytes

<400> SEQUENCE: 147
gaggtgcagc tcgaggagtc tgggggagtc ttggtaaagc cggggggggtc cctaagactc    60 tcctgtgcag cctctggatt cacgttcagt agccatgcta tgcactgggt tcgccaggca    120
ccagggaagg gtctggagtg gtcgcaatc attaatagtg gtcatagagc agactatgca     180
gactccgtga aggacagatt caccatctcc agagacaatt ccaagaatac actgtatctt    240
caaatggaca gcctgagacc tgaggatacg gcttttttatt actgtgcgag agagggcgac    300
caacaagacg ttgctgactg gggccaggga accctggtca ccgtctcctc agcctccacc    360

<210> SEQ ID NO 148
<211> LENGTH: 381
<212> TYPE: DNA
<213> ORGANISM: Pan troglodytes

<400> SEQUENCE: 148
gaggtgcagc tcgagcagtc tgggggaggc ttggtaaagc ctgggggatc cctgaggctc     60
tcctgtgcag ggtctggatt cagcttcagt gcccacacaa ttaactgggt ccggcaggct    120
ccagggaagg ggctggagtg gtaggtttc atcagaagtc aggctcaggg tgggacaaga    180
gaatacgccg cgtctgtgaa aggcagaatt attctctcaa gagatgattc cgaaaacagt    240
gcctatctgc aaatgaacag cctgaatacc ggcgacacag ccgtgtatta ttgtgcaaga    300
gattctagtc gcggctatta ctcctactac ttggacgtct ggggcaaagg gaccacggtc    360
accgtctcct cagcctccac c                                              381

<210> SEQ ID NO 149
<211> LENGTH: 396
<212> TYPE: DNA
<213> ORGANISM: Pan troglodytes

<400> SEQUENCE: 149
ctcgaggagg tgcagctggt ggagtcgggc ccaggactgg tgaagccttc agagaccctg     60
tccctcacat cgctgtctc tggtgcctcc atcagcgtg ctaattggtg gggctggatc     120
cggcaggccc caggaaggg actggagtgg ctcggcagta tctttattaa tgcgggcacc    180
atttataacc cgtccctcac gggtcgagtc accgtctcag cggacacgtc caagaacctg    240
ttctccctga agctgggctc tgtgaccgcc gcggacacgg cagtctatta ctgtgtgaaa    300
tcctatggtg atggtgatga taattacaac agtttctact actacatgga cgtctggggc    360
aaagggacct cggtcatcgt ctcctcagcc tccacc                              396

<210> SEQ ID NO 150
```

```
<211> LENGTH: 326
<212> TYPE: DNA
<213> ORGANISM: Pan troglodytes

<400> SEQUENCE: 150
gagctccaga tgacccagtc tccagcctcc ctgtctgcat ctgtaggaga cagagtcacc      60
atcacttgcc gggcaagtca gggcatcaga aacaatttag gctggtatca gcagaaacca     120
gggaaacccc ctaagctcct gatctatgct gcatccactt tacaaagtgg ggtcccatca     180
aggttcagtg gcagtgggtc tggcacaggt ttcactctca ccatcagcag cctgcagcct     240
gaagattttg cgacttatta ctgtctacaa gattacgatt tcccgctcac tttcggtgga     300
gggaccaagg ttgagatcaa acgaac                                          326

<210> SEQ ID NO 151
<211> LENGTH: 321
<212> TYPE: DNA
<213> ORGANISM: Pan troglodytes

<400> SEQUENCE: 151
gagctcacgc agtctccatc gaccctgtct gcatctgtag ggacagagt caccatcact       60
tgccgggcca gtgaggacat tatgagttat ttagcctggt atcagcaaaa accagcaaaa     120
gcccccaggc tcctcatcta ttatgcatct agtttgcaaa gtggggtccc atcgagattc     180
agcggcagtg gatctgggac agaattcact ctcacaatca gcagcctgca gcctgaagat     240
tttgcaactt attactgtca gcagcttcat actttcccga tcaccttcgg cccagggacg     300
cgactggaca ttaaacgaac t                                               321

<210> SEQ ID NO 152
<211> LENGTH: 321
<212> TYPE: DNA
<213> ORGANISM: Pan troglodytes

<400> SEQUENCE: 152
gagctcacgc agtctccatc ctccctgtct gcatctgtag gagacagagt caccatcact      60
tgccgggcaa gtcagggcat tagcaataga ttaaattggt atcagcagaa accagggaaa     120
gctcctaagc tcctgatcta tgatgcctcc agtttggaaa gtggggtccc atcaaggttc     180
agcggcagtg gatctgggac agatttcact ctcaccatca gcagccagca gcctgaagat     240
tttgcaactt attactgtca acagtttaat agttacccgc tcactttcgg tggagggacc     300
aaggtggaga tcaaacgaac t                                               321

<210> SEQ ID NO 153
<211> LENGTH: 330
<212> TYPE: DNA
<213> ORGANISM: Pan troglodytes

<400> SEQUENCE: 153
gatgttgtga tgactcagtc tccatcctcc ctgtctgcat ctgtaggaga cagagtcacc      60
atcacttgcc gggccagtca ggacattagg aataatttag cctggtatca gcacaaacca     120
gggaaagccc ccaaactcct catctattat gcatccaaat tgcaaagtgg ggtcccatta     180
aggttcagcg gcagtggatc tgggacggat tacacgctat tcatcagcag cctgcagcct     240
gaagattttg caacttatta ctgtcaacag tataagactg atactccgta cagttttggc     300
cagggggacca aagtggatat caaacgtacg                                     330
```

```
<210> SEQ ID NO 154
<211> LENGTH: 351
<212> TYPE: DNA
<213> ORGANISM: Pan troglodytes

<400> SEQUENCE: 154
gaggtgcagc tcgaggagtc tgggggagac ttggtccagc ctgggggtc cctgacactc      60 tcctgtgcag cctctggttt caccttcagt agatattgga tgagctgggt ccgccaggct    120
ccggggaagg ggccggagtg ggtggccagc ataaagaaag atggaagtga gacattctat    180
gcggactctg tgaagggccg attcatcatc tccagagaca tcgccaagac ctcattgtat    240
ttgcaaatga acagcctgag agccgacgac acggctgtat attactgtct gcgggcctgg    300
tatagcagcg cctacgactt ctggggccag ggaaccctgg tcaccgtctc c             351

<210> SEQ ID NO 155
<211> LENGTH: 354
<212> TYPE: DNA
<213> ORGANISM: Pan troglodytes

<400> SEQUENCE: 155
gaggtgcagc tcgaggagtc tgggggaggc ctagttcagc ctgggggtc cctgagagtc     60 tcctgtgcag cctctggatt ccccttcaat ggttactgga tacactgggt ccgccaagct    120
ccagggaagg ggctggagtg ggtctcccgt gttaacagtg atggaaggat cacaaatttt    180
gcggactccg tgatgggccg attcaccatg tccagagaca cgccaagag cacggtgtat     240 ctgcaaatga acagcctgag agccgaggac acggctatgt attattgcag tagaggtgga    300
tatactggct acccagaagg ccactggggc cagggaaccc tggtcaccgt ctcc          354

<210> SEQ ID NO 156
<211> LENGTH: 372
<212> TYPE: DNA
<213> ORGANISM: Pan troglodytes

<400> SEQUENCE: 156
gaggtgcagc tcgagcagtc tgggggaggc ttgataaagc ctgggggttc cctgagactc     60
tcgtgtgcag cctctggatt caccttcact aagtatgtta tgcactgggt ccgccaggct    120
ccagagaagg ggctgcagtg ggtctcagct attggtggta gtggtggtag cgcgtggtat    180
gcagactctg tcaagggccg attcaccatc tccagagaca attccaagaa cacactgtat    240
ctacaaatga atagcctgag agccgaggac acggccgtct attactgtgc gagagatcac    300
gcccgatata gtggctacaa ttctccccat gaagtggact catggggcca gggaaccctg    360
gtcgccgtct cc                                                        372

<210> SEQ ID NO 157
<211> LENGTH: 345
<212> TYPE: DNA
<213> ORGANISM: Pan troglodytes

<400> SEQUENCE: 157
gaggtgcagc tcgaggagtc tgggggaggc ctggtaaagc ctgggggttc cctgagactc     60
tcgtgtgcag cctctggatt caccttcagt cattatgtta tgtattgggt ccgccaggct    120
ccagagaagg ggctggagtg gtctcaact attagtggta gcggtagtag cacgtggtat     180
ccagactctg tcaagggccg attcaccgtt tccagagaca attccaagaa cacattgtat    240
ctgcaaatga acagcctgag aggcgacgac acggccgtgt attactgtgc gagacttcag    300
```

```
gggcagctag tttactgggg cctgggaacc ctggtcaccg tctcc              345
```

```
<210> SEQ ID NO 158
<211> LENGTH: 402
<212> TYPE: DNA
<213> ORGANISM: Pan troglodytes

<400> SEQUENCE: 158
gaggtgcagc tcgagcaggt gcagctggtg gagactggag gaagcttggt ccagcctggg    60
gggtccctga gactctcctg tgcagcctct ggattcagcg tcagtatcta ccacatgagc   120
tgggtccgcc aggctccagg gaaggggctg gagtgggtct cacttcttta tagtggtggt   180
agcacatact acgcagactc cgtgaagggc cgattcacca tctccagaga caattccaag   240
aacacgctgt atctgcaaat gaacagcctg agagctgagg acacggctgt atattactgt   300
gcaagagatt atagcggcag ctgggtcggg gatgaagccc gctcttacta ctactactac   360
tacatggacg tctggggcaa ggggaccacg gtcaccgtct cc                      402
```

```
<210> SEQ ID NO 159
<211> LENGTH: 318
<212> TYPE: DNA
<213> ORGANISM: Pan troglodytes

<400> SEQUENCE: 159
gagctcaccc agtctccatc ctccctgtct gcatctgtag gagacagagt caccatcact    60
tgccgggcaa gtcagagcat tagcaactat ttgaattggt atcagcagaa gccagggaaa   120
gcccctaacc tcctgatcta ttatgcatcc actttgcaaa gtggggtccc atcaaggttc   180
agtggcagtg gatctgggac agatttcact ctcaccatca gcagtctgca acctgaggat   240
tttgcaactt attactgtca acatggttac ggtgcgatcg ccttcggcca agggacacga   300
ctggagatta aacgaact                                                 318
```

```
<210> SEQ ID NO 160
<211> LENGTH: 321
<212> TYPE: DNA
<213> ORGANISM: Pan troglodytes

<400> SEQUENCE: 160
gagctcaccc agtctccatc ctccctgtct gcatctgtag gagacagagt caccatcact    60
tgccgggcga gtcagggcat tagcaattat ttagcctggt atcagcagaa accagggaaa   120
gttcctaagc tcctgatcta tgctgcatcc actttgcaat caggggtccc atctcggttc   180
agtggcagtg gatctgggac agatttcact ctcaccatca gcagcctgca gcctgaagat   240
gttgcaactt attactgtca aaagtataac agtgcccctc tcactttcgg tggagggacc   300
aaggtggaga tcaaacgaac t                                             321
```

```
<210> SEQ ID NO 161
<211> LENGTH: 327
<212> TYPE: DNA
<213> ORGANISM: Pan troglodytes

<400> SEQUENCE: 161
gagctccaga tgacccagtc tccatcctcc ctgtctgcag ctgtaggaga cagcgtcacc    60
atcacttgcc gggcgagtca gggcattagc attcatttag cctggtatca gcaaaaacca   120
gggaaagttc ctaatctcct gatctatgct gcgtccactt gcaatcagg ggtcccatct   180
cggttcagtg gcagtggctc tggcacagat ttcactctca ccatcagcaa cctccagcct   240
```

```
gaggatgttg caacttatta ctgtcaaaag tatgacagtg ccccattcac tttcggccct      300
gggaccaaag tggatatcaa acgaact                                          327

<210> SEQ ID NO 162
<211> LENGTH: 330
<212> TYPE: DNA
<213> ORGANISM: Pan troglodytes

<400> SEQUENCE: 162
gagctccaga tgacccagtc tccttccacc ctgtccgcat ctgtaggaga cagagtcacc       60
atcacttgcc gggccagtca gggtattagt agctggttag cctggtatca gcagaaacca      120
gggagagccc ctaaactcct gatctataag tcatctactt tagaaagtgg ggtcccatca      180
agattcagcg gcagtggatc tgggacagag ttcactctca ctatcagcag cctgcagcct      240
gatgattttg caacttattt ctgccaacaa tatagcagta accctccact gactttcggt      300
ggagggacca aggtggagat caaacgaact                                       330

<210> SEQ ID NO 163
<211> LENGTH: 327
<212> TYPE: DNA
<213> ORGANISM: Pan troglodytes

<400> SEQUENCE: 163
gagctccagg tgacccagtc tccatcctcc ctgtctgcat ctgtaggaga cagagtcacc       60
atcacttgcc aggcgagtca ggacattagc tactatttaa attggtatca gcagagacca      120
gggaaagttc ctaagctcct tatctatagt gcatcctatt tgcattctgg agtcccgtct      180
cggttcagtg gcagtggatc tgggacagat ttcactctca ctatcagcag cctgcagcct      240
gaagatgttg caacttatta ctgtcaacgg acttacaatg ccccgtacac ttttggccag      300
gggaccaagg tggagatcaa acgtacg                                          327
```

MONOCLONAL ANTIBODIES THAT NEUTRALIZE A NOROVIRUS

CROSS REFERENCE TO RELATED APPLICATIONS

This is a divisional of U.S. patent application Ser. No. 14/767,274, filed Aug. 11, 2015, which is §371 U.S. national stage of International Application No. PCT/US2014/015809, filed Feb. 11, 2014, which was published in English under PCT Article 21(2), which in turn claims the benefit of U.S. Patent Application No. 61/763,879, filed Feb. 12, 2013. The prior applications are incorporated herein by reference in their entirety.

FIELD OF THE DISCLOSURE

This relates to the field of antibodies, specifically to antibodies that specifically bind a Norovirus polypeptide, such as a Norwalk virus polypeptide, and their use.

BACKGROUND

Noroviruses (NoVs) are a leading cause of epidemic gastroenteritis in both children and adults worldwide (Glass et al., 2009, J Clin Microbiol 31:2185-91). Outbreaks commonly occur in settings such as hospitals, nursing homes, cruise ships, university dormitories, and military barracks. Although NoV illnesses are generally self-limiting, increased morbidity and mortality have been reported among vulnerable populations such as infants, the elderly, and immunocompromised individuals (Norovirus activity—United States, 2006-2007, MMWR Morb Mortal Wkly Rep 56:842-6; Byce et al., 2005, Lancet 365:1147-52; Green et al., 1993; J Clin Microbiol 31:2185-9; Sakai et al., 2001, Japan. Pediatr Infect Dis J 20:849-53; Zintz et al., 2005, Japan. Pediatr Infect Dis J 20:849-53). It is estimated that NoV infection may account for up to 200,000 deaths per year in infants and young children of developing countries (Patel et al., 2008, Emerg Infect Dis 14:1224-31).

Currently, there are no vaccines or specific antiviral therapies available for the treatment of NoV infections, largely due to the unavailability of permissive cell-culture systems and animal disease models. Most information regarding host immunity to NoV infection has originated from human challenge studies and epidemiological investigations (Atmar et al., 2008, Emerg Infect Dis 14:1553-7; Dolin et al., 1972, Proc Soc Exp Biol Med 140:578-83; Dolin et al., 1971, J Infect Dis 123:307-12; Graham et al., 1994, J Infect Dis 170:34-43; Parrino et al., 1977, N Engl J Med 297:86-9; Wyatt et al., 1974, J Infect Dis 129:709-14). As a result, the immune correlates of protection are poorly understood. Success in expression of recombinant virus-like particles (rVLPs) that mimic the antigenic structure of authentic virions (Prasad et al., 1999, Science 286:287-90; Prasad et al., 1994, J Virol 68:5117-25) and identification of histo-blood group antigens (HBGA) as cellular binding ligands for NoV infection (Harrington, 2002, J Virol 76:12335-43; Hutson et al., 2002, J Infect Dis 185:1335-7; Lindesmith et al., 2003, Nat Med 9:548-53; Marionneau et al., 2002, Gastroenterology 122:1967-77) have facilitated efforts toward the development of prevention and treatment strategies (Atmar et al., 2011, N Engl J Med 365:2178-87; Chang et al., 2007, J Virol 81:12111-8; Feng and Jiang, 2007, Antimicrob Agents Chemother 51:324-31; Herbst-Kralovetz et al., 2010, Expert Rev Vaccines 9:299-307).

A need remains for agents that can be used to treat and/or diagnose a NoV infection, such as a Norwalk virus infection.

SUMMARY OF THE DISCLOSURE

Monoclonal antibodies are disclosed that specifically bind to a NoV. NoVs include Genogroup I and Genogroup II NoVs. NoVs include, for example, Norwalk virus (NV) and MD145-12. The monoclonal antibodies can specifically bind Genogroup I and Genogroup II NoVs. In specific non-limiting examples, the monoclonal antibodies specifically bind VP1. In additional embodiments the monoclonal antibodies specifically bind a NoV polypeptide with an equilibrium constant ($K_d$) of 1 nM or less.

In some embodiments, the antibody or antigen binding fragment includes a heavy chain variable domain and a light chain variable domain and specifically binds a NoV polypeptide, wherein
  (a) the HCDR1 comprises the amino acid sequence set forth as SEQ ID NO: 18, the HCDR2 comprises the amino acid sequence set forth as SEQ ID NO: 20, and/or the HCDR3 comprises the amino acid sequence set forth as SEQ ID NO: 22;
  (b) the HCDR1 comprises the amino acid sequence set forth as SEQ ID NO: 2, the HCDR2 comprises the amino acid sequence set forth as SEQ ID NO: 4, and/or the HCDR3 comprises the amino acid sequence set forth as SEQ ID NO: 6;
  (c) the HCDR1 comprises the amino acid sequence set forth as SEQ ID NO: 34, the HCDR2 comprises the amino acid sequence set forth as SEQ ID NO: 36, and/or the HCDR3 comprises the amino acid sequence set forth as SEQ ID NO: 38;
  (d) the HCDR1 comprises the amino acid sequence set forth as SEQ ID NO: 50, the HCDR2 comprises the amino acid sequence set forth as SEQ ID NO: 52, and/or the HCDR3 comprises the amino acid sequence set forth as SEQ ID NO: 54;
  (e) the HCDR1 comprises the amino acid sequence set forth as SEQ ID NO: 66, the HCDR2 comprises the amino acid sequence set forth as SEQ ID NO: 68, and/or the HCDR3 comprises the amino acid sequence set forth as SEQ ID NO: 70;
  (f) the HCDR1 comprises the amino acid sequence set forth as SEQ ID NO: 82, the HCDR2 comprises the amino acid sequence set forth as SEQ ID NO: 84, and/or the HCDR3 comprises the amino acid sequence set forth as SEQ ID NO: 86;
  (g) the HCDR1 comprises the amino acid sequence set forth as SEQ ID NO: 98, the HCDR2 comprises the amino acid sequence set forth as SEQ ID NO: 100, and/or the HCDR3 comprises the amino acid sequence set forth as SEQ ID NO: 102;
  (h) the HCDR1 comprises the amino acid sequence set forth as SEQ ID NO: 114, the HCDR2 comprises the amino acid sequence set forth as SEQ ID NO: 116, and/or the HCDR3 comprises the amino acid sequence set forth as SEQ ID NO: 118; or
  (i) the HCDR1 comprises the amino acid sequence set forth as SEQ ID NO: 130, the HCDR2 comprises the amino acid sequence set forth as SEQ ID NO: 132, and/or the HCDR3 comprises the amino acid sequence set forth as SEQ ID NO: 134.

In some embodiments, the monoclonal antibody is a chimpanzee monoclonal antibody. In some embodiments, the monoclonal antibody is humanized. In some embodiments, the monoclonal antibody is chimeric.

Some embodiments provide nucleic acids encoding these antibodies, expression vectors including the nucleic acids, and isolated host cells that express the nucleic acids.

In further embodiments, methods are also disclosed for detecting the presence of a NoV in a biological sample, such as Genogroup I and Genogroup II NoVs. These methods can detect a NoV infection, such as a NV infection or a MD145-12 infection in a subject. These methods include contacting a biological sample of interest with an antibody disclosed herein, or an antigen binding fragment, and detecting binding of the antibody to the biological sample.

In other embodiments, methods are disclosed for treating and/or preventing a NoV infection. The methods can be used to treat and or prevent an Genogroup I and Genogroup II NoV infection, such as a NV infection or an MD145-12 infection, in a subject. These methods include administering to the subject a therapeutically effective amount of an antibody disclosed herein or antigen binding fragment thereof, or a nucleic acid encoding the antibody or antigen binding fragment, thereby treating or preventing the infection. The method can reduce viral titer.

The foregoing and other features and advantages of the invention will become more apparent from the following detailed description of a several embodiments which proceeds with reference to the accompanying figures.

BRIEF DESCRIPTION OF THE FIGURES

FIG. 2. Deduced amino acid sequences of variable domains of heavy (A) and light (B) chains of chimpanzee/human anti-NV chimeric monoclonal antibodies (MAbs). Complementarity-determining regions (CDR1-3) shown in boxes and framework regions (FWR1-4) are assigned according to Kabat nomenclature (Wu, T. T. Kabat, E. A., 1970, J Exp Med 132(2):211-50). SEQ ID NOs: 1-7 are the CDR and FWR sequences of the heavy chain of B7. SEQ ID NO: 8 is the amino acid sequence of the VH of B7. SEQ ID NOs. 9-15 are the CDR and FWR sequences of the light chain of B7. SEQ ID NO: 16 is the amino acid sequence of the VL of B7. SEQ ID NOs: 17-23 are the CDR and FWR sequences of the heavy chain of D8. SEQ ID NO: 24 is the amino acid sequence of the VH of D8. SEQ ID NOs. 25-31 are the CDR and FWR sequences of the light chain of D8. SEQ ID NO: 32 is the amino acid sequence of the VL of D8. SEQ ID NOs: 33-39 are the CDR and FWR sequences of the heavy chain of E5. SEQ ID NO: 30 is the amino acid sequence of the VH of E5. SEQ ID NOs. 41-47 are the CDR and FWR sequences of the light chain of E5. SEQ ID NO: 144 is the amino acid sequence of the VL of E5. SEQ ID NOs: 49-55 are the CDR and FWR sequences of the heavy chain of G4. SEQ ID NO: 56 is the amino acid sequence of the VH of G4. SEQ ID NOs. 57-63 are the CDR and FWR sequences of the light chain of G4. SEQ ID NO: 64 is the amino acid sequence of the VL of G4. SEQ ID NOs: 65-71 are the CDR and FWR sequences of the heavy chain of F11. SEQ ID NO: 72 is the amino acid sequence of the VH of D4.

SEQ ID NOs. 73-79 are the CDR and FWR sequences of the light chain of F11. SEQ ID NO: 80 is the amino acid sequence of the VL of F11.

Relative to B7 sequence, substitutions are expressed as single letters denoting amino acids and identical residues are indicated by asterisks. Dashes denote the absence of corresponding residues relative to the longest sequence.

Figure 3A:
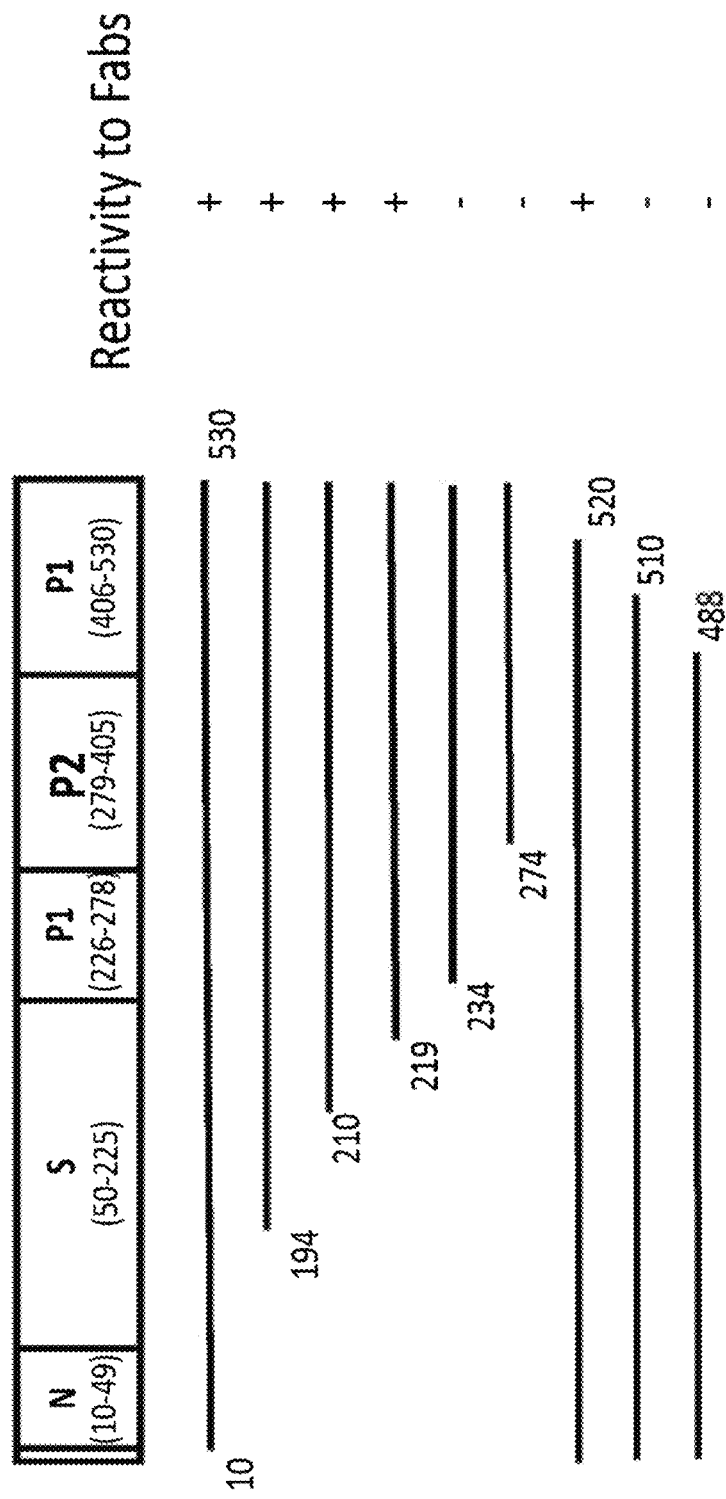

FIGS. 3A-3B. Epitope mapping. (A) Summary of epitope mapping of anti-NV Fab by radioimmunoprecipitation assay. $^{35}$S-labeled VP1 polypeptides, prepared in vitro, were incubated with anti-NV Fabs. The immune complexes were captured by protein G-coupled agarose beads and were separated by SDS-PAGE. The VP1 polypeptide was detected by exposing the dried gel to an x-ray film. Numbers denote the starting and ending amino acids. The polypeptides that reacted with Fab and, hence, were detected on an x-ray film were considered to be positive (+). (B) Flow cytometric analysis of yeast cell populations that were positive in Alex Fluor 488 (the VP1 expression fluorescence) and DyLight 649 (the Ab binding fluorescence). Cells were treated with either mouse MAb NV4 (A) or anti-NV chimp Fabs B7 (B), D8 (C), E5 (D), G4 (E). The percentage of double fluorescence-positive cells among AlexFluor 488-positive cells in each treatment was calculated and shown in the right upper corner.

FIGS. 4A-4C. Fine epitope mapping of Norwalk Fab G4. (A) Comparison of VP1 sequence between Norwalk and SW-2007 virus strains. A schematic diagram representing VP1 protein is shown in the upper panel. The locations of 530 amino acids are labeled and P1 and P2 subdomains are shown in hatched and filled boxes, respectively. The eight amino acid differences between Norwalk and SW-2007 strains, resulting in different reactivity to G4 are shown in the lower panel. (B) Immunofluorescence staining results from Vero cells transfected with different DNA constructs. Mutations on the VP1 from Norwalk were introduced by using specific primers and QuikChange Site-Directed Mutagenesis Kit (Stratagene, La Jolla, Calif.) following the manufacturer's recommendations. (C) The localization of the key mutation, G365N in Norwalk VP1 structure is colored in red. Two different blue tones are used to distinguish between the two VP1 monomers Amino acids responsible for the HBGA binding sites are colored in light pink and magenta.

Figure 5:
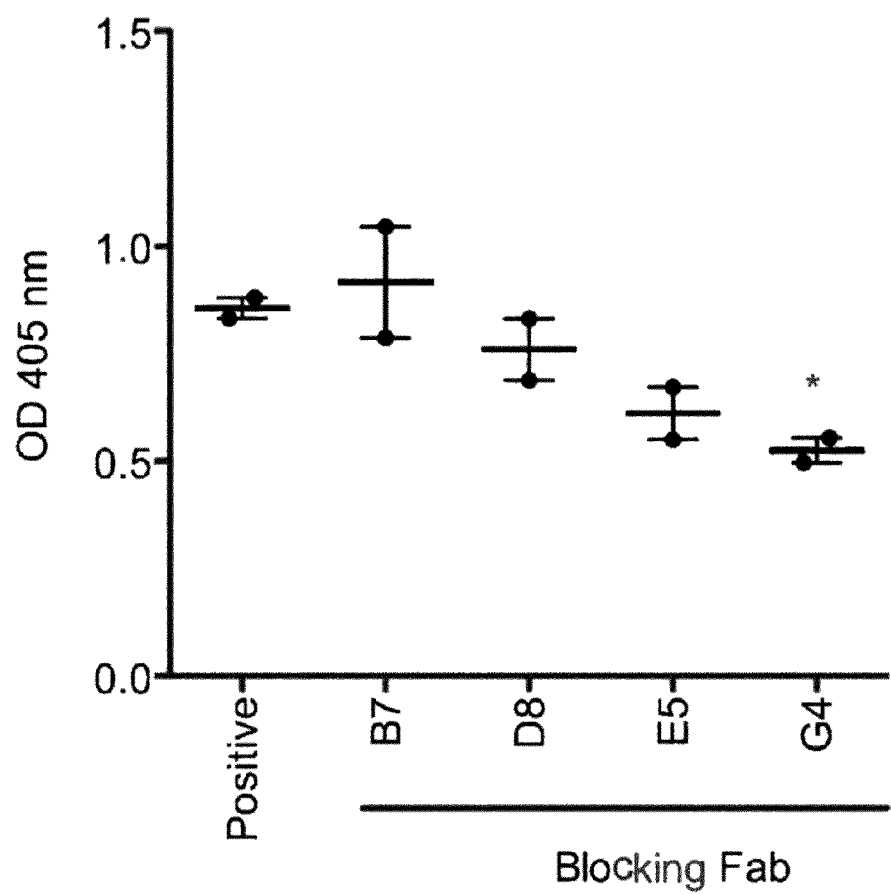

FIG. 5. Blocking of Norwalk hyperimmune sera by Fabs. Reactivity of hyperimmune serum (dilution $10^{-4}$) against Norwalk VLPs in the presence or absence of Fabs. Reactivity of hyperimmune serum with VLPs was measured as described in the Materials and Methods. Each dot represents the duplicate of a single experiment. Bars represent the OD average. Student's t test was used to compare differences of blocking assays with unblocked control. Statistics were assessed using GraphPad Prism 5.0. Statistical significance is denoted by * p≤0.05.

FIG. 6. Detection of HBGA-binding blocking activities of anti-NV IgGs. Blocking the HBGA binding by NV rVLPs in response to different concentrations of IgGs of clones E5, G4, F11, D8, and B7 by ELISA.

FIG. 7. Deduced amino acid sequences of variable domains of heavy (H) and light (L) chains of chimpanzee/human anti-NoV GII.4 MAbs. SEQ ID NOs: 81-87 are the CDR and FWR sequences of the heavy chain of C9. SEQ ID NO: 88 is the amino acid sequence of the VH of C9. SEQ ID NOs. 89-95 are the CDR and FWR sequences of the light chain of C9. SEQ ID NO: 96 is the amino acid sequence of the VL of C9. SEQ ID NOs: 97-103 are the CDR and FWR sequences of the heavy chain of G3. SEQ ID NO: 104 is the amino acid sequence of the VH of G3. SEQ ID NOs. 105-111 are the CDR and FWR sequences of the light chain of G3. SEQ ID NO: 112 is the amino acid sequence of the VL of G3. SEQ ID NOs: 113-119 are the CDR and FWR sequences of the heavy chain of B72. SEQ ID NO: 120 is the amino acid sequence of the VH of B72. SEQ ID NOs. 121-127 are the CDR and FWR sequences of the light chain of B72. SEQ ID NO: 128 is the amino acid sequence of the VL of B72. SEQ ID NOs: 129-135 are the CDR and FWR sequences of the heavy chain of D4. SEQ ID NO: 136 is the amino acid sequence of the VH of D4. SEQ ID NOs. 137-143 are the CDR and FWR sequences of the light chain of D4. SEQ ID NO: 144 is the amino acid sequence of the VL of D4.

Figure 8:
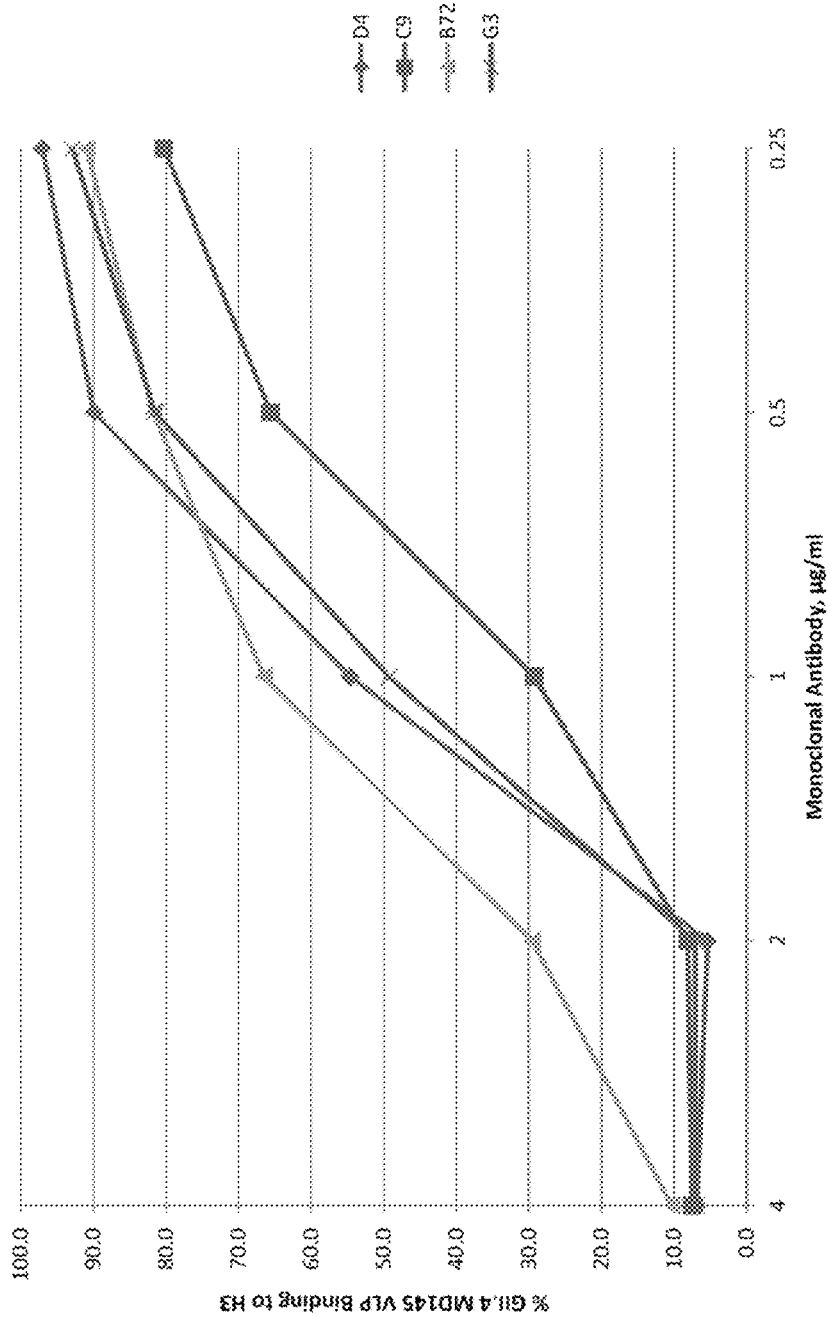

FIG. 8. Detection of HBGA-binding blocking activities of anti-NoV GII.4 IgGs.

FIG. 9. Table showing sequence identifiers for the CDRs, FWRs, and variable domains of exemplary antibodies. The antibody name is shown in the left column, followed by "H" for the heavy chain and "L" for the light chain.

FIGS. 10A-10D. Nucleotide sequences encoding heavy and light chains. FIG. 10A shows the nucleotide sequences of variable domain heavy chain of anti-NoV gII.4 antibodies. FIG. 10B shows the nucleotide sequence of variable domain light chain of anti-NoV gII.4 antibodies. FIG. 10C shows the nucleotide sequence of variable domain heavy chain of anti-NV antibodies. FIG. 10C shows the nucleotide sequence of variable domain light chain of anti-NV antibodies.

SEQUENCE LISTING

The nucleic and amino acid sequences listed are shown in the application using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. Sequences are shown for example, in FIGS. 2, 7, 9, 10A, 10B, 10C and 10D. The Sequence Listing is submitted as an ASCII text file 4239-89884-05_Sequence_Listing.txt, Nov. 22, 2016, 56.1 KB], which is incorporated by reference herein.

I. Antibodies that Specifically Bind a Genogroup I Virus, Such as a Norwalk Virus Polypeptide SEQ ID NO: 1 is the amino acid sequence of the HFWR1 of B7.
SEQ ID NO: 2 is the amino acid sequence of the HCDR1 of B7.
SEQ ID NO: 3 is the amino acid sequence of the HFWR2 of B7.
SEQ ID NO: 4 is the amino acid sequence of the HCDR2 of B7.
SEQ ID NO: 5 is the amino acid sequence of the HFWR3 of B7.
SEQ ID NO: 6 the amino acid sequence of the HCDR3 of B7.
SEQ ID NO: 7 is the amino acid sequence of the HFWR4 of B7.
SEQ ID NO: 8 is the amino acid sequence of the $V_H$ of B7.
SEQ ID NO: 9 is the amino acid sequence of the LFWR1 of B7.
SEQ ID NO: 10 is the amino acid sequence of the LCDR1 of B7.
SEQ ID NO: 11 is the amino acid sequence of the LFWR2 of B7.
SEQ ID NO: 12 is the amino acid sequence of the LCDR2 of B7.
SEQ ID NO: 13 is the amino acid sequence of the LFWR3 of B7.
SEQ ID NO: 14 the amino acid sequence of the LCDR3 of B7.
SEQ ID NO: 15 is the amino acid sequence of the LFWR4 of B7.
SEQ ID NO: 16 is the amino acid sequence of the $V_L$ of B7.
SEQ ID NO: 17 is the amino acid sequence of the HFWR1 D8.
SEQ ID NO: 18 is the amino acid sequence of the HCDR1 of D8.
SEQ ID NO: 19 is the amino acid sequence of the HFWR2 of D8.
SEQ ID NO: 20 is the amino acid sequence of the HCDR2 of D8.
SEQ ID NO: 21 is the amino acid sequence of the HFWR3 of D8.
SEQ ID NO: 22 the amino acid sequence of the HCDR3 of D8.
SEQ ID NO: 23 is the amino acid sequence of the HFWR4 of D8.
SEQ ID NO: 24 is the amino acid sequence of the $V_H$ of D8.
SEQ ID NO: 25 is the amino acid sequence of the LFWR1 of D8.
SEQ ID NO: 26 is the amino acid sequence of the LCDR1 of D8.
SEQ ID NO: 27 is the amino acid sequence of the LFWR2 of D8.
SEQ ID NO: 28 is the amino acid sequence of the LCDR2 of D8.
SEQ ID NO: 29 is the amino acid sequence of the LFWR3 of D8.
SEQ ID NO: 30 the amino acid sequence of the LCDR3 of D8.
SEQ ID NO: 31 is the amino acid sequence of the LFWR4 of D8.
SEQ ID NO: 32 is the amino acid sequence of the $V_L$ of D8.
SEQ ID NO: 33 is the amino acid sequence of the HFWR1 E5.
SEQ ID NO: 34 is the amino acid sequence of the HCDR1 of E5.
SEQ ID NO: 35 is the amino acid sequence of the HFWR2 of E5.
SEQ ID NO: 36 is the amino acid sequence of the HCDR2 of E5.
SEQ ID NO: 37 is the amino acid sequence of the HFWR3 of E5.
SEQ ID NO: 38 the amino acid sequence of the HCDR3 of E5.
SEQ ID NO: 39 is the amino acid sequence of the HFWR4 of E5.
SEQ ID NO: 40 is the amino acid sequence of the $V_H$ of E5.
SEQ ID NO: 41 is the amino acid sequence of the LFWR1 of E5.
SEQ ID NO: 42 is the amino acid sequence of the LCDR1 of E5.
SEQ ID NO: 43 is the amino acid sequence of the LFWR2 of E5.
SEQ ID NO: 44 is the amino acid sequence of the LCDR2 of E5.

SEQ ID NO: 45 is the amino acid sequence of the LFWR3 of E5.
SEQ ID NO: 46 the amino acid sequence of the LCDR3 of E5.
SEQ ID NO: 47 is the amino acid sequence of the LFWR4 of E5.
SEQ ID NO: 48 is the amino acid sequence of the $V_L$ of E5.
SEQ ID NO: 49 is the amino acid sequence of the HFWR1 of G4.
SEQ ID NO: 50 is the amino acid sequence of the HCDR1 of G4.
SEQ ID NO: 51 is the amino acid sequence of the HFWR2 of G4.
SEQ ID NO: 52 is the amino acid sequence of the HCDR2 of G4.
SEQ ID NO: 53 is the amino acid sequence of the HFWR3 of G4.
SEQ ID NO: 54 the amino acid sequence of the HCDR3 of G4.
SEQ ID NO: 55 is the amino acid sequence of the HFWR4 of G4.
SEQ ID NO: 56 is the amino acid sequence of the $V_H$ of G4.
SEQ ID NO: 57 is the amino acid sequence of the LFWR1 of G4.
SEQ ID NO: 58 is the amino acid sequence of the LCDR1 of G4.
SEQ ID NO: 59 is the amino acid sequence of the LFWR2 of G4.
SEQ ID NO: 60 is the amino acid sequence of the LCDR2 of G4.
SEQ ID NO: 61 is the amino acid sequence of the LFWR3 of G4.
SEQ ID NO: 62 the amino acid sequence of the LCDR3 of G4.
SEQ ID NO: 63 is the amino acid sequence of the LFWR4 of G4.
SEQ ID NO: 64 is the amino acid sequence of the $V_L$ of G4.
SEQ ID NO: 65 is the amino acid sequence of the HFWR1 of F11.
SEQ ID NO: 66 is the amino acid sequence of the HCDR1 of F11.
SEQ ID NO: 67 is the amino acid sequence of the HFWR2 of F11.
SEQ ID NO: 68 is the amino acid sequence of the HCDR2 of F11.
SEQ ID NO: 69 is the amino acid sequence of the HFWR3 of F11.
SEQ ID NO: 70 the amino acid sequence of the HCDR3 of F11.
SEQ ID NO: 71 is the amino acid sequence of the HFWR4 of F11.
SEQ ID NO: 72 is the amino acid sequence of the $V_H$ of F11.
SEQ ID NO: 73 is the amino acid sequence of the LFWR1 of F11.
SEQ ID NO: 74 is the amino acid sequence of the LCDR1 of F11.
SEQ ID NO: 75 is the amino acid sequence of the LFWR2 of F11.
SEQ ID NO: 76 is the amino acid sequence of the LCDR2 of F11.
SEQ ID NO: 77 is the amino acid sequence of the LFWR3 of F11.
SEQ ID NO: 78 the amino acid sequence of the LCDR3 of F11.
SEQ ID NO: 79 is the amino acid sequence of the LFWR4 of F11.
SEQ ID NO: 80 is the amino acid sequence of the $V_L$ of F11.

II. Antibodies that Specifically Bind a Genogroup II Norovirus Polypeptide.

SEQ ID NO: 81 is the amino acid sequence of the HFWR1 of C9.
SEQ ID NO: 82 is the amino acid sequence of the HCDR1 of C9.
SEQ ID NO: 83 is the amino acid sequence of the HFWR2 of C9.
SEQ ID NO: 84 is the amino acid sequence of the HCDR2 of C9.
SEQ ID NO: 85 is the amino acid sequence of the HFWR3 of C9.
SEQ ID NO: 86 the amino acid sequence of the HCDR3 of C9.
SEQ ID NO: 87 is the amino acid sequence of the HFWR4 of C9.
SEQ ID NO: 88 is the amino acid sequence of the $V_H$ of C9.
SEQ ID NO: 89 is the amino acid sequence of the LFWR1 of C9.
SEQ ID NO: 90 is the amino acid sequence of the LCDR1 of C9.
SEQ ID NO: 91 is the amino acid sequence of the LFWR2 of C9.
SEQ ID NO: 92 is the amino acid sequence of the LCDR2 of C9.
SEQ ID NO: 93 is the amino acid sequence of the LFWR3 of C9.
SEQ ID NO: 94 the amino acid sequence of the LCDR3 of C9.
SEQ ID NO: 95 is the amino acid sequence of the LFWR4 of C9.
SEQ ID NO: 96 is the amino acid sequence of the $V_L$ of C9.
SEQ ID NO: 97 is the amino acid sequence of the HFWR1 G3.
SEQ ID NO: 98 is the amino acid sequence of the HCDR1 of G3.
SEQ ID NO: 99 is the amino acid sequence of the HFWR2 of G3.
SEQ ID NO: 100 is the amino acid sequence of the HCDR2 of G3.
SEQ ID NO: 101 is the amino acid sequence of the HFWR3 of G3.
SEQ ID NO: 102 the amino acid sequence of the HCDR3 of G3.
SEQ ID NO: 103 is the amino acid sequence of the HFWR4 of G3.
SEQ ID NO: 104 is the amino acid sequence of the $V_H$ of G3.
SEQ ID NO: 105 is the amino acid sequence of the LFWR1 of G3.
SEQ ID NO: 106 is the amino acid sequence of the LCDR1 of G3.
SEQ ID NO: 107 is the amino acid sequence of the LFWR2 of G3.
SEQ ID NO: 108 is the amino acid sequence of the LCDR2 of G3.
SEQ ID NO: 109 is the amino acid sequence of the LFWR3 of G3.

SEQ ID NO: 110 the amino acid sequence of the LCDR3 of G3.

SEQ ID NO: 111 is the amino acid sequence of the LFWR4 of G3.

SEQ ID NO: 112 is the amino acid sequence of the $V_L$ of G3.

SEQ ID NO: 113 is the amino acid sequence of the HFWR1 B72.

SEQ ID NO: 114 is the amino acid sequence of the HCDR1 of B72.

SEQ ID NO: 115 is the amino acid sequence of the HFWR2 of B72.

SEQ ID NO: 116 is the amino acid sequence of the HCDR2 of B72.

SEQ ID NO: 117 is the amino acid sequence of the HFWR3 of B72.

SEQ ID NO: 118 the amino acid sequence of the HCDR3 of B72.

SEQ ID NO: 119 is the amino acid sequence of the HFWR4 of B72.

SEQ ID NO: 120 is the amino acid sequence of the $V_H$ of B72.

SEQ ID NO: 121 is the amino acid sequence of the LFWR1 of B72.

SEQ ID NO: 112 is the amino acid sequence of the LCDR1 of B72.

SEQ ID NO: 123 is the amino acid sequence of the LFWR2 of B72.

SEQ ID NO: 124 is the amino acid sequence of the LCDR2 of B72.

SEQ ID NO: 125 is the amino acid sequence of the LFWR3 of B72.

SEQ ID NO: 126 the amino acid sequence of the LCDR3 of B72.

SEQ ID NO: 127 is the amino acid sequence of the LFWR4 of B72.

SEQ ID NO: 128 is the amino acid sequence of the $V_L$ of B72.

SEQ ID NO: 129 is the amino acid sequence of the HFWR1 of D4.

SEQ ID NO: 130 is the amino acid sequence of the HCDR1 of D4.

SEQ ID NO: 131 is the amino acid sequence of the HFWR2 of D4.

SEQ ID NO: 132 is the amino acid sequence of the HCDR2 of D4.

SEQ ID NO: 133 is the amino acid sequence of the HFWR3 of D4.

SEQ ID NO: 134 the amino acid sequence of the HCDR3 of D4.

SEQ ID NO: 135 is the amino acid sequence of the HFWR4 of D4.

SEQ ID NO: 136 is the amino acid sequence of the $V_H$ of D4.

SEQ ID NO: 137 is the amino acid sequence of the LFWR1 of D4.

SEQ ID NO: 138 is the amino acid sequence of the LCDR1 of D4.

SEQ ID NO: 139 is the amino acid sequence of the LFWR2 of D4.

SEQ ID NO: 140 is the amino acid sequence of the LCDR2 of D4.

SEQ ID NO: 141 is the amino acid sequence of the LFWR3 of D4.

SEQ ID NO: 142 the amino acid sequence of the LCDR3 of D4.

SEQ ID NO: 143 is the amino acid sequence of the LFWR4 of D4.

SEQ ID NO: 144 is the amino acid sequence of the $V_L$ of D4.

III. Nucleic Acids

SEQ ID NO: 145 is a synthetic nucleic acid sequence.

SEQ ID NO: 146 is an exemplary nucleic acid sequence encoding the B72 heavy chain.

SEQ ID NO: 147 is an exemplary nucleic acid sequence encoding the C9 heavy chain.

SEQ ID NO: 148 is an exemplary nucleic acid sequence encoding the G3 heavy chain.

SEQ ID NO: 149 is an exemplary nucleic acid sequence encoding the D4 heavy chain.

SEQ ID NO: 150 is an exemplary nucleic acid sequence encoding the B72 light chain.

SEQ ID NO: 151 is an exemplary nucleic acid sequence encoding the C9 light chain.

SEQ ID NO: 152 is an exemplary nucleic acid sequence encoding the G3 light chain.

SEQ ID NO: 153 is an exemplary nucleic acid sequence encoding the D4 light chain.

SEQ ID NO: 154 is an exemplary nucleic acid sequence encoding the B7 heavy chain.

SEQ ID NO: 155 is an exemplary nucleic acid sequence encoding the D8 heavy chain.

SEQ ID NO: 156 is an exemplary nucleic acid sequence encoding the E3 heavy chain.

SEQ ID NO: 157 is an exemplary nucleic acid sequence encoding the G4 heavy chain.

SEQ ID NO: 158 is an exemplary nucleic acid sequence encoding the F11 heavy chain.

SEQ ID NO: 159 is an exemplary nucleic acid sequence encoding the B7 light chain.

SEQ ID NO: 160 is an exemplary nucleic acid sequence encoding the E3 light chain.

SEQ ID NO: 161 is an exemplary nucleic acid sequence encoding the D8 light chain.

SEQ ID NO: 162 is an exemplary nucleic acid sequence encoding the G4 light chain.

SEQ ID NO: 163 is an exemplary nucleic acid sequence encoding the F11 light chain.

DETAILED DESCRIPTION OF SEVERAL EMBODIMENTS

NoVs are nonenveloped ~38 nm icosahedral viruses with an approximately 7.5 kb single-stranded, positive-sense RNA genome that encodes three open reading frames (ORFs). ORF1 encodes RNA-dependent RNA polymerase, while ORFs 2 and 3 encode the major (VP1) and minor (VP2) capsid proteins, respectively. The VP1 is structurally divided into the shell domain (S) that forms the internal structural core of the particle and the protruding domain (P) that is exposed on the outer surface (Prasad et al., 1999, Science 286:287-90). The P domain is further subdivided into the P1 subdomain (residues 226 to 278 and 406 to 520) and the P2 subdomain (residues 279 to 405) (Prasad et al., 1999, J Virol 68:5117-25). P2 represents the most exposed surface of the viral particle and is involved in interactions with both neutralizing antibodies and HBGA oligosaccharides (Cao et al., 2007, J Virol 81:5949-57; Chen et al., 2006, Proc Natl Acad Sci USA 103:8048-53; Lochridge et al., 2005, J Gen Virol 86:2799-806).

NoVs are divided into five distinct genogroups (GI-GV) based on VP1 sequence similarity. Different types within each Genogroup are separated from the Genogrop by a decimal point. Virus strains from GI and GII are responsible for most human infections, and these genogroups are further subdivided into more than 25 different genotypes (Zheng et al., 2006, Virology 346:312-23). Although human NoV GII.4 strains are now recognized as the predominant genotype, the GI.1 NV has been studied most extensively because of its historical precedence (Kapikian, 2000, J Infect Dis 181 Suppl 2:S295-302). Early human challenge studies with NV provided evidence for short-term, but not long-term (>2 years), homologous immunity following infection with NV(16, 17, 37), and showed also the absence of heterotypic immunity when cross-challenged with the GII.1 Hawaii virus (Wyatt et al., 1974, J Infect Dis 129:709-14). Later human challenge studies showed an association between HBGA secretor status and susceptibility to NV infection (Harrington et al., J Virol 76:12335-43, Hutson et al., 2002, J Infect Dis 185:1335-7; Lindesmith et al., Nat Med 9:548-531 Marionneau et al., 2002, Gastroenterology 122:1967-77). Chimpanzees were found to be susceptible to NV infection (Zintz et al., 2005, Infect Genet Evol 5:281-90), and are useful as a model for the study of NoV pathogenesis and vaccine development (Bok et al., 2011, Proc Natl Acad Sci USA 108:325-30; Wyatt et al., 1978, J Med Virol 2:89-96). The elucidation of human NoV virion structure is based largely on the X-ray crystallographic analysis of NV rVLPs (Prasad et al., 1999, Science 286:287-90; Prasad et al., 1994, J Virol 68:5117-25); these VLPs are a promising NoV vaccine candidate (Atmar et al., 2011, N Engl J Med 365:2178-87).

Clinically and diagnostically useful chimpanzee-derived monoclonal antibodies that specifically bind NV are disclosed herein. Since chimpanzee immunoglobulins (Igs) are virtually identical to human Igs, chimpanzee-derived MAbs may be administered to humans without modification. Antibodies to NV were induced in chimpanzees by an immunization strategy of infection and priming with live NV, followed by boosting with NV rVLPs. A panel of NV-specific-MAbs was then generated by phage display library technology from chimpanzee bone marrow B cells and immortalized memory B cells derived from peripheral blood mononuclear cells (PBMCs). Additional clinically and diagnostically useful chimpanzee monoclonal antibodies that specifically bind NoVs are also disclosed herein.

In some embodiments, NoVs as discussed herein are genogroup I NoVs, which include, but are not limited to, NV. In some embodiments, NoVs are genogroup II NoVs, which include, but are not limited to, GII.4 NoVs. Examples of NoVs include, but are not limited to, NV (NV, see, for example, GENBANK® Accession No. M87661, NP_056821), Southampton virus (SHV, see, for example, GENBANK® Accession No. L07418), Desert Shield virus (DSV, see, for example, GENBANK® Accession No. U04469), Hesse virus (HSV), Chiba virus (CHV, see, for example, GENBANK® Accession No. AB042808), Hawaii virus (HV, see, for example, GENBANK® Accession No. U07611), Snow Mountain virus (SMV, see, for example, GENBANK® Accession No. U70059), Toronto virus (TV, Leite et al., Arch. Virol. 141:865-875), Bristol virus (BV), Jena virus (JV, see, for example, GENBANK® Accession No. AJ01099), MD145-12 virus (MD145-12, see, for example, GENBANK® Accession No. AY032605), Seto virus (SV, see, for example, GENBANK® Accession No. AB031013), Camberwell (CV, see, for example, GENBANK® Accession No. AF145896), Lordsdale virus (LV, see, for example, GENBANK® Accession No. X86557), Grimsby virus (GrV, see, for example, GENBANK® Accession No. AJ004864), Mexico virus (MXV, see, for example, GENBANK® Accession No. U22498), Boxer (see, for example, GENBANK® Accession No. AF538679), C59 (see, for example, GENBANK® Accession No. AF435807), VA115 (see, for example, GENBANK® Accession No. AY038598), BUDS (see, for example, GENBANK® Accession No. AY660568), MOH (see, for example, GENBANK® Accession No. AF397156), Parris Island (PiV; see, for example, GENBANK® Accession No. AY652979), VA387 (see, for example, GENBANK® Accession No. AY038600), VA207 (see, for example, GENBANK® Accession No. AY038599), and Operation Iraqi Freedom (see, for example, OIF, GENBANK® Accession No. AY675554).

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs.

Administration: The introduction of a composition into a subject by a chosen route. Administration can be local or systemic. For example, if the chosen route is intravenous, the composition is administered by introducing the composition into a vein of the subject. In some examples a disclosed antibody specific for a NoV polypeptide, such as a Nowalk virus polypeptide, is administered to a subject.

Agent: Any substance or any combination of substances that is useful for achieving an end or result; for example, a substance or combination of substances useful for inhibiting a NoV infection in a subject. Agents include, and are not limited to, proteins, nucleic acid molecules, compounds, small molecules, organic compounds, inorganic compounds, or other molecules of interest. An agent can include a therapeutic agent (such as an anti-viral agent), a diagnostic agent or a pharmaceutical agent. In some embodiments, the agent is a polypeptide agent (such as a neutralizing antibody), or an anti-viral agent. The skilled artisan will understand that particular agents may be useful to achieve more than one result.

Amino acid substitution: The replacement of one amino acid in peptide with a different amino acid.

Amplification: A technique that increases the number of copies of a nucleic acid molecule (such as an RNA or DNA). An example of amplification is the polymerase chain reaction, in which a biological sample is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in PCT Publication No. WO 90/01069; ligase chain reaction amplification, as disclosed in European Patent Publication EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as a NoV polypeptide, a NV polypeptide, VP1, or an immunogenic fragment thereof, for example the P1 or P2 domain Immunoglobulin genes include the kappa, lambda, alpha, gamma, delta, epsilon and mu constant region genes, as well as the myriad immunoglobulin variable region genes.

Antibodies exist, for example, as intact immunoglobulins and as a number of well characterized fragments produced by digestion with various peptidases. For instance, Fabs, Fvs, scFvs that specifically bind to a NoV polypeptide, for example VP1, or fragments of this polypeptide, are specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies and heteroconjugate antibodies such as bispecific antibodies. See also, *Pierce Catalog and Handbook,* 1994-1995 (Pierce Chemical Co., Rockford, Ill.); Kuby, *Immunology,* 3$^{rd}$ Ed., W.H. Freeman & Co., New York, 1997.

Antibody fragments include, but are not limited to, the following: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule.

Antigen binding fragments of an antibody can be produced by the modification of whole antibodies or those synthesized de novo using recombinant DNA methodologies. In some examples, the term antibody includes the amino acid sequences of one or more of the CDRs from the antibody grafted onto a scaffold.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. The disclosed antibodies can be class switched.

Each heavy and light chain contains a constant region and a variable region, (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest,* U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for antigen binding. The extent of the framework region and CDRs have been defined (see, Kabat et al., *Sequences of Proteins of Immunological Interest,* U.S. Department of Health and Human Services, 1991, which is hereby incorporated by reference in its entirety). The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system. Lefranc, et al. ("IMGT unique numbering for immunoglobulin and T cell receptor variable domains and Ig superfamily V-like domains," Dev. Comp. Immunol., 27:55-77, 2003) discloses the "IMGT" numbering scheme for CDRs. The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs of each chain are typically referred to as CDR1, CDR2, and CDR3 (from the N-terminus to C-terminus), and are also typically identified by the chain in which the particular CDR is located. Thus, a V$_H$ CDR3 is located in the variable domain of the heavy chain of the antibody in which it is found, whereas a V$_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "V$_H$" or "VH" refer to the variable region of an immunoglobulin heavy chain, including that of an antibody fragment, such as Fv, scFv, dsFv or Fab. References to "V_L" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." In some embodiments, monoclonal antibodies can be humanized monoclonal antibodies. In some embodiments, monoclonal antibodies can be chimeric antibodies. In some examples monoclonal antibodies are isolated from a subject. The amino acid sequences of such isolated monoclonal antibodies can be determined.

A "humanized" antibody is an antibody including a human framework region and one or more CDRs from a non-human (such as a chimpanzee, mouse, rat, or synthetic) immunoglobulin. The non-human antibody providing the CDRs is termed a "donor," and the human antibody providing the framework is termed an "acceptor." In one embodiment, all the CDRs are from the donor antibody in a humanized antibody. Constant regions need not be present, but if they are, they must be substantially identical to human antibody constant regions, such as at least about 85-90%, such as about 95% or more identical. Hence, all parts of a humanized antibody, except possibly the CDRs, are substantially identical to corresponding parts of natural human antibody sequences. A "humanized antibody" can include a humanized light chain and a humanized heavy chain. A humanized antibody binds to the same antigen as the donor antibody that provides the CDRs. The acceptor framework of a humanized antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

A "chimeric" antibody is an antibody which includes sequences from two different antibodies, which typically are of different species. In some examples, a chimeric antibody includes one or more CDRs and/or framework regions from one chimpanzee antibody and CDRs and/or framework regions from another chimpanzee antibody. In some embodiments, a chimeric antibody comprises heavy and light chain variable regions derived from a first species and heavy and light chain constant regions derived from a second species. In some embodiments, the variable and constant regions of the light chain are derived from a first species while the variable region of the heavy chain is derived from the first species and the constant region of the heavy chain is derived from a second species. In some embodiments, the first species is non-human and includes, but is not limited to, chimpanzees. In additional embodiments, the second species includes, but is not limited to, humans, mouse or rabbit.

A "neutralizing antibody" is an antibody which reduces the infectious titer of an infectious agent by binding to a specific antigen on the infectious agent. In some examples the infectious agent is a virus. In some examples, an antibody that is specific for a NoV, such as a Norwalk virus, neutralizes the infectious titer of the virus.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In some embodiments, an antigen is derived from a NoV, such as a Norwalk virus. In some embodiments, the antigen is a NoV VP1 polypeptide or antigenic fragment thereof, such as a P1 or P2 domain.

A "target epitope" is a specific epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody.

Binding affinity: Affinity of an antibody or antigen binding fragment thereof for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

Capsid protein (VP1): A capsid polypeptide that is encoded by open reading frame (ORF) 2 of the NoV genome; the polypeptide itself assembles to form an icosahedral capsid. When the protein is 530 amino acids in length, the shell (S) domain (amino acids 1-225) contains elements necessary for the formation of the icosahedron. The Protruding domain (P, amino acids 225-530) is divided into sub-domains P1 (amino acids 226-278 (P1 subdomain 1) and 406-530 (P1 subdomain 2) and P2 (amino acids 279-405). The P domain interacts in dimeric contacts that increase the stability of the capsid and form the protrusions on the virion. The P2 domain is hypervariable. An exemplary VP1 is provided in UNIPROT Accession No. Q83884 (for example, CAPSD_NVN68, Oct. 3, 2012), which is incorporated herein by reference.

Clonal variant: Any sequence, which differs by one or more nucleotides or amino acids, in presence of V region with identical mutations compared to the germline, identical VDJ or VJ gene usage, and identical D and J length. The "germline" sequence is intended to be the sequence coding for the antibody/immunoglobulin (or of any fragment thereof) deprived of mutations, for example somatic mutations. The percentage of homology represents an indication of the mutational events which any type of heavy chain portion undergoes after contact with an antigen.

Computer readable media: Any medium or media, which can be read and accessed directly by a computer, so that the media is suitable for use in a computer system. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

Conjugate: A complex of two molecules linked together, for example, linked together by a covalent bond. In one embodiment, an antibody is linked to an effector molecule; for example, an antibody that specifically binds to a NoV polypeptide, such as a NV polypeptide, covalently linked to an effector molecule or to a toxin. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules." In one embodiment, an antibody linked to an effector molecule is further joined to a lipid or other molecule to a protein or peptide to increase its half-life in the body.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a sample obtained from a healthy patient. In other embodiments, the control is a tissue sample obtained from a patient diagnosed with a NoV infection, such as a Norwalk virus infection that serves as a positive control. In still other embodiments, the control is a historical control or standard reference value or range of values (such as a previously tested control sample, such as a group of infected patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Non-limiting examples of detectable markers include fluorophores, fluorescent proteins, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Detecting: To identify the existence, presence, or fact of something General methods of detecting are known to the skilled artisan (see, for example, U.S. Pat. No. 7,635,476) and may be supplemented with the protocols and reagents disclosed herein. For example, included herein are methods of detecting a cell that expresses a NoV polypeptide, such as a Norwalk virus polypeptide, for example, VP1, in a subject. In some embodiments, the peptide can be VP1.

Effector molecule: The portion of a chimeric molecule that is intended to have a desired effect on a cell to which the chimeric molecule is targeted. Effector molecule is also known as an effector moiety, therapeutic agent, or diagnostic agent, or similar terms.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on the surface of VP1 from a NoV, such as the P2 subdomain.

Framework Region: Amino acid sequences interposed between CDRs. The term includes variable light and variable heavy framework regions. The framework regions serve to hold the CDRs in an appropriate orientation for antigen binding.

Fc polypeptide: The polypeptide comprising the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not comprise the tailpiece, and may or may not be bound by the J chain. For IgG, the Fc region comprises immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to comprise residues C226 or P230 to its carboxyl-terminus, wherein the numbering is according to the EU index as in Kabat. For IgA, the Fc region comprises immunoglobulin domains Calpha2 and Calpha3 (Cα2 and Cα3) and the lower part of the hinge between Calpha1 (Cα1) and Cα2. Encompassed within the definition of the Fc region are functionally equivalent analogs and variants of the Fc region. A functionally equivalent analog of the Fc region may be a variant Fc region, comprising one or more amino acid modifications relative to the wild-type or naturally existing Fc region. Variant Fc regions will possess at least 50% homology with a naturally existing Fc region, such as about 80%, and about 90%, or at least about 95% homology. Functionally equivalent analogs of the Fc region may comprise one or more amino acid residues added to or deleted from the N- or C-termini of the protein, such as no more than 30 or no more than 10 additions and/or deletions. Functionally equivalent analogs of the Fc region include Fc regions operably linked to a fusion partner. Functionally equivalent analogs of the Fc region must comprise the majority of all of the Ig domains that compose Fc region as defined above; for example IgG and IgA Fc regions as defined herein must comprise the majority of the sequence encoding $CH_2$ and the majority of the sequence encoding $CH_3$. Thus, the $CH_2$ domain on its own, or the $CH_3$ domain on its own, are not considered Fc region. The Fc region may refer to this region in isolation, or this region in the context of an Fc fusion polypeptide.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$. In mice, this class comprises $IgG_1$, $IgG_{2a}$, $IgG_{2b}$, $IgG_3$.

Immune complex: The binding of antibody to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography Immunological binding properties of selected antibodies may be quantified using methods well known in the art.

Immunoadhesin: A molecular fusion of a protein with the Fc region of an immunoglobulin, wherein the immunoglobulin retains specific properties, such as Fc receptor binding and increased half-life. An Fc fusion combines the Fc region of an immunoglobulin with a fusion partner, which in general can be any protein, polypeptide, peptide, or small molecule. In one example, an immunoadhesin includes the hinge, $CH_2$, and $CH_3$ domains of the immunoglobulin gamma 1 heavy chain constant region. In another example, the immunoadhesin includes the $CH_2$, and $CH_3$ domains of an IgG.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such a NoV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B-cell, a nucleic acid, peptide, protein, heavy chain domain or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids. In some examples an antibody, such as an antibody specific for a NoV polypeptide can be isolated, for example isolated from a subject infected with the virus.

$K_d$: The dissociation constant for a given interaction, such as a polypeptide ligand interaction or an antibody antigen interaction. For example, for the bimolecular interaction of an antibody (such as any of the antibodies disclosed herein) and an antigen (such as a NoV polypeptide, for example a Norwalk virus polypeptide) it is the concentration of the individual components of the bimolecular interaction divided by the concentration of the complex.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In some examples, a disclosed antibody is labeled.

Neutralizing antibody: An antibody which reduces the infectious titer of an infectious agent by binding to a specific antigen on the infectious agent. In some examples the infectious agent is a virus, such as a NoV, for example Norwalk virus. In some examples, an antibody that is specific for a NoV polypeptide neutralizes the infectious titer of the virus. In some examples, an antibody specific for NoV VP1 neutralizes the infectious titer of the virus. In vitro assays for neutralization are known in the art. Thus, in some non-limiting examples, an assay for neutralization activity is blocking the binding of NoV-like particles (VLPs) to H1 HBGA carbohydrate in a dose dependent manner. In other non-limiting examples, an assay for neutralization is the inhibition of hemagglutination activity.

With regard to an antigen from a pathogen, such as a virus, a "broadly neutralizing" antibody can bind to and inhibit the function of an antigen from more than one class and/or subclass of the pathogen. For example, with regard to a NoV, the antibody can bind to and inhibit the function of an antigen, such as a viral protein, from more than one genotype of NoV, including, but not limited to, NV (GI.1), Southampton virus (GI.2), Desert Shield virus (GI.3), Hawaii virus (GII.1), Snow Mountain virus (GII.2), Mexico virus (GII.3), and MD145-12 virus (GII.4), or viruses from more than one genogroup (GI-GV). In one embodiment, broadly neutralizing antibodies to NoVs are distinct from other antibodies in that they neutralize a high percentage of the many types of NoVs.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

ClustalW is a program that aligns three or more sequences in a computationally efficient manner. Aligning multiple sequences highlights areas of similarity which may be associated with specific features that have been more highly conserved than other regions. Thus, this program can classify sequences for phylogenetic analysis, which aims to model the substitutions that have occurred over evolution and derive the evolutionary relationships between sequences. The ClustalW multiple sequence alignment web form is available on the internet from EMBL-EBI (ebi.ac.uk/Tools/msa/clustalw2/), see also Larkin et al., *Bioinformatics* 2007 23(21): 2947-2948.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids, which include, but are not limited to, water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples a pharmaceutical agent includes one or more of the disclosed antibodies.

Polypeptide: Any chain of amino acids, regardless of length or post-translational modification (e.g., glycosylation or phosphorylation). In one embodiment, the polypeptide is NoV polypeptide, such as a capsid polypeptide. In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of polypeptide sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene*

73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations. The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet (along with a description of how to determine sequence identity using this program).

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Nucleic acids that "selectively hybridize" or "selectively bind" do so under moderately or highly stringent conditions that excludes non-related nucleotide sequences. In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Specifically bind: When referring to an antibody, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example VP1 or any other NoV polypeptide) and do not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar, such as less than about $10^{-7}$ Molar, $10^{-8}$ Molar, $10^{-9}$, or even less than about $10^{-1}$ Molar.

Therapeutic agent: Used in a generic sense, it includes treating agents, prophylactic agents, and replacement agents.

Therapeutically effective amount or effective amount: A quantity of a specific substance, such as a disclosed antibody, sufficient to achieve a desired effect in a subject being treated. For instance, this can be the amount necessary to inhibit NoV replication or NV replication, or to treat an infection with the virus. In several embodiments, a therapeutically effective amount is the amount necessary to reduce a sign or symptom of the infection, and/or to decrease viral titer in a subject. When administered to a subject, a dosage will generally be used that will achieve target tissue concentrations that has been shown to achieve a desired in vitro effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Specifically Bind a NoV Polypeptide

Isolated monoclonal antibodies and antigen binding fragments thereof that specifically bind a NoV) polypeptide are disclosed herein. In some embodiments the monoclonal antibodies specifically bind a NoV polypeptide with an equilibrium constant ($K_d$) of 1 nM or less. In several embodiments, the antibodies and antigen binding fragments bind the NoV polypeptide, such as a Norwalk virus polypeptide, with a binding affinity of $1\times10^{-9}$ M, at least about $1.5\times10^{-9}$M, at least about $2\times10^{-9}$M, at least about $3\times10^{-9}$ M, at least about $3\times10^{-9}$ M, at least about $5\times10^{-9}$M, at least about $6\times10^{-9}$M, at least about $7\times10^{-9}$ M, at least about $8\times10^{-9}$M, at least about $9\times10^{-9}$M, or at least about $1\times10^{-10}$ M.

In some embodiments, the antibody specifically binds a NoV Genogroup I or a NoV Genogroup II polypeptide. In some embodiments, the antibody specifically binds a Norwalk virus polypeptide. The antibody can specifically bind a viral polypeptide (VP) 1. In some examples, the monoclonal antibody specifically binds a P1 or P2 subdomain of VP1. In further embodiments, the antibody specifically binds to a particular NoV and does not bind other NoVs. In some embodiments, the NoV is NV or MD145-12.

In some embodiments, the antibody is neutralizing. In further embodiments the antibody is broadly neutralizing. For example, the antibody can neutralize viruses from more than one genogroup (GI-GV) of the virus. In other embodiments, the antibody inhibits the binding of NoV VLPs to H1 HBGA carbohydrate in a dose dependent manner. In additional embodiments, the antibody inhibits hemagglutination activity.

The MAb can be of any isotype. The MAb can be, for example, an IgM or an IgG antibody, such as $IgG_1$ or an $IgG_2$. The class of an antibody that specifically binds IGF-II can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds IGF-II that was originally IgM may be class switched to an IgG. Class switching can be used to convert one IgG subclass to another, such as from $IgG_1$ to $IgG_2$.

The monoclonal antibodies disclosed herein can be chimpanzee antibodies, and can include a chimpanzee framework region. In some embodiments, the antibodies are humanized, and thus include one or more human framework regions. Exemplary framework regions are disclosed, for example, in PCT Publication No. WO 2011/038290 and Published U.S. Patent Application No. 2012/0244166A1, which are incorporated by reference herein. In some embodiments, the MAbs disclosed herein are chimeric antibodies. In some embodiments, the MAbs include chimpanzee and human regions.

The monoclonal antibody can specifically bind a NoV polypeptide. In some embodiments, the monoclonal antibody includes a heavy chain variable domain and a light chain variable domain. Naturally-occurring antibodies are immunoglobulin molecules comprised of four polypeptide chains, two heavy (H) chains and two light (L) chains inter-connected by disulfide bonds. Each heavy chain is comprised of a heavy chain variable region (VH) and a heavy chain constant region. The heavy chain constant region is comprised of three domains, CH1, CH2 and CH3. Each light chain is comprised of a light chain variable region (VL) and a light chain constant region. The light chain constant region is comprised of one domain, CL. The VH and VL regions can be further subdivided into regions of hypervariability, called complementarity determining regions (CDR), interspersed with regions that are more conserved, called framework regions (FWR). Each VH and VL is composed of three CDRs and four FWRs, arranged from amino-terminus to carboxy-terminus in the following order: FWR1, CDR1, FWR2, CDR2, FWR3, CDR3, FWR4.

CDRs and FWRs may be defined according to Kabat (Sequences of Proteins of Immunological Interest (National Institutes of Health, Bethesda, Md., 1987 and 1991) Amino acid numbering of antibodies or antigen binding fragments is also according to that of Kabat. Each CDR can include amino acid residues from a complementarity determining region as defined by Kabat (i.e. about residues 24-34 (CDR-L1), 50-56 (CDR-L2) and 89-97 (CDR-L3) in the light chain variable domain (and 31-35 (CDR-H1), 50-65 (CDR-H2) and 95-102 (CDR-H3) in the heavy chain variable domain (SEQ ID NO:2). However, in some antibodies the CDRs include those residues from a hypervariable loop (i.e. about residues 26-32 (CDR-L1), 50-52 (CDR-L2) and 91-96 (CDR-L3) in the light chain variable domain (SEQ ID NO:1) and 26-32 (CDR-H1), 53-55 (CDR-H2) and 96-101 (CDR-H3) in the heavy chain variable domain (SEQ ID NO:2); Chothia and Lesk J. Mol. Biol. 196:901-917 (1987)). In some instances, a complementarity determining region can include amino acids from both a CDR region defined according to Kabat and a hypervariable loop.

In a wild type antibody, each variable domain typically has four FWRs identified as FWR1, FWR2, FWR3 and FWR4. If the CDRs are defined according to Kabat, the light chain FWR residues are positioned at about residues 1-23 (LCFR1), 35-49 (LCFR2), 57-88 (LCFR3), and 98-107 (LCFR4) of SEQ ID NO:1) and the heavy chain FWR residues are positioned about at residues 1-30 (HCFR1), 36-49 (HCFR2), 66-94 (HCFR3), and 103-113 (HCFR4) of SEQ ID NO:2. If the CDRs comprise amino acid residues from hypervariable loops, the light chain FWR residues are positioned about at residues 1-25 (LCFR1), 33-49 (LCFR2), 53-90 (LCFR3), and 97-107 (LCFR4) in the light chain (SEQ ID NO:1) and the heavy chain FWR residues are positioned about at residues 1-25 (HCFR1), 33-52 (HCFR2), 56-95 (HCFR3), and 102-113 (HCFR4) in the heavy chain (SEQ ID NO:2). In some instances, when the CDR comprises amino acids from both a CDR as defined by Kabat and those of a hypervariable loop, the FWR residues are adjusted accordingly.

Thus, in some embodiments, the monoclonal antibody includes one or more heavy chain CDRs from the variable domains shown in FIGS. 2 and 7, as defined by the Kabat, Chothia or IMGT numbering system. As shown in FIGS. 2 and 7, in some embodiments, the CDRs can be identified using Kabat positioning. In certain embodiments, the monoclonal antibody includes a H-CDR1 comprising residues 31-35, an H-CDR2 comprising residues 50-65, and an H-CDR3 comprising residues 95-102 of any one of SEQ ID NOs: 8, 24, 40, 56, 72, 88, 104, 120, or 136, as identified by Kabat position.

In additional embodiments, the monoclonal antibody includes one or more light chain CDRs from the variable domains shown in FIGS. 2 and 7, as defined by the Kabat, Chothia or IMGT numbering system. As shown in FIGS. 2 and 7, the CDRs can be identified using Kabat positioning. In certain embodiments, the light chain variable domain can include a L-CDR1 comprising residues 24-34, an H-CDR2 comprising residues 50-56, and an H-CDR3 comprising residues 89-97 of any one of SEQ ID NOs: 16, 32, 48, 64, 80, 96, 112, 128 or 144, as identified by Kabat position.

In some embodiments, the monoclonal antibody specifically binds a NoV polypeptide, wherein the heavy chain of the monoclonal antibody includes:

(j) a HCDR1 including the amino acid sequence set forth as SEQ ID NO: 2, a HCDR2 including the amino acid sequence set forth as SEQ ID NO: 4, and/or an HCDR3 including the amino acid sequence set forth as SEQ ID NO: 6;

(k) a HCDR1 including the amino acid sequence set forth as SEQ ID NO: 18, a HCDR2 including the amino acid sequence set forth as SEQ ID NO: 20, and/or a HCDR3 including the amino acid sequence set forth as SEQ ID NO: 22;

(l) a HCDR1 including the amino acid sequence set forth as SEQ ID NO: 34, a HCDR2 including the amino acid sequence set forth as SEQ ID NO: 36, and a HCDR3 including the amino acid sequence set forth as SEQ ID NO: 38;

(m) a HCDR1 including the amino acid sequence set forth as SEQ ID NO: 50, the HCDR2 including the amino acid sequence set forth as SEQ ID NO: 52, and/or a HCDR3 including the amino acid sequence set forth as SEQ ID NO: 54;

(n) a HCDR1 including the amino acid sequence set forth as SEQ ID NO: 66, a HCDR2 including the amino acid sequence set forth as SEQ ID NO: 68, and/or a HCDR3 including the amino acid sequence set forth as SEQ ID NO: 70;

(o) a HCDR1 including the amino acid sequence set forth as SEQ ID NO: 82, a HCDR2 including the amino acid sequence set forth as SEQ ID NO: 84, and/or a HCDR3 including the amino acid sequence set forth as SEQ ID NO: 86;

(p) a HCDR1 including the amino acid sequence set forth as SEQ ID NO: 98, a HCDR2 including the amino acid sequence set forth as SEQ ID NO: 100, and/or a HCDR3 including the amino acid sequence set forth as SEQ ID NO: 102;

(q) a HCDR1 including the amino acid sequence set forth as SEQ ID NO: 114, a HCDR2 including the amino acid sequence set forth as SEQ ID NO: 116, and/or a HCDR3 including the amino acid sequence set forth as SEQ ID NO: 118; or (r) a HCDR1 including the amino acid sequence set forth as SEQ ID NO: 130, a HCDR2 including the amino acid sequence set forth as SEQ ID NO: 132, and/or a HCDR3 including the amino acid sequence set forth as SEQ ID NO: 134.

In specific non-limiting examples, the monoclonal antibody specifically binds a NV polypeptide, such as VP1 (see a-e above).

In additional embodiments, the monoclonal antibody specifically binds a NoV polypeptide, wherein the light chain of the monoclonal antibody includes:

(a) a LCDR1 including the amino acid sequence set forth as SEQ ID NO: 10, a LCDR2 including the amino acid sequence set forth as SEQ ID NO: 12, and/or a LCDR3 including the amino acid sequence set forth as SEQ ID NO: 14;

(b) a LCDR1 including the amino acid sequence set forth as SEQ ID NO: 26, a LCDR2 including the amino acid sequence set forth as SEQ ID NO: 28, and/or a LCDR3 including the amino acid sequence set forth as SEQ ID NO: 30;

(c) a LCDR1 including the amino acid sequence set forth as SEQ ID NO: 42, a LCDR2 including the amino acid sequence set forth as SEQ ID NO: 44, and/or a LCDR3 including the amino acid sequence set forth as SEQ ID NO: 46;

(d) a LCDR1 including the amino acid sequence set forth as SEQ ID NO: 58, a LCDR2 including the amino acid sequence set forth as SEQ ID NO: 60, and/or a LCDR3 including the amino acid sequence set forth as SEQ ID NO: 62;

(e) a LCDR1 including the amino acid sequence set forth as SEQ ID NO: 74, a LCDR2 including the amino acid sequence set forth as SEQ ID NO: 76, and a LCDR3 including the amino acid sequence set forth as SEQ ID NO: 78;

(f) a LCDR1 including the amino acid sequence set forth as SEQ ID NO: 90, a LCDR2 including the amino acid sequence set forth as SEQ ID NO: 92, and/or a LCDR3 including the amino acid sequence set forth as SEQ ID NO: 94;

(g) a LCDR1 including the amino acid sequence set forth as SEQ ID NO: 106, a LCDR2 including the amino acid sequence set forth as SEQ ID NO: 108, and/or a LCDR3 including the amino acid sequence set forth as SEQ ID NO: 110;

(h) a LCDR1 including the amino acid sequence set forth as SEQ ID NO: 122, a LCDR2 including the amino acid sequence set forth as SEQ ID NO: 124, and/or a HCDR3 including the amino acid sequence set forth as SEQ ID NO: 126; or (i) a LCDR1 including the amino acid sequence set forth as SEQ ID NO: 138, a LCDR2 including the amino acid sequence set forth as SEQ ID NO: 140, and/or a HCDR3 including the amino acid sequence set forth as SEQ ID NO: 142.

In some embodiments, the monoclonal antibody includes a HCDR1 including the amino acid sequence set forth as SEQ ID NO: 2, a HCDR2 including the amino acid sequence set forth as SEQ ID NO: 4, a HCDR3 including the amino acid sequence set forth as SEQ ID NO: 6, a LCDR1 including the amino acid sequence set forth as SEQ ID NO: 10, a LCDR2 including the amino acid sequence set forth as SEQ ID NO: 12, and a LCDR3 including the amino acid sequence set forth as SEQ ID NO: 14, wherein the antibody specifically binds a NV VP1 polypeptide. In additional embodiments, the monoclonal antibody includes a HCDR1 including the amino acid sequence set forth as SEQ ID NO: 18, the HCDR2 including the amino acid sequence set forth as SEQ ID NO: 20, the HCDR3 including the amino acid sequence set forth as SEQ ID NO: 22, a LCDR1 including the amino acid sequence set forth as SEQ ID NO: 26, a LCDR2 including the amino acid sequence set forth as SEQ ID NO: 28, and a LCDR3 including the amino acid sequence set forth as SEQ ID NO: 30, wherein the antibody specifically binds a NV VP1 polypeptide. In further embodiments, the monoclonal antibody includes a HCDR1 including the amino acid sequence set forth as SEQ ID NO: 34, a HCDR2 including the amino acid sequence set forth as SEQ ID NO: 36, a HCDR3 including the amino acid sequence set forth as SEQ ID NO: 38, a LCDR1 including the amino acid sequence set forth as SEQ ID NO: 42, a LCDR2 including the amino acid sequence set forth as SEQ ID NO: 44, and a LCDR3 including the amino acid sequence set forth as SEQ ID NO: 46, wherein the antibody specifically binds a NV VP1 polypeptide. In yet other embodiments, the monoclonal antibody includes a HCDR1 including the amino acid sequence set forth as SEQ ID NO: 50, a HCDR2 including the amino acid sequence set forth as SEQ ID NO: 52, a HCDR3 including the amino acid sequence set forth as SEQ ID NO: 54, a LCDR1 including the amino acid sequence set forth as SEQ ID NO: 58, a LCDR2 including the amino acid sequence set forth as SEQ ID NO: 60, and a LCDR3 including the amino acid sequence set forth as SEQ ID NO: 62, wherein the antibody specifically binds a NV VP1 polypeptide. In additional embodiments, the monoclonal antibody includes a HCDR1 including the amino acid sequence set forth as SEQ ID NO: 66, a HCDR2 including the amino acid sequence set forth as SEQ ID NO: 68, a HCDR3 including the amino acid sequence set forth as SEQ ID NO: 70, a LCDR1 including the amino acid sequence set forth as SEQ ID NO: 74, a LCDR2 including the amino acid sequence set forth as SEQ ID NO: 76, and a LCDR3 including the amino acid sequence set forth as SEQ ID NO: 78, wherein the antibody specifically binds a NV VP1 polypeptide.

In some embodiments, the monoclonal antibody includes a HCDR1 including the amino acid sequence set forth as SEQ ID NO: 82, a HCDR2 including the amino acid sequence set forth as SEQ ID NO: 84, a HCDR3 including the amino acid sequence set forth as SEQ ID NO: 86, a LCDR1 including the amino acid sequence set forth as SEQ ID NO: 90, a LCDR2 including the amino acid sequence set forth as SEQ ID NO: 92, and a LCDR3 including the amino acid sequence set forth as SEQ ID NO: 94, wherein the monoclonal antibody specifically binds a NoV polypeptide. In other embodiments, the monoclonal antibody includes a HCDR1 including the amino acid sequence set forth as SEQ ID NO: 98, a HCDR2 including the amino acid sequence set forth as SEQ ID NO: 100, a HCDR3 including the amino acid sequence set forth as SEQ ID NO: 102, a LCDR1 including the amino acid sequence set forth as SEQ ID NO: 106, a LCDR2 including the amino acid sequence set forth as SEQ ID NO: 108, and a LCDR3 including the amino acid sequence set forth as SEQ ID NO: 110, wherein the monoclonal antibody specifically binds a NoV polypeptide. In additional embodiments, the monoclonal antibody includes a HCDR1 including the amino acid sequence set forth as SEQ ID NO: 114, a HCDR2 including the amino acid sequence set forth as SEQ ID NO: 116, a HCDR3 including the amino acid sequence set forth as SEQ ID NO: 118 a LCDR1 including the amino acid sequence set forth as SEQ ID NO: 122, a LCDR2 including the amino acid sequence set forth as SEQ ID NO: 124, and a LCDR3 including the amino acid sequence set forth as SEQ ID NO: 126, wherein the monoclonal antibody specifically binds a NoV polypeptide. In further embodiments, the monoclonal antibody includes a HCDR1 including the amino acid sequence set forth as SEQ ID NO: 130, a HCDR2 including the amino acid sequence set forth as SEQ ID NO: 132, a HCDR3 including the amino acid sequence set forth as SEQ ID NO: 134, a LCDR1 including the amino acid sequence set forth as SEQ ID NO: 138, a LCDR2 including the amino acid sequence set forth as SEQ ID NO: 140, and the LCDR3 including the amino acid sequence set forth as SEQ ID NO: 142, wherein the monoclonal antibody specifically binds a NoV polypeptide.

In some embodiments, the monoclonal antibody includes a heavy chain variable domain comprising an amino acid sequence at least 90%, 91%, 92%, 93%, 94%, 95%, 96%, 97%, 98% or 99% identical to one of the amino acid sequence set forth as one of SEQ ID NO: 8, SEQ ID NO: 24, SEQ ID NO: 40, SEQ ID NO: 56, SEQ ID NO: 72, SEQ ID NO: 88, SEQ ID NO: 104, SEQ ID NO: 120, or SEQ ID NO: 136. In additional embodiments, the heavy chain variable domain includes at most 10, at most 9, at most 8, at most 7, at most 6, at most 5, at most 4, at most 3, at most two or at most one conservative amino acid substitutions in an amino acid sequence set forth as one of SEQ ID NO: 8, SEQ ID NO: 24, SEQ ID NO: 40, SEQ ID NO: 56, SEQ ID NO: 72, SEQ ID NO: 88, SEQ ID NO: 104, SEQ ID NO: 120, or SEQ ID NO: 136. In yet other embodiments, the monoclonal antibody includes a heavy chain variable domain comprising or consisting of one of the amino acid sequence set forth as one of SEQ ID NO: 8, SEQ ID NO: 24, SEQ ID NO: 40, SEQ ID NO: 56, SEQ ID NO: 72, SEQ ID NO: 88, SEQ ID NO: 104, SEQ ID NO: 120, or SEQ ID NO: 136.

In additional embodiments, the monoclonal antibody includes a light chain variable domain comprising an amino acid sequence at least 90%, 91%, 92%, 93%, 94%, 95%, 96%, 97%, 98% or 99% identical to one of the amino acid sequence set forth as one of SEQ ID NO: 16, SEQ ID NO: 32, SEQ ID NO: 48, SEQ ID NO: 64, SEQ ID NO: 80, SEQ ID NO: 96, SEQ ID NO: 112, SEQ ID NO: 128 or SEQ NO: 144. In additional embodiments, the light chain variable domain includes at most 10, at most 9, at most 8, at most 7, at most 6, at most 5, at most 4, at most 3, at most two or at most one conservative amino acid substitutions in an amino acid sequence set forth as one of SEQ ID NO: 16, SEQ ID NO: 32, SEQ ID NO: 48, SEQ ID NO: 64, SEQ ID NO: 80, SEQ ID NO: 96, SEQ ID NO: 112, SEQ ID NO: 128 or SEQ NO: 144. In other embodiments, the monoclonal antibody includes a light chain variable domain comprising or consisting of one of the amino acid sequence set forth as SEQ ID NO: 16, SEQ ID NO: 32, SEQ ID NO: 48, SEQ ID NO: 64, SEQ ID NO: 80, SEQ ID NO: 96, SEQ ID NO: 112, SEQ ID NO: 128 or SEQ NO: 144.

In additional embodiments, the monoclonal antibody specifically binds a NV VP1 polypeptide and includes one of:
(a) a heavy chain variable domain including an amino acid sequence at least 90%, 91%, 92%, 93%, 94%, 95%, 96%, 97%, 98% or 99% identical to the amino acid sequence set forth as SEQ ID NO: 8 and a light chain variable domain including an amino acid sequence at least 90%, 91%, 92%, 93%, 94%, 95%, 96%, 97%, 98% or 99% identical to the amino acid sequence set forth as SEQ ID NO: 16;
(b) a heavy chain variable domain including an amino acid sequence at least 90%, 91%, 92%, 93%, 94%, 95%, 96%, 97%, 98% or 99% identical to the amino acid sequence set forth as SEQ ID NO: 24 and a light chain variable domain including an amino acid sequence at least 90%, 91%, 92%, 93%, 94%, 95%, 96%, 97%, 98% or 99% identical to the amino acid sequence set forth as SEQ ID NO: 32;
(c) a heavy chain variable domain including an amino acid sequence at least 90%, 91%, 92%, 93%, 94%, 95%, 96%, 97%, 98% or 99% identical to the amino acid sequence set forth as SEQ ID NO: 40 and a light chain variable domain including an amino acid sequence at least 90%, 91%, 92%, 93%, 94%, 95%, 96%, 97%, 98% or 99% identical to the amino acid sequence set forth as SEQ ID NO: 48;
(d) a heavy chain variable domain including an amino acid sequence at least 90%, 91%, 92%, 93%, 94%, 95%, 96%, 97%, 98% or 99% identical to the amino acid sequence set forth as SEQ ID NO: 56 and a light chain variable domain including an amino acid sequence at least 90%, 91%, 92%, 93%, 94%, 95%, 96%, 97%, 98% or 99% identical to the amino acid sequence set forth as SEQ ID NO: 64; and
(e) the heavy chain variable domain including an amino acid sequence at least 90%, 91%, 92%, 93%, 94%, 95%, 96%, 97%, 98% or 99% identical to the amino acid sequence set forth as SEQ ID NO: 72 and a light chain variable domain including an amino acid sequence at least 90%, 91%, 92%, 93%, 94%, 95%, 96%, 97%, 98% or 99% identical to the amino acid sequence set forth as SEQ ID NO: 80.

In further embodiments, the monoclonal antibody specifically binds a NoV polypeptide, and comprises one of
  (a) a heavy chain variable domain including an amino acid sequence at least 90%, 91%, 92%, 93%, 94%, 95%, 96%, 97%, 98% or 99% identical to the amino acid sequence set forth as SEQ ID NO: 88 and a light chain variable domain including an amino acid sequence at least 90%, 91%, 92%, 93%, 94%, 95%, 96%, 97%, 98% or 99% identical to the amino acid sequence set forth as SEQ ID NO: 96;
  (b) a heavy chain variable domain including an amino acid sequence at least 90%, 91%, 92%, 93%, 94%, 95%, 96%, 97%, 98% or 99% identical to the amino acid sequence set forth as SEQ ID NO: 104 and a light chain variable domain including an amino acid sequence at least 90%, 91%, 92%, 93%, 94%, 95%, 96%, 97%, 98% or 99% identical to the amino acid sequence set forth as SEQ ID NO: 112;
  (c) a heavy chain variable domain including an amino acid sequence at least 90%, 91%, 92%, 93%, 94%, 95%, 96%, 97%, 98% or 99% identical to the amino acid sequence set forth as SEQ ID NO: 120 and a light chain variable domain including an amino acid sequence at least 90%, 91%, 92%, 93%, 94%, 95%, 96%, 97%, 98% or 99% identical to the amino acid sequence set forth as SEQ ID NO: 128; and
  (d) a heavy chain variable domain including an amino acid sequence at least 90%, 91%, 92%, 93%, 94%, 95%, 96%, 97%, 98% or 99% identical to the amino acid sequence set forth as SEQ ID NO: 136 and a light chain variable domain including an amino acid sequence at least 90%, 91%, 92%, 93%, 94%, 95%, 96%, 97%, 98% or 99% identical to the amino acid sequence set forth as SEQ ID NO: 144.

In additional embodiments, the monoclonal antibody specifically binds a NV VP1 polypeptide and includes one of:
  (a) a heavy chain variable domain including the amino acid sequence set forth as SEQ ID NO: 8 and a light chain variable domain including the amino acid sequence set forth as SEQ ID NO: 16;
  (b) a heavy chain variable domain including the amino acid sequence set forth as SEQ ID NO: 24 and a light chain variable domain including the amino acid sequence set forth as SEQ ID NO: 32;
  (c) a heavy chain variable domain including the amino acid sequence set forth as SEQ ID NO: 40 and a light chain variable domain including the amino acid sequence set forth as SEQ ID NO: 48;
  (d) a heavy chain variable domain including the amino acid sequence set forth as SEQ ID NO: 56 and a light chain variable domain including the amino acid sequence set forth as SEQ ID NO: 64; and
  (e) the heavy chain variable domain including the amino acid sequence set forth as SEQ ID NO: 72 and the light chain variable domain including the amino acid sequence set forth as SEQ ID NO: 80.

In further embodiments, the monoclonal antibody specifically binds a NoV polypeptide, and comprises one of
  (a) a heavy chain variable domain including the amino acid sequence set forth as SEQ ID NO: 88 and a light chain variable domain including the amino acid sequence set forth as SEQ ID NO: 96;
  (b) a heavy chain variable domain including the amino acid sequence set forth as SEQ ID NO: 104 and a light chain variable domain including the amino acid sequence set forth as SEQ ID NO: 112;
  (c) a heavy chain variable domain including the amino acid sequence set forth as SEQ ID NO: 120 and a light chain variable domain including the amino acid sequence set forth as SEQ ID NO: 128; and
  (d) a heavy chain variable domain including the amino acid sequence set forth as SEQ ID NO: 136 and a light chain variable domain including the amino acid sequence set forth as SEQ ID NO: 144.

The antibodies including the HCDR sequences, LCDR sequences, VH sequences and VL sequences specified above can be neutralizing and/or can inhibit hemagglutination activity.

Antibody fragments are encompassed by the present disclosure, such as Fab, F(ab')$_2$, and Fv which include a heavy chain and light chain variable region and are capable of binding the epitopic determinant on IGF-II. These antibody fragments retain the ability to selectively bind with the antigen. The fragments can be included in a bispecific antibody. These antigen binding fragments include:
  (1) Fab, the fragment which contains a monovalent antigen-binding fragment of an antibody molecule, can be produced by digestion of whole antibody with the enzyme papain to yield an intact light chain and a portion of one heavy chain;
  (2) Fab', the fragment of an antibody molecule can be obtained by treating whole antibody with pepsin, followed by reduction, to yield an intact light chain and a portion of the heavy chain; two Fab' fragments are obtained per antibody molecule;
  (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;
  (4) Fv, a genetically engineered fragment containing the variable region of the light chain and the variable region of the heavy chain expressed as two chains; and
  (5) Single chain antibody (such as scFv), defined as a genetically engineered molecule containing the variable region of the light chain, the variable region of the heavy chain, linked by a suitable polypeptide linker as a genetically fused single chain molecule.
  (6) A dimer of a single chain antibody (scFV$_2$), defined as a dimer of an scFV. This has also been termed a "miniantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m610.27. In one group of embodiments, the antibodies have V$_H$ CDRs m610.27, or a combination of these CDRs, as discussed above.

In a further group of embodiments, the antibodies are Fv antibodies, which are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, *Academic Press*, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art (see above). Thus, one of skill in the art can readily review the sequences shown above, identify a conservative substitution, and produce the conservative variant using well-known molecular techniques.

EAds and bispecific antibodies comprising an eAd are provided herein. The eAd, or bispecific antibody can include the CDRs or the variable domain The antibodies or antibody fragments disclosed herein can be derivatized or linked to another molecule (such as another peptide or protein). In general, the antibody or portion thereof is derivatized such that the binding to the NoV polypeptide, such as a Norwalk virus polypeptide, such as VP1, is not affected adversely by the derivatization or labeling. For example, the antibody can be functionally linked, for example, by chemical coupling, genetic fusion, noncovalent association or otherwise to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody that specifically binds a NoV polypeptide, such as a NV polypeptide, such as VP1, can be labeled with a detectable moiety. Useful detection agents include fluorescent compounds, including fluorescein, fluorescein isothiocyanate, rhodamine, 5-dimethylamine-1-naphthalene-sulfonyl chloride, phycoerythrin, lanthanide phosphors and the like. Bioluminescent markers are also of use, such as luciferase, green fluorescent protein (GFP), or yellow fluorescent protein. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. Examples of radiolabels include, but are not limited to, the following radioisotopes or radionucleotides: $^3$H, $^{14}$C, $^{15}$N, $^{35}$S, $^{99}$Y, $^{99}$Tc, $^{111}$In, $^{125}$I, $^{131}$I. The radiolabel may be used for both diagnostic and therapeutic purposes.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibodies or antibody fragments disclosed herein can be derivatized or linked to another molecule (such as another peptide or protein). In general, the antibody or portion thereof is derivatized such that the binding to the NoV polypeptide, such as the NV polypeptide, is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company (Rockford, Ill.).

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Polynucleotides and Expression

Nucleotide sequences encoding an antibody that specifically binds a NoV polypeptide, such as a Norwalk virus polypeptide. The antibody can specifically bind VP1. Expression vectors are also provided for their efficient expression in cells (for example, mammalian cells).

Recombinant expression of an antibody generally requires construction of an expression vector containing a polynucleotide that encodes the antibody or antibody fragment. Replicable vectors are provided including a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of an antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Nucleic acid molecules (also referred to as polynucleotides) encoding the polypeptides provided herein (including, but not limited to antibodies) can readily be produced by one of skill in the art. For example, these nucleic acids can be produced using the amino acid sequences provided herein (such as the CDR sequences, heavy chain and light chain sequences), sequences available in the art (such as framework sequences), and the genetic code.

$V_H$ nucleic acid sequences are set forth as SEQ ID NOs: 146-149 and 154-158 and include degenerate variants thereof; $V_L$ nucleic acid sequences are set forth as SEQ ID NOs: 150-153 and 159-163, and include degenerate variants thereof. One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

Nucleic acid sequences encoding the antibodies that specifically bind a NoV polypeptide, including but not limited to VP1, such as that specifically bind a Norwalk virus polypeptide, such as VP1, can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

Any of the nucleic acids encoding any of the antibodies, $V_H$ and/or $V_L$, disclosed herein (or fragment thereof) can be expressed in a recombinantly engineered cell such as bacteria, plant, yeast, insect and mammalian cells. These antibodies can be expressed as individual $V_H$ and/or $V_L$ chain, or can be expressed as a fusion protein. An immunoadhesin can also be expressed. Thus, in some examples, nucleic acids encoding a $V_H$ and $V_L$, and immunoadhesin are provided. The nucleic acid sequences can optionally encode a leader sequence.

To create a single chain antibody, (scFv) the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ domains joined by the flexible linker (see, e.g., Bird et al., Science 242:423-426, 1988; Huston et al., Proc. Natl. Acad. Sci. USA 85:5879-5883, 1988; McCafferty et al., Nature 348:552-554, 1990). Optionally, a cleavage site can be included in a linker, such as a furin cleavage site.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an $IgG_1$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to NoV polypeptide, such as a NV polypeptide, such as VP1, and another antigen. The encoded $V_H$ and $V_L$ optionally can include a furin cleavage site between the $V_H$ and $V_L$ domains.

It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. Once the expression vector is transferred to a host cell by conventional techniques, the transfected cells are then cultured by conventional techniques, such as to produce an antibody. Thus, host cells are provided containing a polynucleotide encoding an antibody or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells. In one embodiment, human cell lines are of use. In one embodiment, the human cell line PER.C6. (Crucell, Netherlands) can be used. Additional cell lines which may be used as hosts for expression of recombinant antibodies include, but are not limited to, insect cells (e.g. Sf21/Sf9, *Trichoplusia ni* Bti-Tn5b1-4) or yeast cells (e.g. *S. cerevisiae, Pichia*, U.S. Pat. No. 7,326,681), plant cells (US Published Patent Application No. 20080066200); and chicken cells (PCT Publication No. WO2008142124).

The host cell can be a gram positive bacteria including, but not limited to, *Bacillus, Streptococcus, Streptomyces, Staphylococcus, Enterococcus, Lactobacillus, Lactococcus, Clostridium, Geobacillus*, and *Oceanobacillus*. Methods for expressing protein in gram positive bacteria, such as *Lactobaccillus* are well known in the art, see for example, U.S. Published Patent Application No. 20100/080774. Expression vectors for *lactobacillus* are described, for example in U.S. Pat. No. 6,100,388, and U.S. Pat. No. 5,728,571. Leader sequences can be included for expression in *Lactobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

One or more DNA sequences encoding the antibody or fragment thereof can be expressed in vitro by DNA transfer into a suitable host cell. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

The expression of nucleic acids encoding the isolated proteins described herein can be achieved by operably linking the DNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the immunoconjugates, effector moieties, and antibodies of the present disclosure can also be constructed in whole or in part using standard peptide synthesis well known in the art.

Once expressed, the recombinant immunoconjugates, antibodies, and/or effector molecules can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5-fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis,* 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicyclohexylcarbodimide) are well known in the art. Once an antibody molecule has been produced, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies or fragments thereof may be fused to heterologous polypeptide sequences (referred to herein as "tags") described above or otherwise known in the art to facilitate purification.

Compositions and Therapeutic Methods

Methods are disclosed herein for the prevention or treatment of a NoV infection. Included within the NoVs are at least 5 genogroups (GI-GV), separated by nucleic acid and amino acid sequences, which comprise 15 genetic clusters. Methods are provided for the prevention and/or treatment of NoVs from any of these groups. Non-limiting examples of NoVs include NV (NV, see, for example, GENBANK® Accession No. M87661, NP_056821), Southampton virus (SHV, see, for example, GENBANK® Accession No. L07418), Desert Shield virus (DSV, see, for example, GENBANK® Accession No. U04469), Hesse virus (HSV), Chiba virus (CHV, see, for example, GENBANK® Accession No. AB042808), Hawaii virus (HV, see, for example, GENBANK® Accession No. U07611), Snow Mountain virus (SMV, see, for example, GENBANK® Accession No. U70059), Toronto virus (TV, Leite et al., Arch. Virol. 141: 865-875), Bristol virus (BV), Jena virus (JV, see, for example, GENBANK® Accession No. AJ01099), MD145-12 virus (MD145-12, see, for example, GENBANK® Accession No. AY032605), Seto virus (SV, see, for example, GENBANK® Accession No. AB031013), Camberwell (CV, see, for example, GENBANK® Accession No. AF145896), Lordsdale virus (LV, see, for example, GENBANK® Accession No. X86557), Grimsby virus (GrV, see, for example, GENBANK® Accession No. AJ004864), Mexico virus (MXV, see, for example, GENBANK® Accession No. U22498), Boxer (see, for example, GENBANK® Accession No. AF538679), C59 (see, for example, GENBANK® Accession No. AF435807), VA115 (see, for example, GENBANK® Accession No. AY038598), BUDS (see, for example, GENBANK® Accession No. AY660568), MOH (see, for example, GENBANK® Accession No. AF397156), Parris Island (PiV; see, for example, GENBANK® Accession No. AY652979), VA387 (see, for example, GENBANK® Accession No. AY038600), VA207 (see, for example, GENBANK® Accession No. AY038599), and Operation Iraqi Freedom (see, for example, OIF, GENBANK® Accession No. AY675554). In some embodiments, methods are provided for the treatment and/or prevention of Genogroup I NV. In some embodiments, methods are provided for the treatment and/or prevention of Genogroup II NV. In some non-limiting examples, methods are provided for the treatment and/or prevention of a NV infection. In other non-limiting examples, methods are provided for the treatment and/or prevention of a MD145-12 infection.

Prevention can include inhibition of infection with the NoV, such as a Norwalk virus. In some embodiments, the methods include contacting a cell with an effective amount of the monoclonal antibodies disclosed herein that specifically binds a NoV polypeptide, such as a Norwalk virus polypeptide. In some embodiments, the antibody specifically binds VP1, or an antigen binding fragment thereof. The method can also include administering to a subject a therapeutically effective amount of a monoclonal antibody, or a nucleic acid encoding the antibody. Neutralizing MAbs against NoVs can be used as emergency prophylaxis to protect individuals in the proximity of a developing NoV outbreak, or when encountering an increased risk of exposure. Thus, the methods can include selecting a subject at risk of exposure to a NoV.

In other embodiments, methods are disclosed for ameliorating one or more symptoms associated with a Norovirus infection, such as a Norwalk virus infection. Generally, the method includes administering an antibody or antibody (antigen-binding) fragment that specifically binds a NoV polypeptide, such as a Norwalk virus polypeptide. The antibody can specifically bind VP1. In some embodiments, the disclosed antibodies can be used in treatment to alleviate chronic NoV gastroenteritis in debilitated or immunocompromised individuals. Thus, the method can include selecting a subject with gastroenteritis. In some examples, the subject is immunocompromised. In some embodiments, the subject is a premature infant. In some embodiments, an individual is debilitated by chemotherapy for cancer. In some embodiments, an elderly individual with prolonged NoV disease can be treated.

The NoV infection does not need to be completely eliminated for the composition to be effective. For example, a composition can decrease the NoV infection in a population by a desired amount, for example by at least 10%, at least 20%, at least 50%, at least 60%, at least 70%, at least 80%, at least 90%, at least 95%, at least 98%, or 100%, as compared to the rate of infection in the absence of the composition. In addition, a composition can decrease viral titer by at least 10%, at least 20%, at least 50%, at least 60%, at least 70%, at least 80%, at least 90%, at least 95%, at least 98%, or 100% in a subject.

In example, the subject is also administered an effective amount of an additional agent, such as anti-viral agent. The methods can include administration of one on more additional agents known in the art. The subject can hydrated and administered balancing electrolytes.

A therapeutically effective amount of a NoV-specific (or Norwalk virus specific) antibody or antigen binding fragment (or the nucleic acid encoding the antibody or antigen binding fragment), or nucleic acid, will depend upon the severity of the disease and/or infection and the general state of the patient's health. A therapeutically effective amount of the antibody can provide either subjective relief of a symptom(s) or an objectively identifiable improvement as noted by the clinician or other qualified observer. As noted above, these compositions can be administered in conjunction with another therapeutic agent, either simultaneously or sequentially. For any application, the antibody, antigen binding fragment, or nucleic acid encoding the antibody or antigen binding fragment can be combined with anti-viral therapy.

In one embodiment, administration of the antibody (or nucleic acid encoding the antibody) results in a reduction in the establishment of a virus infection and/or reducing subsequent disease progression in a subject. A reduction in the establishment of NoV infection, such as a Norwalk virus infection, and/or a reduction in subsequent disease progression can encompass a statistically significant reduction in viral activity. In some embodiments, methods are disclosed for treating a subject with a NoV infection, such as a Norwalk virus infection. These methods include administering to the subject a therapeutically effective amount of an antibody, or a nucleic acid encoding the antibody, thereby preventing or treating the viral infection.

Single or multiple administrations of the compositions including the antibody, antigen binding fragment, or nucleic acid encoding the antibody or antigen binding fragment, that are disclosed herein, are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Compositions are provided that include one or more of the antibodies that specifically bind a NoV polypeptide, such as a Norwalk virus polypeptide, such as an antibody that specifically binds VP1, or antigen binding fragments of any of these antibodies, and nucleic acids encoding these antibodies (and antigen binding fragments) that are disclosed herein in a carrier. The compositions can be prepared in unit dosage forms for administration to a subject. The amount and timing of administration are at the discretion of the treating physician to achieve the desired purposes. The antibody and/or nucleic acid can be formulated for systemic or local administration. In one example, the antibody and/or nucleic acid is formulated for parenteral administration, such as intravenous administration. In some embodiments, administration is intramuscular.

Compositions also can be formulated for enteric delivery. Various studies have been made on a method of releasing or delivering a drug selectively to a specific site in the intestine. In addition to classic methods of using enteric-coated preparations or sustained release preparations (Chemical & Pharmaceutical Bulletin, 40, 3035-3041, 1992), enteric-coated sustained-release preparations and time-limited release enteric-coated preparations have been proposed (Japanese Patent No. 3185206, and PCT Publication No. WO 01/23000).

Active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the immunogens or antibodies can be prepared by such methods as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556. The reverse-phase evaporation method can be used with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described, for example, in Martin et al., J. Biol. Chem., 257:286-288 (1982) via a disulfide interchange reaction.

The compositions for administration can include a solution of the antibody that specifically binds a NoV polypeptide, such as VP1, dissolved in a pharmaceutically acceptable carrier, such as an aqueous carrier. The compositions for administration can include a solution of the antibody that specifically binds a NV polypeptide, such as VP1, dissolved in a pharmaceutically acceptable carrier, such as an aqueous carrier. A variety of aqueous carriers can be used, for example, buffered saline and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs. In some embodiments, administration is intravenous.

Controlled-release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A typical pharmaceutical composition for intravenous administration includes about 0.1 to 10 mg/kg of antibody per day, or 0.5 to 15 mg/kg of antibody per day. Dosages from 0.1 up to about 100 mg/kg per subject per day may be used, particularly if the agent is administered to a secluded site and not into the circulatory or lymph system, such as into a body cavity or into a lumen of an organ. Exemplary doses include 1 to 10 mg/kg, such as 2 to 8 mg/kg, such as 3 to 6 mg/kg. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.1 to 10 mg/kg or 0.5 to 15 mg/kg of body weight. Exemplary doses include 1 to 10 mg/kg, such as 2 to 8 mg/kg, such as 3 to 6 mg/kg. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding the antibody or an antigen binding fragment thereof can be administered to a subject in need thereof. One approach to administration of nucleic acids is direct immunization with plasmid DNA, such as with a mammalian expression plasmid. The nucleotide sequence encoding the antibody or fragment thereof can be placed under the control of a promoter to increase expression of the molecule. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids to an organism. The methods include liposomal delivery of the nucleic acids.

In another approach to using nucleic acids, an antibody or antigen binding fragment thereof can also be expressed by attenuated viral hosts or vectors or bacterial vectors, which can be administered to a subject. Recombinant vaccinia virus, adeno-associated virus (AAV), herpes virus, retrovirus, cytomegalovirus, poxvirus or other viral vectors can be used to express the antibody. For example, vaccinia vectors are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding the antibody or an antigen binding fragment thereof is introduced directly into cells. For example, the nucleic acid can be loaded onto gold microspheres by standard methods and introduced into the skin by a device such as Bio-Rad's Heliosa Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In some examples, a subject is administered the DNA encoding the antibody or antibody binding fragments thereof to provide in vivo antibody production, for example using the cellular machinery of the subject Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed antibody, or antibody binding fragments thereof can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding a disclosed antibody, or antibody binding fragments thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

Diagnostic Methods and Kits

A method is provided herein for the detection of the expression of a NoV polypeptide, such as a Norwalk virus polypeptide, in vitro or in vivo. In one example, expression of the NoV polypeptide, such as the Norwalk virus polypeptide, is detected in a biological sample, and can be used to an infection with the virus. The polypeptide can be VP1. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid, nasopharyngeal secretions or urine.

In one embodiment, methods are provided for detecting the presence of a NoV, such as a Genogroup I or Genogroup II NoV. In some embodiments, methods are provided for detecting the presence of a Norwalk virus or a MD145-12 virus. The presence of the NoV is detected in a sample suspected of containing the virus, wherein the method includes contacting the sample with an antibody disclosed herein, and determining binding of the antibody to the virus in the sample wherein binding of the antibody to virus in the sample is indicative of the presence of the virus in the sample. In one embodiment, the sample is a biological sample. In some examples, the sample is a stool sample. In other embodiments, the sample is an environmental sample. In some embodiments, the method distinguishes a particular NoV from other NoV, distinguishes NV from other NoV, or distinguishes MD145-12 from other NoV.

NoVs are divided into five distinct genogroups (GI-GV) based on VP1 sequence similarity. Virus strains from GI and GII are responsible for most human infections, and these genogroups are further subdivided into more than 25 different genotypes (Zheng et al., 2006, Virology 346:312-23). In some embodiments, methods are provided for detecting or distinguishing among a GI, GII, GIII, GIV, or GV NoV, such as a GI or a GII NoV. In other embodiments, methods are provided for detecting or distinguishing NV in a sample, or detecting or distinguishing MD145-12 in a sample. The method includes contacting the sample with an antibody disclosed herein that specifically binds the NoV or NV, and determining binding of the antibody to the virus in the sample. In some embodiments, binding of the antibody to virus in the sample is indicative of the presence of a GI NV, such as GI.1 NV in the sample. In one embodiment, the sample is a biological sample. In some examples, the sample is a stool sample. In other embodiments, the sample is an environmental sample.

In several embodiments, a method is provided for detecting a NoV infection, such as Norwalk virus infection in a subject. The disclosure provides a method for detecting a NoV in a biological sample, wherein the method includes contacting a biological sample with the antibody under conditions conducive to the formation of an immune complex, and detecting the immune complex, to detect the presence of a NoV polypeptide, such as a Norwalk virus polypeptide in the biological sample. In some embodiments, NV VP1, is detected in the biological sample. In another example, detection of the virus in the sample confirms a diagnosis of a NoV infection, in a subject.

In some specific non-limiting examples, the monoclonal antibody specifically binds a NV polypeptide, such as VP1. In these examples, the method detects a GI NV infection in the subject, such as, but not limited to, a GI.1 NV infection.

The detection of a NoV can be achieved, for example, by contacting a sample to be tested, optionally along with a control sample, with the antibody under conditions that allow for formation of a complex between the antibody and the virus. Complex formation is then detected (e.g., using an ELISA). When using a control sample along with the test sample, complex is detected in both samples and any statistically significant difference in the formation of complexes between the samples is indicative of the presence of a NoV in the test sample.

In some embodiments, the disclosed antibodies are used to test vaccines. For example to test if a vaccine composition can induce neutralizing antibodies to a NoV, such as Norwalk virus. Thus provided herein is a method for detecting testing a vaccine, wherein the method includes contacting a sample containing the vaccine, such as an NoV polypeptide, for example a Norwalk virus polypeptide, with the antibody under conditions conducive to the formation of an immune complex, and detecting the immune complex, to confirm the vaccine will be effective. In one example, the detection of the immune complex in the sample indicates that vaccine component, such as such as an NoV antigen (for example a Norwalk virus antigen, such as VP1) assumes a conformation capable of inducing neutralizing antibodies.

In some embodiments, an antibody is directly labeled with a detectable label. In another embodiment, the antibody that binds the NoV (the first antibody) is unlabeled and a second antibody or other molecule that can bind the antibody that binds the NoV polypeptide is utilized. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

The immunoassays and method disclosed herein can be used for a number of purposes. Kits for detecting n NoV polypeptide will typically comprise an antibody that binds a NoV polypeptide, such as a Norwalk virus polypeptide, for example, any of the antibodies disclosed herein. In some embodiments, an antibody fragment, such as an Fv fragment or a Fab is included in the kit. In a further embodiment, the antibody is labeled (for example, with a fluorescent, radioactive, or an enzymatic label).

In one embodiment, a kit includes instructional materials disclosing means of use. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting the NoV polypeptide, such as a Norwalk virus polypeptide, such as VP1 in a biological sample generally includes the steps of contacting the biological sample with an antibody which specifically reacts, under immunologically reactive conditions, to the viral polypeptide. The antibody is allowed to specifically bind under immunologically reactive conditions to form an immune complex, and the presence of the immune complex (bound antibody) is detected directly or indirectly.

The following examples are provided to illustrate certain particular features and/or embodiments. These examples should not be construed to limit the disclosure to the particular features or embodiments described.

EXAMPLES

NoVs are important agents of human gastroenteritis and the infections are associated with a significant disease burden. Yet there are no disease interventions available. Despite substantial advances in developing NoV vaccines based on VLPs (see, for example, Atmar et al., N. Eng. J. Med. 365: 2178-2187, 2011; Herbst et al., 2010, Expert Rev Vaccines 9:299-307), there are several remaining challenges to address in NoV vaccine development, including the duration of immunity, rapidly evolving new variant strains, and an incomplete understanding of the immune correlates of protection. Limited cross-protection between NoV genotypes within the same genogroup (GII.4 variant) and a lack of cross-protection between genogroups are observed (Wyatt et al., 1974, J Infect Dis 129:709-14).

As an alternative or complement to vaccines, passive immunization with anti-NoV MAbs can provide immediate protection against NoV infection in high-risk populations. As disclosed herein, five NV-specific antibodies and four anti-NoV-specific antibodies were isolated from immunized chimpanzees. It was demonstrated that these antibodies were able to block the binding of rVLP of NoV to HBGA carbohydrates, a known binding ligand for NoV in the intestinal mucosa. As proof of concept, on one study of antibody efficacy in a chimpanzee was performed. The antibodies disclosed herein can be used in emergency prophylaxis and treatment of NoV infection.

Example 1

Materials and Methods

Immunization of Chimpanzees with NV and Construction of Combinatorial Fab Antibody Library:

Chimpanzee 1618 was inoculated orally with $10^1$ 50% chimpanzee infectious doses ($CID_{50}$) of prototype NV in a stool filtrate (preparation 8 FIIa F/T, 1976) and were boosted intravenously with NV recombinant viral like particles (rV-LPs). Bone marrow was aspirated from the chimpanzee at days 60, 74 and 88 after boost. Bone marrow-derived lymphocytes were prepared by centrifugation on a Ficoll-Hypaque gradient (GE Healthcare, Piscataway, N.J.) and were used for construction of a combinatorial Fab phage display library as described (Chen et al., 2007, J Virol 81:8989-95; Chen et al., 2006, Proc Natl Acad Sci USA 103:1882-7). A Fab phage display library containing γ1 heavy chain and κ, λ light chain with a diversity of >$10^8$ was constructed.

Panning of Phage Library and Selection of NV-Specific Fabs:

Phages were produced from the library as described (Chen et al., 2006, supra) and panned by affinity binding on NV rVLPs adsorbed to a 96-well ELISA plate. For each cycle of panning, 100 μl of NV rVLPs at 5 μg/ml in PBS was used to coat each well of an ELISA plate and specific phages were selected by incubating $10^{12}$ phages with the coated VLP. The NV-specific Fab clones were enriched by three cycles of panning against the NV rVLP. After panning, 96 single phage-Fab clones were cultured in a 96-well plate for phage production. The resulting phages were screened for specific binding to NV rVLP by phage ELISA (13). Clones that bound to the NV rVLP, but not to BSA, were scored as NV-specific clones.

Isolation of NV-Specific Antibodies by Immortalization of Memory B Cells:

Peripheral blood (50 ml) was collected from the chimpanzee immunized with NV rVLPs. The PBMCs were isolated by Ficoll Hypaque density gradient centrifugation. B-cells were first enriched from PBMC by using BD IMAGO human B lymphocyte enrichment set (BD Biosciences, San Jose, Calif.) and B cells were then incubated with PE-labeled anti-CD27 (Invitrogen), PE-Cy5-labeled anti-CD22 (Invitrogen Life technologies, Grand Island, N.Y.), ALEXA® 700-labeled anti-CD38 (eBioscience, San Diego, Calif.) and Atto 633-labeled anti-IgG Ab (Jackson Immunoresearch, West Grove, Pa.) for 30 min at 4° C. The $IgG^+$, memory B-cells were isolated by FACS sorting based on positivity for CD27, CD22 and IgG markers and negativity for CD38. The FACS sorted cells were used immediately for the B cell immortalization.

The memory B-cells were cultured in U-bottom 96-well plates (Nunc, Rochester, N.Y.) at 40 cells per well in RPMI 1640 medium supplemented with 10% fetal bovine serum, 50 U/ml penicillin, 50 μg/ml streptomycin (all from Invitrogen Life Technologies). The cells were immortalized by maintenance for three weeks in the presence of $1 \times 10^5$ irradiated MRC-5 feeder cells (ATCC, Manassas, Va.), 30% EBV-containing supernatant of the B95-8 cell line and 1 μg/ml CpG2006. The supernatant fluid of each well was screened by ELISA for binding to NV rVLPs as described above. The total RNA was extracted from the cells producing Abs specific to NV VLPs using the ZR RNA MicroPrep (Zymo Research, Irvine, Calif.). The cDNA synthesis and PCR amplification of $V_H$ and $V_L$ genes were carried out as described for phage library construction (Chen et al., 2006, supra).

DNA Sequence Analysis of Specific Fabs:

The genes coding for the variable regions of the heavy (VH) and light (VL) chains of NV-specific Fabs were sequenced. Fabs with distinct VH and VL sequences were regarded as separate Fab clones. The presumed immunoglobulin family usage, germline origin, and somatic mutations were identified by comparing to those deposited in the IMGT sequence database (imgt.cines.fr).

Production of Fabs and IgGs:

Constructs for Fab and full-length IgG1 expression were made as described (Chen et al., 2006, supra). The histidine-tagged Fab was expressed in E. coli and was affinity-purified on a nickel column. IgG was expressed in transiently transfected 293T mammalian cells and purified on a Protein A column. Both Fab and IgG were further purified through a cation-exchange SP column (GE Healthcare). Purities of the Fab and IgG were evaluated by sodium dodecyl sulfate-polyacrylamide gel electrophoresis (SDS-PAGE) and the protein concentrations were determined by optical density measurements at 280 nm, with 1.35 A280 corresponding to 1.0 mg/ml.

Enzyme-Linked Immunosorbant Assay (ELISA):

Wells in a 96-well ELISA plate were coated with 100 μl of NV-VLP or other NoV-VLP at a concentration of 1.5 μg/ml, followed by incubation with 3% milk in phosphate buffered saline (PBS) for blocking. After washing, the plate was incubated with 3-fold serially-diluted anti-NV Fabs for 2 h at room temperature. After washing, the plate was incubated for 1 h with horseradish peroxidase-conjugated antibodies against human Fc. The color was developed by adding tetramethylbenzidine reagent (KPL, Gaithersburg, Md.) and stopped with H2SO4 after 10 min. The optical density (OD) at 450 nm was read in an ELISA plate reader. The data were plotted and the dose-response curves were generated with Prism software (Graphpad Software Inc, San Diego, Calif.).

Affinity Measurement by Surface Plasmon Resonance (SPR):

Binding kinetics of antibody Fab fragments to NV rVLPs was assessed by SPR using a Biacore 1000 (GE Healthcare). Running buffer contained 10 mM Hepes, pH 7.4, 150 mM NaCl, and 0.005% Tween-20 (HBS-EP buffer). NV rVLPs were coupled to the surface of a CM5 chip using the manufacturer-recommended protocol for amine coupling. Briefly, a 7 minute injection at 10 μl/min of a mixture of 0.4 M 1-ethyl-3-(3-dimethylaminopropyl) carbodiimide (EDC) and 0.1 M N-hydroxysulfosuccinimide (NHS) was used to activate the surface, then 25 μg/ml NV rVLPs in 10 mM acetate buffer, pH 4.5 was injected across the surface to achieve 200 RU, followed by deactivation of the surface by a 7 mM injection of 1 M ethanolamine at 10 μl/min Fabs at a concentration series of 1, 2.5, 5, 7.5 and 10 nM was passed over the NV rVLP surface for 2 min at 30 μl/min. Following dissociation for 6 min at 30 μl/min, the surface was regenerated by injecting a solution of Gentle Ag/Ab Elution Buffer, pH 6.6 (Thermo Scientific, Rockford, Ill.) supplemented with 0.01% (v/v) TRITON®-X 100 (Sigma, St. Louis, Mo.) for 1 min at 50 μl/min Data were analyzed with BIACORE® software (version 2.1.2) using the Langmuir model.

Competitive Surface Plasmon Resonance (SPR:

A cross-competition between Fabs was carried out by SPR. NV rVLPs were coupled to the surface of a CM5 chip as described above to achieve approximately 200 RU. All Fabs were tested at a concentration of 100 nM. The first Fab was injected and observed for the binding of analyte to ligand via sensorgram. When the surface was saturated, the second Fab was injected immediately and the binding activity was observed. The surface was regenerated and the order of injection of the Fabs was reversed to perform a two-way competition. This procedure was repeated for all Fabs with all possible binary combinations, and the binding signal for each pair of Fabs was recorded and analyzed. An increase in binding signal above 10% following injection of the second Fab was defined as an absence of competition between the two Fabs.

Epitope Mapping by Immunoprecipitation:

To express NV VP1 mutants with consecutive N-terminal deletions in vitro, the corresponding truncated ORF2 DNA fragments were PCR-amplified using the ELONGASE® Amplification System (Invitrogen) from plasmid pNV101 (Fernandez-Vega, 2004, J Virol 78:4827-37). The PCR-employed sense primers included a T7 RNA polymerase promoter sequence followed by a short noncoding sequence (GGGAACAGACCACC, SEQ ID NO: 145), AUG codon and in-frame sequence of the NV ORF2 region of interest. The antisense primer contained sequence complementary to the 3'-end of the NV ORF2. To express the NV VP1 mutants with C-terminal deletions, the DNA fragments were amplified using a sense primer that contained the T7 RNA polymerase promoter and sequence corresponding to the beginning of the ORF2 and antisense primers that contained engineered in-frame terminator codon and sequence complementary to the varying regions of the 3'-end part of the ORF2.

The amplified DNA fragments were agarose gel-purified and used as templates in a coupled transcription and translation reaction (TNT® T7 Quick for PCR DNA, Promega, Inc., Madison, Wis.). For radiolabeling of synthesized proteins, [$^{35}$S]-methionine (>1000 Ci/mmol) from Perkin Elmer (Waltham, Mass.) was used at a concentration of 0.4 mCi/ml.

Immunoprecipitation of the radiolabeled NV VP1 protein and its truncated versions from in vitro translation mixtures was performed according to the protocol described previously (Simmonds, 2005, Hepatology 42:962-73) with minor modifications. Briefly, after normalization for protein expression levels, 5- to 15 µl aliquots of the TNT translation reactions were diluted with 50 µl of RIPA buffer (50 mM Tris-HCl, pH 7.5, 0.15 M NaCl, 1% triton X-100, 0.6% sodium deoxycholate) without SDS. The proteins were incubated for one hour at room temperature with either recombinant Fab or MAb (IgG) at a concentration of 10 µg/ml, and immune complexes were precipitated with Protein G beads (Amersham Biosciences, Piscataway, N.J.) Immunoprecipitation of the Fab complexes was enhanced by an additional one hour-incubation with anti-human Fab IgG at 4 µg/ml (Jackson ImmunoResearch). Binding, washing and elution steps were carried out as described previously (Simmonds, 2005, supra). The eluted proteins were resolved by SDS-PAGE in a gradient 4-20% Tris-glycine gel (Invitrogen) and the bands corresponding to the radiolabeled immunoprecipitated proteins were detected by autoradiography after exposure of the dried gel to X-ray film (Eastman Kodak Co., Rochester, N.Y.)

Yeast-Surface Display of VP1:

The gene encoding NV full-length VP1 (530 amino acid residues) was amplified by PCR with addition of an NheI site at the 5'-end and a SalI site at the 3'-end. After digestion with NheI and SalI, the gene was cloned into yeast expression vector pCTCON2 so that the N-terminus of the VP1 was fused with a yeast protein, Aga2p through a short flexible linker and the C-terminus was tagged with c-myc. The construct was confirmed by sequencing and designated NVVP1-pCTCON2.

Yeast transformation, culture and expression were carried out essentially as described (Makiya et al., 2012, Biochem Biophys Res Commun 417:324-9). In brief, yeast EBY100 was transformed with NVVP1-pCTCON2 and selected on SDCAA agar plates. Protein expression was induced by culturing yeast in SGCAA medium at 22° C. for 48 h with shaking. Cells were harvested, washed and incubated with anti-c-myc antibody followed by Alexa Fluor 488 goat anti-chicken IgG for monitoring the VP1 expression, or incubated with mouse ant-NV MAb NV4 and chimp anti-NV Fabs of B7, D9, E4 and G4, respectively, followed by anti-mouse IgG DyLight 649 or anti-human Fab DyLight 649 for determining antibody binding. The labeled cells were analyzed on a BD FACS Canto II flow cytometer.

Site-Directed Mutagenesis of VP1 Gene of NV:

To convert part of the VP1 sequence from Norwalk to SW2007 (access number FJ384783)(34), six primer pairs were designed to introduce single G365N, V370I, I376V and Y410F mutations as well as double (G365N/V370I, V370I/I376V and G365N/I376V) mutations. In addition, a construct was generated with a triple (G365N/V370I/I376V) mutation Site-directed mutagenesis of pCI-Norwalk (VP1) was performed by using the QUIKCHANGE® Site-Directed Mutagenesis Kit (Stratagene, La Jolla, Calif.), and complementary forward and reverse primers that carried the nucleotide mutations. The restriction enzyme Dpn I (10 U/µl) was used to digest the parental DNA. Each of the mutated products was transformed into Epicurian Coli XL1-Blue supercompetent cells (Stratagene). Transformed cells were grown overnight on LB plates with carbenicillin (50 µg/ml), and individual colonies were used for plasmid amplification. The resulting plasmids were subjected to sequence analysis to verify the entire VP1 coding region and to confirm the presence of the introduced mutations.

Immunofluorescence Microscopy:

Vero cells were plated in 96-well plates at 80,000 cells/well, and infected with modified vaccinia T7 virus (1 PFU/cell) for 1 hour. After infection, cells were transfected with 400 ng/well of each DNA construct with Lipofectamine 2000 (Invitrogen) following the manufacturer's recommendations. Cells were incubated for 24 hours and fixed with cold methanol for 20 min Each Fab was used at a concentration of 5 µg/mL. Goat anti-human immunoglobulin G, F(ab')$_2$ conjugated with DyLight 549 (Jackson ImmunoResearch) was used for detection. Expression of VP1 was confirmed with a NoV-specific cross-reactive MAb (1:200 dilution), developed in mouse and goat anti-mouse immunoglobulin G (H+L) conjugated with Alexa Fluor 594 (Molecular Probes-Invitrogen, Carlsbad, Calif.). Cells transfected with a vector expressing GFP served as negative control for the specific Fab binding.

Protein Modeling:

The solved structure of the VP1 of NV (GI.1) (Protein Data Bank [PDB] accession number (1IHM) was used to identify the residues involved in the binding with G4 Fab and visualized by using MacPyMol (DeLano Scientific LLC).

Blocking of NV Hyperimmune Serum by Fabs:

The blocking activity of each Fab was examined by ELISA (Parra et al., 2012, J Virol 86:7414-26). Briefly, 96-well polyvinyl microtiter plates were coated with 0.5 µg/mL of NV rVLPs and incubated overnight at 4° C. Wells were washed with PBS-T and blocked with 1% BSA for 1 h at RT. 10 µg/mL of each Fab were absorbed for 2 h at RT, and wells were washed with PBS-T. A 10-fold serial dilution of a NV hyperimmune serum was incubated for 1 h at RT. The binding of hyperimmune serum to the VLP antigen was detected with HRP-conjugated goat anti-guinea pig immunoglobulin G (1:2,000) and 2,2'-azino-bis(3-ethylbenzthiazoline-6-sulphonic acid) (KPL).

HBGA Binding Blocking Assay:

The ability of antibodies to block the binding of NV rVLPs to synthetic HBGA H type 1 (H1) carbohydrate was determined as described (Bok, 2011, Proc Natl Acad Sci USA 108:325-30). Briefly, IgGs were two-fold serially diluted and incubated 2 h with 1.5 µg/mL NV rVLP, and the IgG-NV VLP mixture was then transferred into NeutriAvidin-coated plates (Pierce) containing biotinylated H1 carbohydrate (Glycotech) and incubated for 1 h. The binding of captured NV VLP was determined by incubation with guinea pig anti-NV hyperimmune serum (1:2,000 dilution), followed by incubation with a peroxidase-conjugated goat anti-guinea pig serum (1:2,000 dilution; KPL). The reaction was visualized with peroxidase substrate 2,2'-azino-bis(3-ethylbenzthiazoline-6-sulphonic acid, ABTS; KPL) and read at 405 nm with a Dynex Technologies Revelation 4.25 plate reader (Dynatech). All incubations were performed at room temperature. The 50% blocking antibody titer (BT50) was defined as the reciprocal of the lowest antibody dilution tested that blocked at least 50% of binding compared with that in the absence of antibody pretreatment (control binding).

Hemagglutination Inhibition Assay (HAI):

Inhibition of the hemagglutination activity of NV rVLPs by antibodies was determined as described (Czako et al., 2012, Clin Vaccine Immunol 19:284-7; Hutson et al., 2003, J Virol 77:405-1). Briefly, serial dilutions of the MAbs were incubated with Norwalk rVLP (80 ng of VLP or 16 HA units) in V bottomed 96-well plates and incubated for 1 hour at room temperature. Fifty µl of 0.75% type 0-human erythrocytes were added to the plate and incubated for 2 hour at 4° C. The HAI titer was defined as the reciprocal of the highest dilution of antibody that completely inhibited hemagglutination by the viral antigen.

Antibody-Mediated NV Neutralization in a Chimpanzee Model:

Monoclonal antibody NV-D8 (1 mg) was incubated with 1 CID of NV (8fIIa) for 1 hour at room temperature followed by an overnight incubation at 4° C. The following day, a chimpanzee was inoculated intravenously with 1.5 ml of the antibody-virus mixture. Stool samples from the chimpanzee were collected daily from 1 day pre-inoculation until 1 week after the virus genome was no longer detected in stools as measured by a NoV-specific qRT-PCR. The chimpanzee was observed for the appearance of clinical signs of gastroenteritis, including vomiting, diarrhea, and malaise, and was monitored weekly for elevation of hepatic enzymes. Whole blood samples were collected pre-inoculation and every other week until the termination of the study (four weeks after NoV shedding in stools was no longer detected in the control animals).

Example 2

Isolation and Characterization of NV-Specific Fabs

Figure 1A:
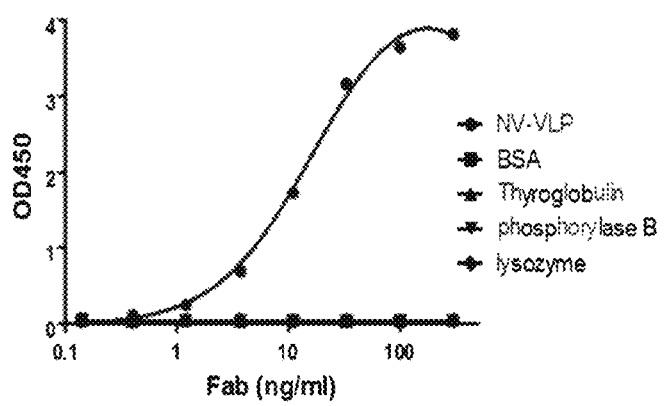
FIGS. 1A-1B. Binding specificities of anti-NV Fabs. (A) Binding in response to different concentrations of D8 Fab (a representative clone) on NV rVLP, or unrelated proteins, bovine serum albumin (BSA), thyroglobulin, lysozyme, and phosphorylase b was measured by ELISA with antigens directly attached to the solid phase. (B) The binding profile of Fab B7, D8, E5, G4 and F11 at concentration of 100 ng/ml on rVLP from NV (GI.1), SW-2007 (GI.1) and Hawaii (GII.1) and MD-145 (GII.4) that were attached on the solid phase at 1.5 µg/ml was measured by ELISA. OD, optical density, measured at 450 nm.

A phage Fab display library constructed from chimpanzees immunized with NV was panned for three cycles against NV rVLPs. The phage-Fab clones specific to NV were identified by phage ELISA. The sequencing analysis of the variable domain of heavy (VH) and light (VL) chains showed that four unique clones, B7, D8, E5 and G4, specific to NV were recovered. By immortalization of memory B-cells, an additional clone, F11 was recovered. These positive clones were subsequently converted to produce soluble Fabs. Each soluble Fab was confirmed for its specific binding to NV as they only bound to NV rVLPs, but not to BSA, phosphorylase b, thyroglobulin, or lysozyme. The ELISA binding profile of a representative Fab is shown in FIG. 1A.

Figure 1B:
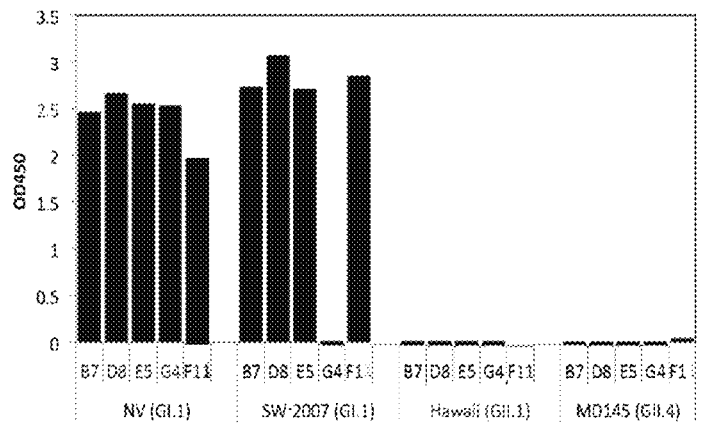

To determine the binding spectrum of the anti-NV Fabs, binding assays were performed in an ELISA with rVLPs derived from representative human NoVs: NV (GI.1), NV-2007 (GI.1), Hawaii (GII.1) and MD-145 (GII.4). As shown in FIG. 1B, four of the five Fabs were reactive with both prototype NV (circulating in 1968) and NV-2007 (circulating in 2007)(Nenonen et al., 2009, J Clin Virol 45:105-8) whereas Fab G4 was reactive only with NV. The five Fabs were not reactive with rVLPs from GII. The absence of cross-reactivity with strains from GII was consistent with the serotypic differences established between NV and HV in cross-challenge studies (Wyatt et al., 1974, J Infect Dis 129:709-14).

The binding affinities to NV-VLP were measured by SPR on a Biacore machine. High affinities with a $K_d$ range of 0.8 nM to 1.9 nM were observed for all anti-NV clones. In general, anti-NV Fabs had relatively fast on-rates and medium off-rates (Table 1).

TABLE 1

Affinities of anti-NV Fabs determined by SPR[1]

| Fab | $k_{off}$ (1/s) | $k_{on}$ (1/Ms) | $K_d$ (M) |
|---|---|---|---|
| D8 | $1.56 \times 10^{-3}$ | $2.02 \times 10^6$ | $7.72 \times 10^{-10}$ |
| B7 | $1.53 \times 10^{-3}$ | $1.89 \times 10^6$ | $8.09 \times 10^{-10}$ |
| G4 | $1.42 \times 10^{-3}$ | $1.46 \times 10^6$ | $9.74 \times 10^{-10}$ |
| E5 | $4.18 \times 10^{-3}$ | $2.23 \times 10^6$ | $1.89 \times 10^{-9}$ |
| F11 | $6.55 \times 10^{-4}$ | $4.42 \times 10^5$ | $1.48 \times 10^{-9}$ |

[1]Binding kinetics of antibody Fab fragments to NV-like particle (NVLP)was assessed by surface plasmon resonance (SPR) using a Biacore 1000

Analysis of the H and L chain repertoire within our panel of Abs showed that a single $V_H3$ family with a biased usage of JH4 gene segment was present in the heavy chains and a single VK1 family was present in the light chains (Table 2).

This marked restriction in V gene usage suggests that significant structural constraints may be operating in the selection of antibodies to NV. Similar restriction in gene usage has been reported for Abs against other antigens, including rotavirus (Tian et al, 2008, J Immunol 180:3279-88), hepatitis C (Carbonari et al., 2005, J Immunol 174: 6532-9), Rhesus D antigen (Andersen et al., 2007, Mol Immunol 44:412-22) and H. influenzae capsule polysaccharide (Pinchuk et al., 1995, Scand J Immunol 41:324-30). Sequences in the variable regions of both heavy and light chains were mutated in-frame without stop codons, as expected from affinity-matured plasma cells. All sequences had unique VDJ joint regions (FIG. 2), with the mutation frequency from 5-13% for heavy chains and 1-6% for light chains (Table 2).

TABLE 2

Assignment of genes coding for NV-neutralizing mAbs to their closest human germ line counterparts, based on nucleotide sequence homology[a]

| | Germline genes in: | | | | | | |
|---|---|---|---|---|---|---|---|
| | Heavy chain | | | | Light chain | | |
| Fab | V-gene | Identity[b] | J-gene | D-gene | V-gene | Identity | J-gene |
| B7 | IGHV3-7 | 92% | IGHJ4 | IGHD6-25 | IGKV1-39 | 94% | IGKJ5 |
| D8 | IGHV3-74 | 90% | IGHJ4 | IGHD5-12 | IGKV1-27 | 95% | IGKJ3 |
| E5 | IGHV3-23 | 89% | IGHJ4 | IGHD5-12 | IGKV1-27 | 99% | IGKJ4 |
| G4 | IGHV3-23 | 87% | IGH14 | IGHD1-26 | IGKV1-5 | 94% | IGKJ4 |
| F11 | IGHV3-66 | 95% | IGHJ6 | IGHD6-13 | IGKV1-37 | 95% | IGKJ2 |

[a]The closest human V-gene germ lines were identified by search of the IMGT database at http://www.imgt.org/.
[b]The $V_H$ and $V_L$ genes before CDR3 region were used to calculate the percent nucleotide acid identity. The mutations in the first 20 base pairs were excluded since these mutations could be introduced by PCR primers.

This range of mutation rate is consistent with an antigen-driven immune response (Tomlinson et al., 1996, J Mol Biol 256:813-17) and may account for the high affinities of these Fabs (Table 1). Although mutations were detected in the framework regions, most differences were within the CDRs (FIG. 2), consistent with other reported Ab-Ag interactions (Amit et al., 1986, Science 233:747-53).

Example 3

Anti-NV Fabs Recognize Conformational Epitopes on NV VP1

It was first determined that none of the anti-NV Fabs was reactive with denatured NV rVLP protein in Western blots, indicating that the Fabs likely recognize conformational epitopes present in hetero-oligomeric forms of the capsid protein. To map the conformational epitopes, a series of constructs that expressed full-length and truncated forms of the NV VP1 were generated to localize the binding sites of the antibodies by a radioimmunoprecipitation assay (RIPA). Fabs B7, D8, E5 and G4 displayed the same binding pattern shown in FIG. 3A. Deletion of the N-terminal region of VP1 through most of the S domain did not affect Fab binding. However, deletion into the P domain from either the N- or C-terminus resulted in complete abolishment of antibody binding. This result suggests that anti-NV Fabs bind to conformational epitopes that require presentation in the context of virtually entire P domain of VP1.

To address whether the conformational epitopes are present in the monomeric form of VP1, a strategy was applied using yeast surface display. In principle, yeast-displayed VP1 is expressed in a monomeric form since the VP1 is expressed fused with the yeast Aga2 protein and displayed on the yeast cell surface. The expression of VP1 and the binding of each MAb was monitored by flow cytometry for the detection of ALEXA® Fluor 488, which is directed to the c-myc tag at the c-terminus of VP1 (display fluorescence) and the DyLight 649, which is directed to the MAb/Fabs (the Ab binding fluorescence). The display fluorescence was detectable in cells transformed with the VP1 construct, indicating a positive expression of the VP1 on the yeast surface. Anti-NV Fabs B7, D8, E5 and G4 along with a control MAb, mouse anti-NV MAb NV4 were tested for binding. The MAb NV4 recognizes a conformational epitope within the P domain based on WB and domain swap. As shown in FIG. 3B, more than 40% of cells, when incubated with the mouse MAb NV4, were positive for Ab binding fluorescence, indicating this antibody can recognize an epitope present in monomeric form. However, cells treated with any one of the four chimp anti-NV Fabs showed negative Ab binding fluorescence, suggesting that they recognize conformational epitopes present in hetero-oligomeric forms such as dimers. The negative results with the Fabs were confirmed by testing IgGs of MAb D8 and B7.

To assess the spatial relationship of antigenic sites in the P domain, the five anti-NV Fabs were examined in a competitive SPR assay. The assay is based on the assumption that the full occupancy of a specific epitope in the P domain by a given Fab would compete with a second Fab that recognizes the homologous epitope. Four distinguishable epitopes were identified based on the competition patterns (Table 3).

Among them, Fab B7, G4 and F11 each recognized a distinct epitope because their binding did not inhibit the binding of any other Fabs. In contrast, D8 and E5 shared an epitope that is distinct from other epitopes.

Example 4

Fab G4 Recognizes a Specific Site on VP1 Involving Amino Acid Residue G365

Eight amino acid differences were identified between the VP1 proteins of NV and SW-2007.

Among them, three residues, G365N, V370I and I376V were located at the P2 subdomain, and one (Y410F) was adjacent to P2 (FIG. 4A). Cells transfected with vector carrying the VP1 of NV with single, double or triple mutations were incubated with Fab B7, D8, E5 and G4, respectively, and examined by immunofluorescence assay. The data showed that G365 in VP1 is a critical residue for G4 binding since the G365N mutation, whether presented as a single mutation or combined with other mutations, abolished G4 binding (FIG. 4B). Mutation of the other three varying residues did not affect the G4 binding. The G365N mutant was still reactive to the other three Fabs (FIG. 4B). Examination of the X-ray structure of NV VP1 revealed that G365 is located near, but not in, the HBGA-binding site (FIG. 4C). Because the G4 Fab significantly blocked the binding of Norwalk hyperimmune serum to NV VLP antigen, it is likely that it binds to a dominant epitope on the virion surface (FIG. 5).

Example 5

Anti-NV MAbs Block HBGA-Binding by NV and Prevent Infection in Chimps

Anti-NV Igs were tested in available functional assays for Nov antibodies. First, the Igs were tested in an HBGA carbohydrate binding blocking assay, which has been proposed as a surrogate neutralization assay (Harrington et al., 2002, J Virol 76:12335-43). As shown in FIG. 6, all the MAbs blocked the binding of NV rVLPs to H1 HBGA carbohydrate in a dose-dependent manner. The estimated concentration for yielding 50% blocking is 2.5 nM for D8, 7.3 nM for B7, 4.7 nM for E5, 2.8 nM for G4 and 10.7 nM for F11. It has been recently reported that the antibody hemagglutination inhibition activity (HAI) correlates with protection from gastroenteritis in persons infected with NV (Czako et al., 2012, Clin Vaccine Immunol 19:284-7).

Thus, the HAI ability of the MAbs was tested. All five MAbs can efficiently inhibited viral hemaggluniation activity at an antibody concentration of approximately 8 nM. It was tested whether HBGA blocking activity correlated with in vivo neutralization in chimpanzees (Bok et al., 2011, Proc Natl Acad Sci USA 108:325-30). Due to the limited availability of chimpanzees for the experiment, D8 was chosen for conversion into IgG and testing in the animal model, given its relatively higher binding affinity. An antibody-negative chimpanzee was administered a known infectious NV inoculum that was pre-incubated with D8 antibody and the chimpanzee was monitored for NV infection. The result showed that the chimpanzee did not shed virus or develop a serologic response, consistent with neutralization of NV by the D8 antibody.

Like NoVs, other pathogenic RNA viruses such as human immunodeficiency virus (HIV), hepatitis C virus (HCV) and influenza virus are markedly diverse (Nobusawa et al., 1991, Virology 182:475-85; Robertson et al., 2000, Science 288:55-6; Simmonds et al, 2005, Hepatology 42:962-73; Webster et al., 1992, Microbiol Rev 56:152-79). In recent years, several promising broadly-neutralizing MAbs against HIV, HCV and influenza viruses have been reported (Corti et al., Science 333:850-6, 2011; Johansson et al., 2007, Proc Natl Acad Sci USA 104:16269-74; Law et al., 2009, Nat Med 14:25-7; Whittle et al., 2011, Proc Natl Acad Sci USA 108:14216-21; Wu et al., 2010, Science 329:856-61). These MAbs can be useful for immunoprophylaxis, and knowledge of their binding sites can inform universal vaccine design.

Analysis of the binding spectrum of antibodies isolated from chimpanzees immunized with NV in this study showed that four of the five Fabs were specific for GI.1 viruses and the remaining one was exquisitely specific for NV with no cross-reaction with NoVs from other genotypes. The finding may partly explain why there is lack of heterotypic immunity for NoVs.

Thus, four of the anti-NV Fabs recognized conformational epitopes located within the P domain of the capsid protein (VP1). The entire P domain in an oligomeric form is absolutely required to maintain the correct conformation. Four distinguishable epitopes were identified through competitive SPR. Among them, G4 epitope was mapped to a specific site involving the G365 residue in the P2 subdomain. This G4 epitope could be a major neutralizing epitope, as indicated by blocking assay and HAI. An antibody cocktail could be used that targets several different epitopes.

NoVs are a diverse group of viruses (Zeng et al., 2006, Virology 346:312-23), and there is increasing recognition of their role in serious diarrheal illness (Glass et al., 2009, N Engl J Med 361:1776-88; Patel et al., 2008, Emerg Infect Dis 14:1224-31). The proof-of-concept approach used herein for the development of functional antibodies directed against NV is applicable to other NoVs, including the predominant GII.4 viruses.

Neutralizing MAbs against NoVs can be used as emergency prophylaxis to protect individuals in the proximity of a developing NoV outbreak, or when encountering an increased risk of exposure. The antibodies can also be used in treatment to alleviate chronic NoV gastroenteritis in debilitated or immunocompromised individuals.

Example 6

Monoclonal Antibodies that Specifically Bind to NoV GII.4

MAbs C9. G3 and B72 were isolated by phage display technology from the bone marrow of chimpanzees immunized with NoV GII.4. VLP and the mAb D4 was isolated from PBMCs of the immunized chimpanzees by single-cell PCR. The genes coding for the variable domains of the heavy (VH) and light chains of NoV gII.4-specific mAbs were sequenced and aligned. Complementarity-determining regions (CDR 1-3) shown in boxes and framework regions (FWR) were assigned according to Kabat nomenclature (Wu, T. T. Kabat, E. A., 1970, J. Exp. Med. 132(2):211-50). In FIG. 7, amino acids were expressed as single letters and dashes denote the absence of corresponding residues relative to the longest sequence.

Anti-NoV GII.4 mAbs were tested in available functional assays for NoV antibodies. The IgGs were tested in an HBGA carbohydrate binding blocking assay, which has been proposed as a surrogate neutralization assay. Briefly, IgGs were two-fold serially diluted and incubated 2 h with 1.5 μg/mL NoV GII.4 rVLP, and the IgG-NoV VLP mixture was then transferred into NeutriAvidin-coated plates (Pierce) containing biotinylated H3 carbohydrate (Glycotech) and incubated for 1 h. The binding of captured NV VLP was determined by incubation with guinea pig anti-NV hyperimmune serum (1:2,000 dilution), followed by incubation with a peroxidase-conjugated goat anti-guinea pig serum (1:2,000 dilution; KPL). The reaction was visualized with peroxidase substrate 2,2'-azino-bis(3-ethylbenzthiazoline-6-sulphonic acid, ABTS; KPL) and read at 405 nm with a Dynex Technologies Revelation 4.25 plate reader (Dynatech). All incubations were performed at room temperature. The 50% blocking antibody titer (BT50) was defined as the reciprocal of the lowest antibody dilution tested that blocked at least 50% of binding compared with that in the absence of antibody pretreatment (control binding). Results showed that all mAbs can efficiently block the HBGA binding by VLP. Blocking the HBGA binding by NoV GII.4 VLP in response to different concentrations of each IgG is shown in FIG. 8.

TABLE

Affinities of anti-GII.4 NV Fabs determined by SPR[1]

| Fab | $k_{off}$ (1/s) | $k_{on}$ (1/Ms) | $K_d$ (M) |
|---|---|---|---|
| B72 | $5.66 \times 10^{-5}$ | $1.61 \times 10^5$ | $3.51 \times 10^{-10}$ |
| C9 | $3.82 \times 10^{-3}$ | $1.38 \times 10^5$ | $2.77 \times 10^{-8}$ |
| D4 | $1.78 \times 10^{-4}$ | $1.47 \times 10^6$ | $1.21 \times 10^{-10}$ |
| G3 | $4.21 \times 10^{-4}$ | $1.62 \times 10^5$ | $2.61 \times 10^{-9}$ |

[1]Binding kinetics of antibody Fab fragments to MD145 virus-like particle (NVLP)was assessed by surface plasmon resonance (SPR) using a Biacore 1000

Example 7

Epitope Mapping

GI Monoclonal Antibodies

VLP constructed with a Norwalk virus P domain and a heterologous S domain. This result suggests that the epitope is located in the P domain of the virus capsid.

GII Monoclonal Antibodies

| Norovirus VLP | D4 | C9 | B7 | G3 |
|---|---|---|---|---|
| DC4871 (GII.4) | + | | | + |
| DC5191 (GII.4) | + | | | + |
| JHH3 (GII.4) | | | | + |
| MD145 (GII.4) | + | + | + | + |
| HS191 (GII.4) | + | + | + | + |
| JHH3 (GII.4) P domain* | | | | + |
| Ligocyte consensus GII.4[1] | | | | + |

*VLP constructed with a JHH3 (GII.4) P domain and a heterologous S domain. This result suggests that the epitope is located in the P domain of the virus capsid.
[1]Consensus VLP constructed as a potential vaccine candidate. The "consensus" sequence to model this VLP was obtained from an alignment of GII.4 sequences (Parra et al., Vaccine 30: 3580-6, 2012).

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated monoclonal antibody comprising a heavy chain variable domain and a light chain variable domain, wherein the heavy chain variable domain comprises a heavy chain complementarity determining region (HCDR)1, an HCDR2 and an HCDR3,
wherein the light chain variable domain comprises a light chain complementarity determining region (LCDR)1, and LCDR2 and an LCDR3, and wherein:
(a) the HCDR1 comprises the amino acid sequence set forth as SEQ ID NO: 82, the HCDR2 comprises the amino acid sequence set forth as SEQ ID NO: 84, and the HCDR3 comprises the amino acid sequence set forth as SEQ ID NO: 86 and the LCDR1 comprises the amino acid sequence set forth as SEQ ID NO: 90, the LCDR2 comprises the amino acid sequence set forth as SEQ ID NO: 92, and the LCDR3 comprises the amino acid sequence set forth as SEQ ID NO: 94;
(b) the HCDR1 comprises the amino acid sequence set forth as SEQ ID NO: 98, the HCDR2 comprises the amino acid sequence set forth as SEQ ID NO: 100, and the HCDR3 comprises the amino acid sequence set forth as SEQ ID NO: 102 and the LCDR1 comprises the amino acid sequence set forth as SEQ ID NO: 106, the LCDR2 comprises the amino acid sequence set forth as SEQ ID NO: 108, and the LCDR3 comprises the amino acid sequence set forth as SEQ ID NO: 110;
(c) the HCDR1 comprises the amino acid sequence set forth as SEQ ID NO: 114, the HCDR2 comprises the amino acid sequence set forth as SEQ ID NO: 116, and the HCDR3 comprises the amino acid sequence set forth as SEQ ID NO: 118 and the LCDR1 comprises the amino acid sequence set forth as SEQ ID NO: 122, the LCDR2 comprises the amino acid sequence set forth as SEQ ID NO: 124, and the HCDR3 comprises the amino acid sequence set forth as SEQ ID NO: 126; or
(d) the HCDR1 comprises the amino acid sequence set forth as SEQ ID NO: 130, the HCDR2 comprises the amino acid sequence set forth as SEQ ID NO: 132, and the HCDR3 comprises the amino acid sequence set forth as SEQ ID NO: 134 and the LCDR1 comprises the amino acid sequence set forth as SEQ ID NO: 138, the LCDR2 comprises the amino acid sequence set forth as SEQ ID NO: 140, and the LCDR3 comprises the amino acid sequence set forth as SEQ ID NO: 142,
and wherein the monoclonal antibody specifically binds to a Norovirus viral protein VP1 with a $K_D$ of 1 nM or less.

2. The isolated monoclonal antibody of claim 1, wherein the heavy chain variable domain comprises the amino acid sequence set forth as one of SEQ ID NO: 88, SEQ ID NO: 104, SEQ ID NO: 120, or SEQ ID NO: 136.

3. The isolated monoclonal antibody of claim 1, wherein the light chain variable domain comprises the amino acid sequence set forth as SEQ ID NO: 96, SEQ ID NO: 112, SEQ ID NO: 128 or SEQ NO: 144.

4. The isolated monoclonal antibody of claim 1, wherein:
   (a) the heavy chain variable domain comprises the amino acid sequence set forth as SEQ ID NO: 88 and the light chain variable domain comprises the amino acid sequence set forth as SEQ ID NO: 96;
   (b) the heavy chain variable domain comprises the amino acid sequence set forth as SEQ ID NO: 104 and the light chain variable domain comprises the amino acid sequence set forth as SEQ ID NO: 112;
   (c) the heavy chain variable domain comprises the amino acid sequence set forth as SEQ ID NO: 120 and the light chain variable domain comprises the amino acid sequence set forth as SEQ ID NO: 128 or
   (d) the heavy chain variable domain comprises the amino acid sequence set forth as SEQ ID NO: 136 and the light chain variable domain comprises the amino acid sequence set forth as SEQ ID NO: 144.

5. The isolated monoclonal antibody of claim 1, wherein the antibody is an IgG, IgM or IgA.

6. The isolated monoclonal antibody of claim 1, wherein the antibody is humanized or chimeric.

7. An isolated antigen binding fragment of the isolated monoclonal antibody of claim 1.

8. The isolated antigen binding fragment of claim 7, wherein the fragment is a Fab fragment, a Fab' fragment, a F(ab)'$_2$ fragment, a single chain Fv protein (scFv), or a disulfide stabilized Fv protein (dsFv).

9. The isolated monoclonal antibody of claim 1, or an antigen binding fragment thereof, wherein the antibody or the antigen binding fragment is labeled.

10. The isolated monoclonal antibody or antigen binding fragment of claim 9, wherein the label is a fluorescent, an enzymatic, or a radioactive label.

11. A composition comprising an effective amount of the antibody of claim 1, or an antigen binding fragment thereof, and a pharmaceutically acceptable carrier.

12. An isolated nucleic acid molecule encoding the monoclonal antibody of claim 1 or an antigen binding fragment thereof.

13. The isolated nucleic acid molecule of claim 12, operably linked to a promoter.

14. An expression vector comprising the isolated nucleic acid molecule of claim 12.

15. An isolated host cell transformed with the vector of claim 14.

16. A method of detecting a Norovirus infection in a subject comprising:
   contacting a biological sample from the subject with at least one isolated monoclonal antibody of claim 1 or an antigen binding fragment thereof; and
   detecting antibody bound to the sample,
   wherein the presence of antibody bound to the sample indicates that the subject has an Norovirus infection.

17. The method of claim 1, wherein the presence of antibody bound to the sample indicates that the subject has a Norovirus infection.

18. The method of claim 16, wherein the isolated monoclonal antibody is directly labeled.

19. The method of claim 16, further comprising:
   contacting the sample with a second antibody that specifically binds the isolated human monoclonal antibody; and
   detecting the binding of the second antibody,
   wherein an increase in binding of the second antibody to the sample as compared to binding of the second antibody to a control sample detects the presence of the Norovirus infection the subject.

20. A method for inhibiting a Norovirus infection in a subject, comprising administering to the subject a therapeutically effective amount of claim 1, or an antigen binding fragment thereof, thereby inhibiting the Norovirus infection.

21. The method of claim 20, further comprising administering to the subject an anti-viral agent.

22. The method of claim 20, further comprising measuring viral titer in the subject.

* * * * *